(12) United States Patent
Bahrami et al.

(10) Patent No.: US 11,318,305 B2
(45) Date of Patent: May 3, 2022

(54) SYSTEMS AND METHODS FOR IMPROVED TISSUE-SENSING BASED ELECTROPORATION

(71) Applicant: OncoSec Medical Incorporated, San Diego, CA (US)

(72) Inventors: Arya Bahrami, La Jolla, CA (US); Douglas W. Brown, San Diego, CA (US); Jean Campbell, Seattle, WA (US); Richard J. Connolly, San Diego, CA (US); Andy E. Denison, Temecula, CA (US); Christopher S. Hayden, Winchester, CA (US); Eric T. Johnson, Temecula, CA (US); Robert H. Pierce, Seattle, WA (US); Robert R. Ragland, Temecula, CA (US)

(73) Assignee: ONCOSEC MEDICAL INCORPORATED, San Diego, CA (US)

( * ) Notice: Subject to any disclaimer, the term of this patent is extended or adjusted under 35 U.S.C. 154(b) by 360 days.

(21) Appl. No.: 15/563,462

(22) PCT Filed: Mar. 31, 2016

(86) PCT No.: PCT/US2016/025416
§ 371 (c)(1),
(2) Date: Sep. 29, 2017

(87) PCT Pub. No.: WO2016/161201
PCT Pub. Date: Oct. 6, 2016

(65) Prior Publication Data
US 2019/0117964 A1 Apr. 25, 2019

Related U.S. Application Data

(60) Provisional application No. 62/141,142, filed on Mar. 31, 2015, provisional application No. 62/141,182, (Continued)

(51) Int. Cl.
*A61N 1/32* (2006.01)
*A61N 1/02* (2006.01)
*A61N 1/04* (2006.01)

(52) U.S. Cl.
CPC .............. *A61N 1/327* (2013.01); *A61N 1/025* (2013.01); *A61N 1/0424* (2013.01)

(58) Field of Classification Search
CPC ....... A61N 1/327; A61N 1/025; A61N 1/0424
(Continued)

(56) References Cited

U.S. PATENT DOCUMENTS 6,387,671 B1 * 5/2002 Rubinsky ............. A61B 5/0536
435/173.1
6,912,417 B1 6/2005 Bernard et al.
(Continued)

FOREIGN PATENT DOCUMENTS

CN 1195997 A 10/1998
CN 101563132 A 10/2009
(Continued)

OTHER PUBLICATIONS

Office Action for Japanese Application No. 2017-559038 dated May 25, 2020.
(Continued)

*Primary Examiner* — Carl H Layno
*Assistant Examiner* — Michael J Lau
(74) *Attorney, Agent, or Firm* — Alston & Bird LLP

(57) ABSTRACT

An adaptive control method for controlling EP pulse parameters during electroporation (EP) of cells or tissue using an
(Continued)

EP system includes providing a system for adaptive control to optimize EP pulse parameters including EP pulse parameters, applying voltage and current excitation signals to the cells, obtaining data from the current and voltage measurements, and processing the data to separate the desirable data from the undesirable data, extracting relevant features from the desirable data, applying at least a portion of the relevant features to a trained diagnostic model, estimating EP pulsing parameters based on an outcome of the applied relevant features, where the initialized EP pulsing parameters are based on the trained model and the relevant features, to optimize the EP pulsing parameters, and applying, by the generator, a first EP pulse based on the first pulsing parameters.

23 Claims, 49 Drawing Sheets

Related U.S. Application Data filed on Mar. 31, 2015, provisional application No. 62/141,256, filed on Mar. 31, 2015, provisional application No. 62/214,807, filed on Sep. 4, 2015, provisional application No. 62/214,872, filed on Sep. 4, 2015, provisional application No. 62/141,164, filed on Mar. 31, 2015.

(58) Field of Classification Search
USPC .............................................................. 607/3
See application file for complete search history.

(56) References Cited

U.S. PATENT DOCUMENTS

| | | | | |
|---|---|---|---|---|
| 7,412,284 | B2 | 8/2008 | Hofmann | |
| 7,937,143 | B2* | 5/2011 | Demarais | A61N 1/327 604/21 |
| 8,209,006 | B2 | 6/2012 | Smith et al. | |
| 8,738,125 | B1* | 5/2014 | Heller | A61N 1/327 604/21 |
| 10,016,232 | B1 | 7/2018 | Bowers et al. | |
| 2002/0183686 | A1* | 12/2002 | Darvish | A61N 1/325 604/21 |
| 2002/0193833 | A1 | 12/2002 | Dimmer et al. | |
| 2003/0204161 | A1 | 10/2003 | Ferek-Petric | |
| 2004/0068299 | A1* | 4/2004 | Laske | A61N 1/0575 607/3 |
| 2004/0097965 | A1* | 5/2004 | Gardeski | A61M 25/0021 606/129 |
| 2005/0049542 | A1* | 3/2005 | Sigg | A61N 1/327 604/20 |
| 2006/0036210 | A1* | 2/2006 | Zhang | A61N 1/327 604/20 |
| 2006/0264807 | A1* | 11/2006 | Westersten | A61N 1/327 604/21 |
| 2007/0156082 | A1* | 7/2007 | Scherman | A61N 1/306 604/20 |
| 2008/0086107 | A1* | 4/2008 | Roschak | A61M 25/0068 604/506 |
| 2008/0200912 | A1* | 8/2008 | Long | A61B 1/018 606/37 |
| 2009/0247933 | A1* | 10/2009 | Maor | A61B 18/14 604/20 |
| 2010/0030211 | A1* | 2/2010 | Davalos | A61N 1/327 606/41 |
| 2010/0188785 | A1 | 7/2010 | Gascuel | |
| 2010/0191174 | A1 | 7/2010 | Lovell et al. | |
| 2010/0204638 | A1 | 8/2010 | Hobbs et al. | |
| 2010/0261994 | A1* | 10/2010 | Davalos | A61N 1/0412 600/411 |
| 2010/0268110 | A1 | 10/2010 | Beltran et al. | |
| 2011/0238057 | A1* | 9/2011 | Moss | A61B 18/1477 606/33 |
| 2012/0109122 | A1* | 5/2012 | Arena | A61B 18/14 606/41 |
| 2012/0123318 | A1* | 5/2012 | Ek | A61B 5/24 604/20 |
| 2012/0136308 | A1* | 5/2012 | Racz | A61M 25/007 604/164.01 |
| 2012/0310230 | A1* | 12/2012 | Willis | A61B 18/1477 606/33 |
| 2012/0323165 | A1* | 12/2012 | Broderick | A61N 1/327 604/20 |
| 2013/0006228 | A1* | 1/2013 | Johnson | A61B 18/1477 606/14 |
| 2013/0066296 | A1* | 3/2013 | Broderick | A61N 1/0502 604/501 |
| 2013/0107399 | A1 | 5/2013 | Cao et al. | |
| 2013/0260425 | A1 | 10/2013 | Doi et al. | |
| 2013/0260435 | A1* | 10/2013 | Pakhomova | C12N 13/00 435/173.6 |
| 2013/0345779 | A1* | 12/2013 | Maor | A61N 1/327 607/115 |
| 2014/0052216 | A1* | 2/2014 | Long | A61B 18/1477 607/50 |
| 2014/0121728 | A1* | 5/2014 | Dhillon | A61F 7/007 607/62 |
| 2014/0148876 | A1* | 5/2014 | Ronchetti | A61N 1/303 607/63 |
| 2014/0222105 | A1* | 8/2014 | Broderick | C12N 15/87 607/59 |
| 2014/0277219 | A1* | 9/2014 | Nanda | A61N 1/403 607/3 |
| 2019/0117964 | A1 | 4/2019 | Bahrami et al. | |
| 2020/0246612 | A1 | 8/2020 | Rodriguez et al. | |

FOREIGN PATENT DOCUMENTS

| | | | |
|---|---|---|---|
| CN | 101888874 A | 11/2010 | |
| CN | 102271607 A | 12/2011 | |
| CN | 102625676 A | 1/2012 | |
| CN | 101745178 | 1/2013 | |
| CN | 103446667 A | 12/2013 | |
| CN | 103781433 A | 5/2014 | |
| CN | 103517732 B | 9/2016 | |
| EP | 1515437 A1 | 3/2005 | |
| EP | 2701791 | 3/2014 | |
| JP | 2004-520865 T | 7/2004 | |
| JP | 2012-520739 T | 9/2012 | |
| TW | 200601437 A | 1/2006 | |
| WO | WO-1994/13804 A1 | 6/1994 | |
| WO | WO 00/56395 A1 | 9/2000 | |
| WO | WO 00/77228 A1 | 12/2000 | |
| WO | WO 02/32335 A1 | 4/2002 | |
| WO | WO-2003/011161 A1 | 2/2003 | |
| WO | WO 2005/021088 A1 | 3/2005 | |
| WO | WO-2011047387 A2 * | 4/2011 | A61M 37/00 |
| WO | WO 2013/177423 A2 | 11/2013 | |
| WO | WO 2016/146086 A2 | 9/2016 | |
| WO | WO 2016/161201 A2 | 10/2016 | |
| WO | WO 2019/213421 A1 | 11/2019 | |

OTHER PUBLICATIONS

International Search Report and Written Opinion for Application No. PCT/IB2020/050888 dated Apr. 3, 2020.
Non-Final Office Action for U.S. Appl. No. 16/269,022, dated Sep. 29, 2020.
Office Action for Taiwan Application No. 109103711 dated Aug. 18, 2020.
Ding, Wenjin, "Electroporation Therapy Effect and Development of Research on the Treatment thereof on Tumors (Effect of Electroporation Therapy in Treatment of Tumor: A Research Progress)," Chinese Medical Science, 4(9):48-52, (2014).
Office Action for Chinese Application No. 201680026625.2, dated Nov. 18, 2020.

(56) References Cited

OTHER PUBLICATIONS

Office Action for Chinese Application No. 201680026625.2 dated Apr. 16, 2021.
Brown et al., "Development of an adaptive electroporation system for intratumoral plasmid DNA delivery," Bioelectrochemistry, 122:191-198, (2018).
International Search Report and Written Opinion for Application No. PCT/US2016/025416 dated Sep. 23, 2016.
Office Action for European Patent Application No. 16717025.7, dated Jan. 3, 2019, 8 pages.
Dollar et al., Structured Forests for Fast Edge Detection, IEEE International Conference on Computer Vision, Dec. 1, 2013, pp. 1841-1848.
Rustamov et al., Wavelets on Graphs via Deep Learning, Digital Video and Audio Broadcasting Technology: A Practical Engineering Guide (3rd edition), vol. 1, Jan. 1, 2013, 10 pages.

\* cited by examiner

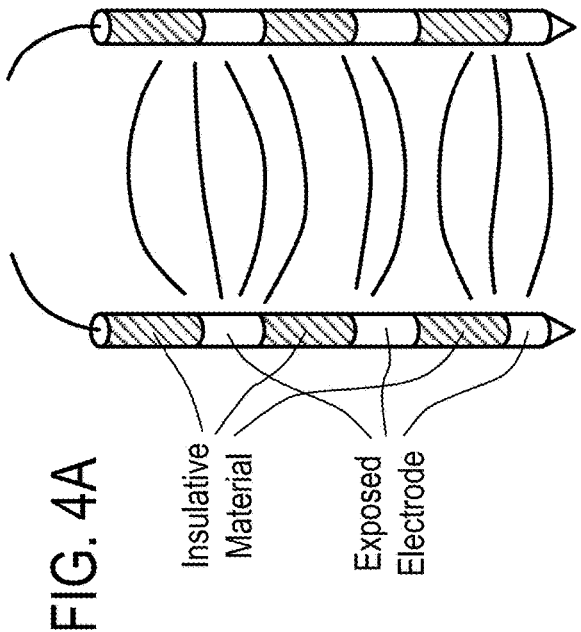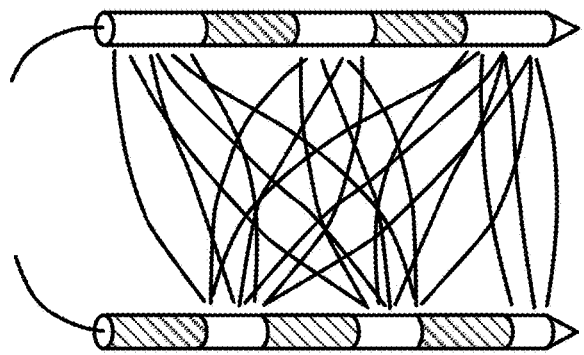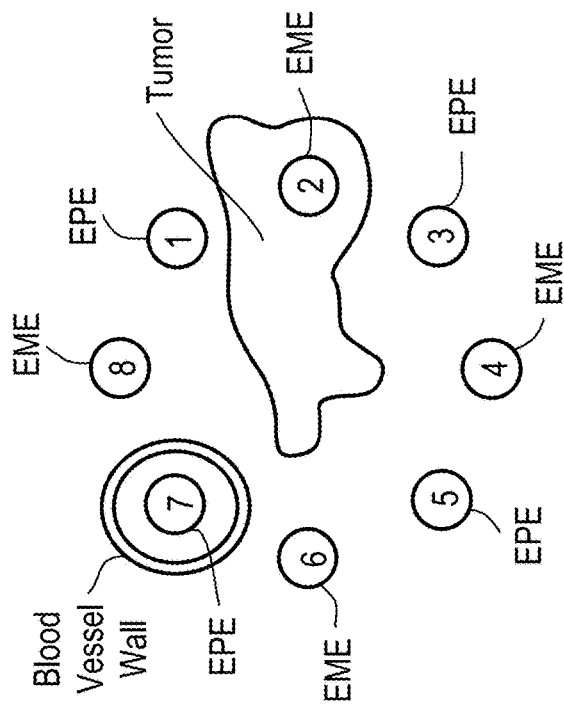

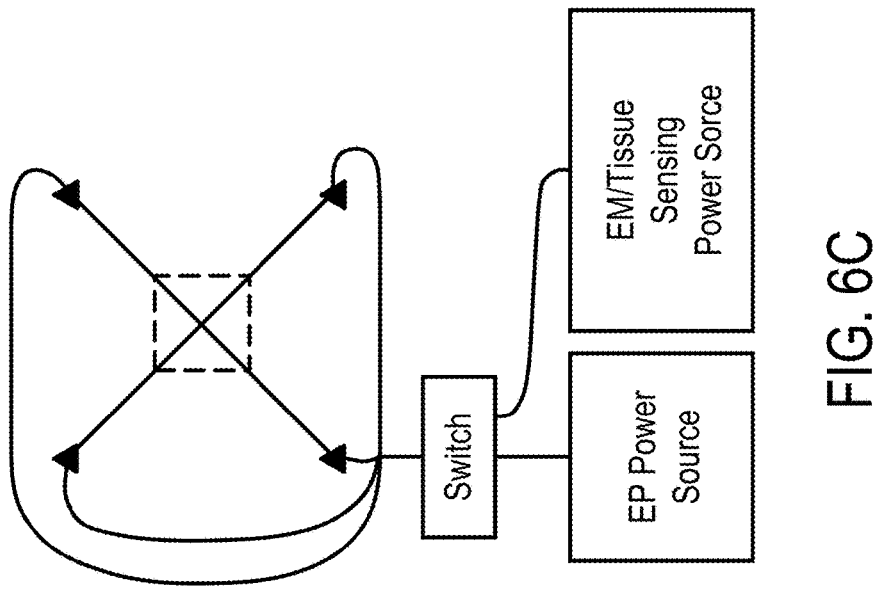
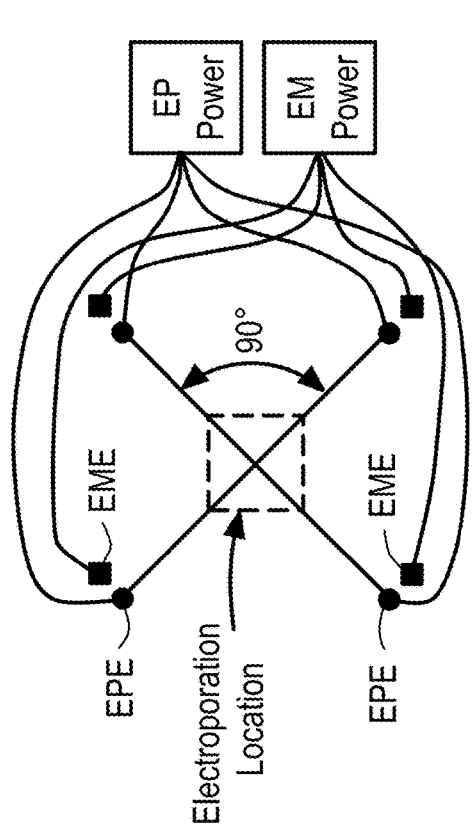
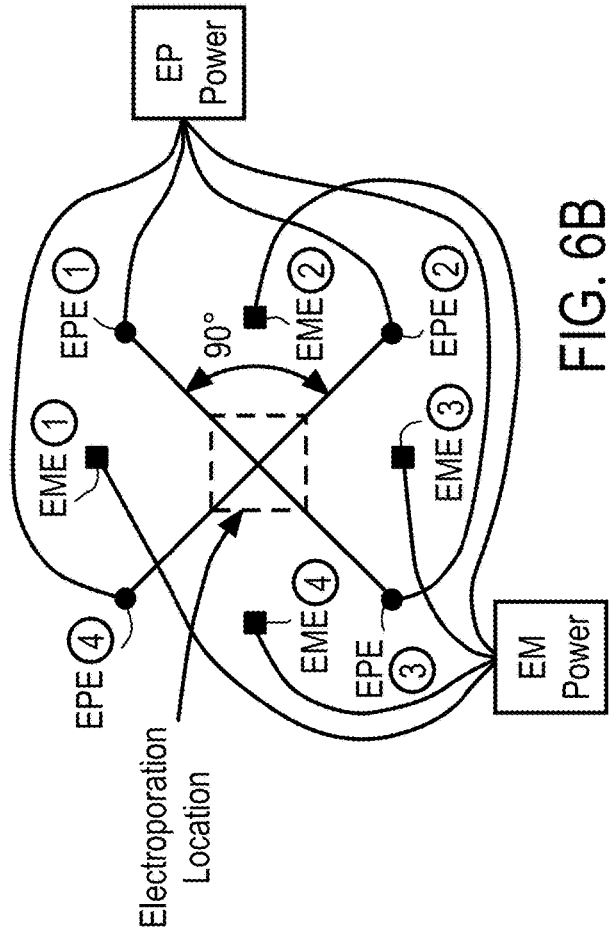

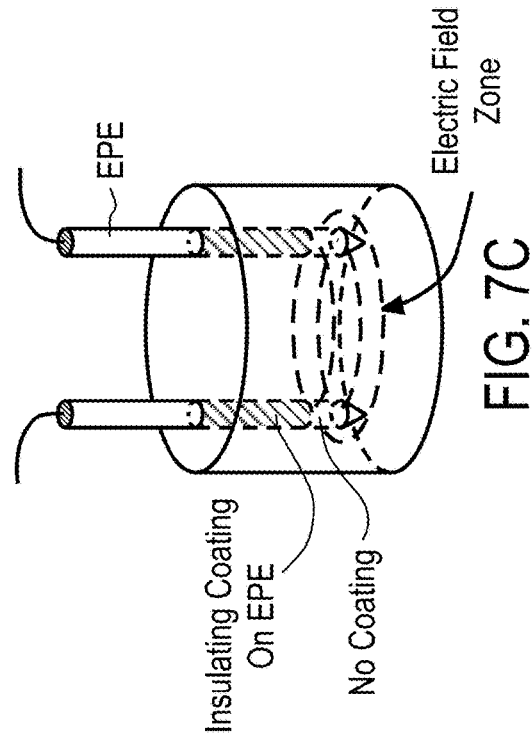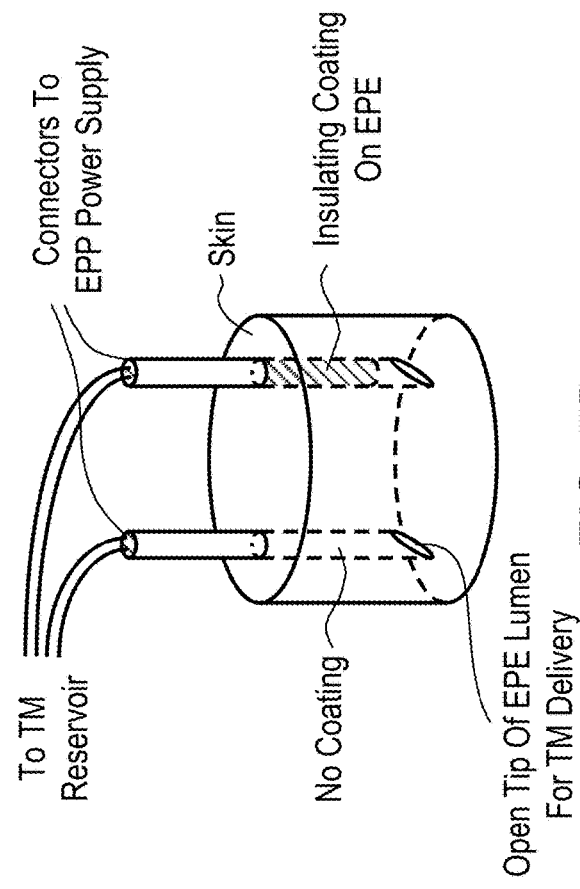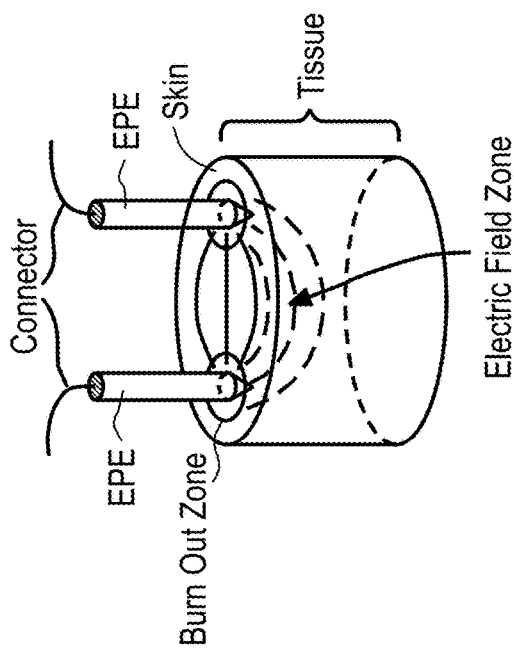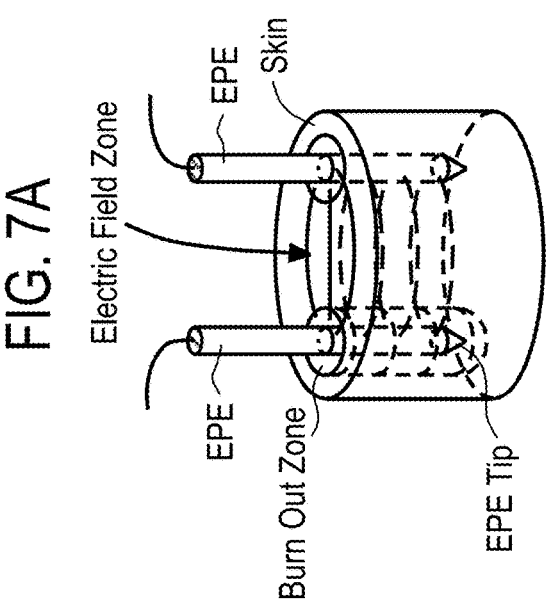

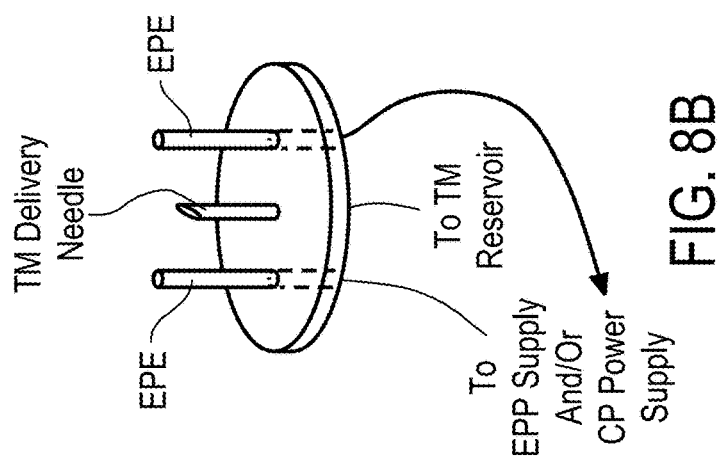
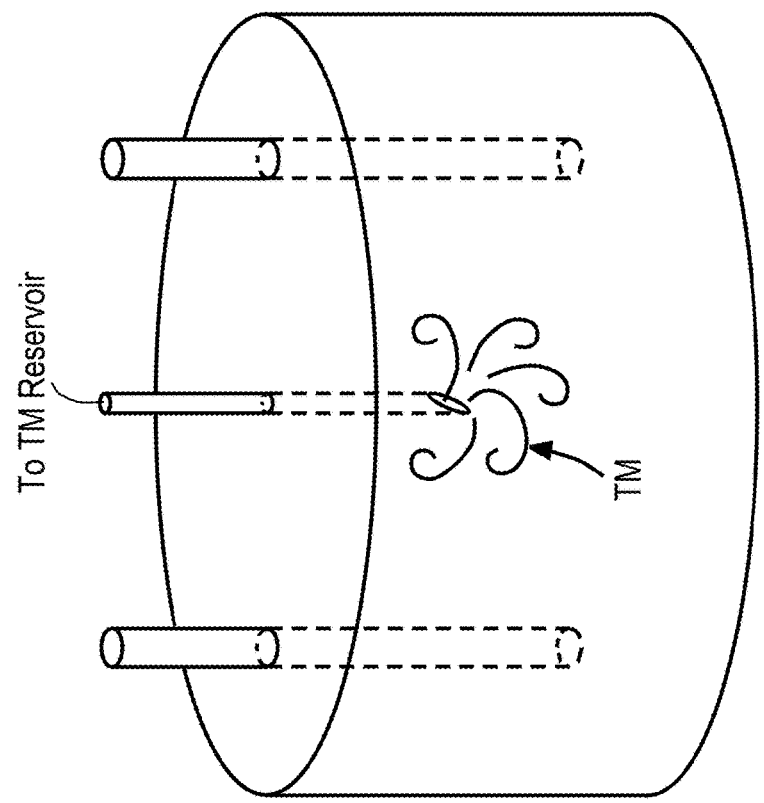
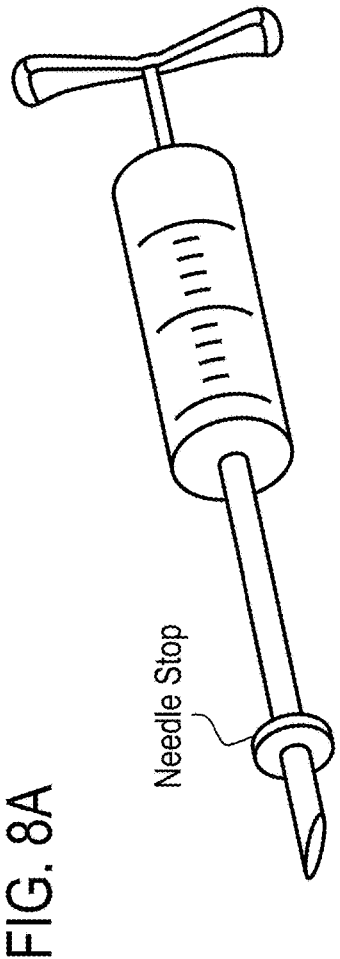
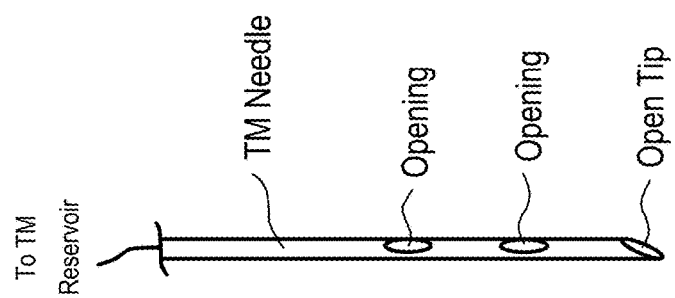

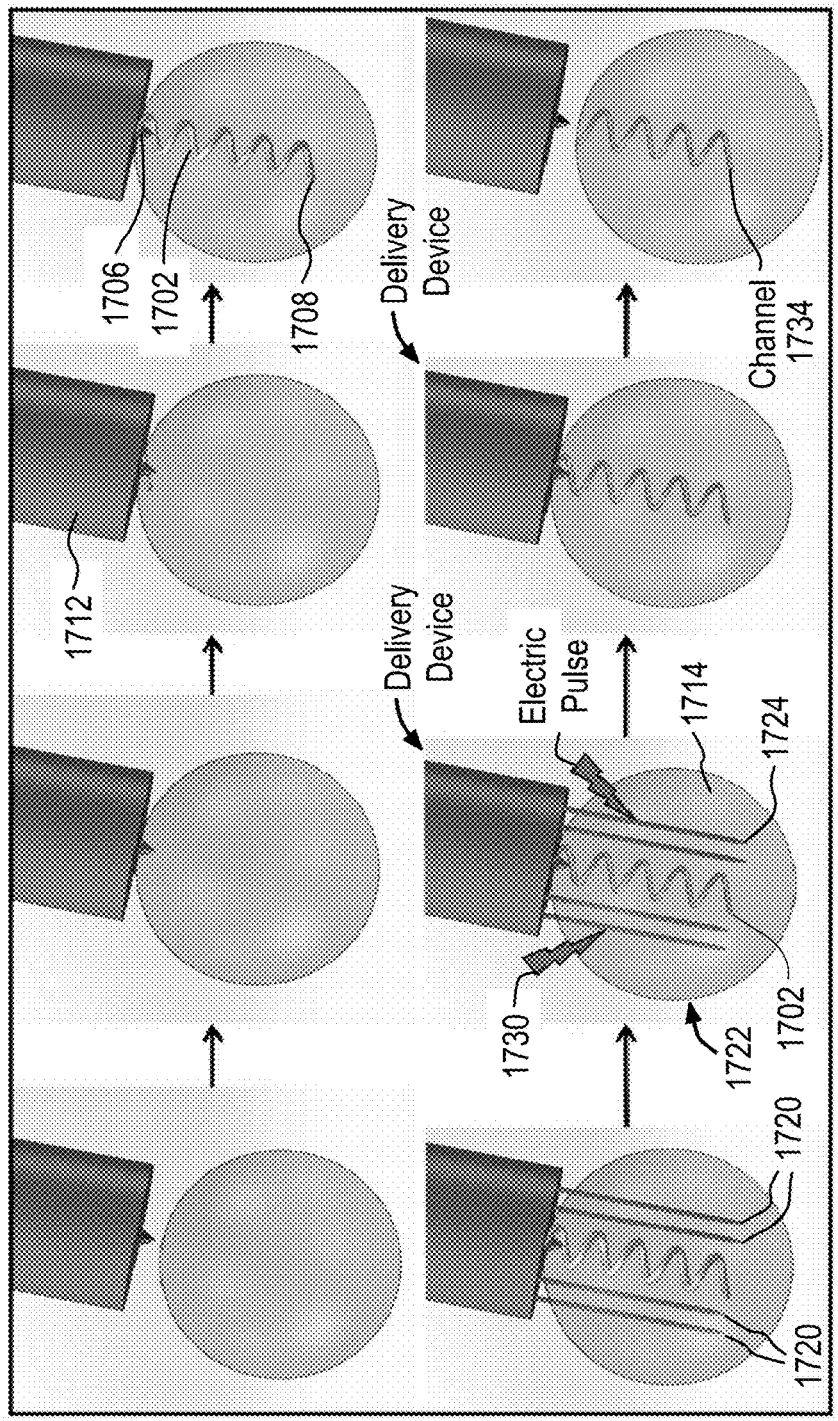
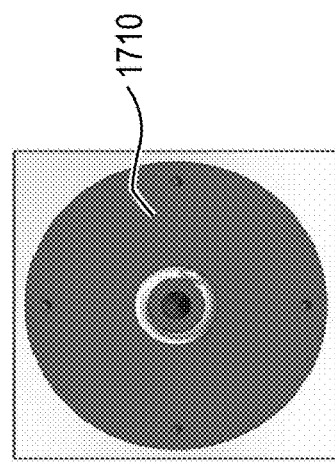
FIG. 17A
FIG. 17B

FIG. 22A
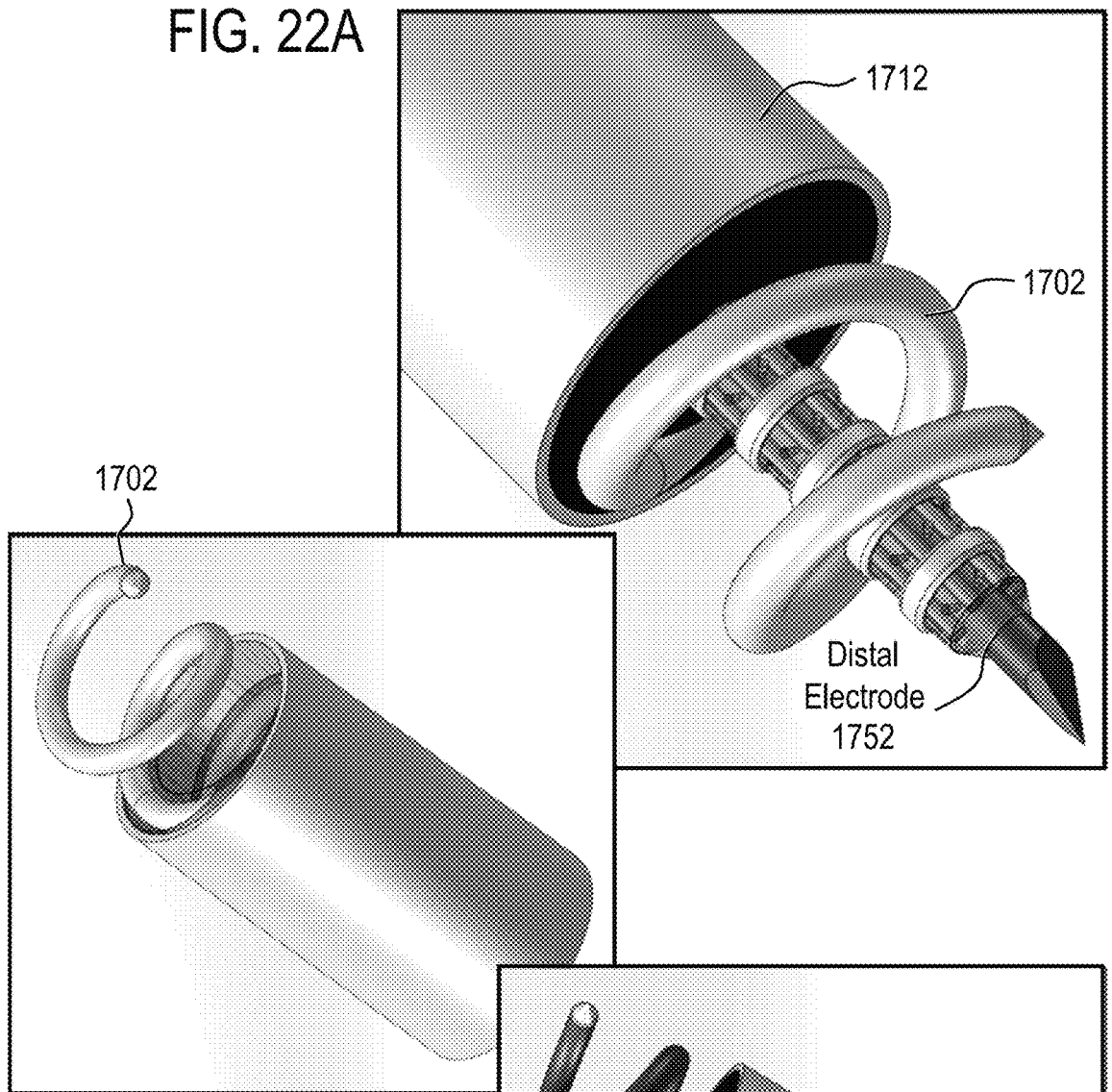
FIG. 22B
FIG. 22C
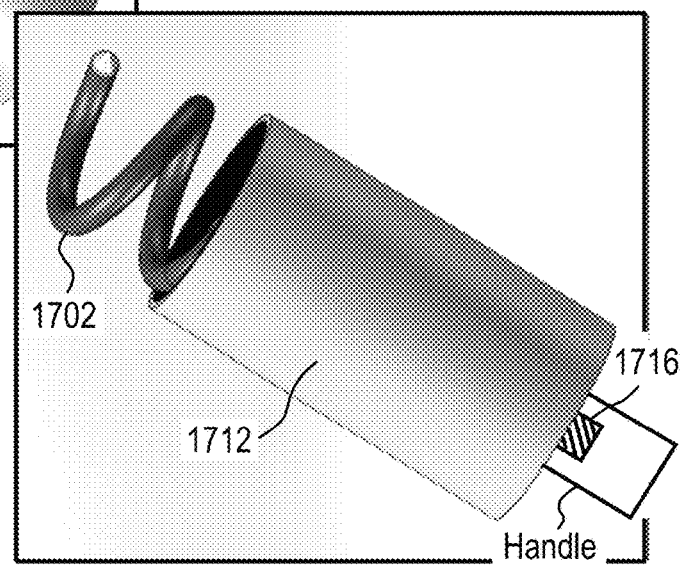

- Lead Routing and Termination
- Clutch layout
- Injection Paths
- Translation mechanism
- ~1.125" OD
- ~4" Length

- Gearbox to drive simultaneous screws (motor or hand driven)
  - Integrated delrin bushings or bearings for alignment
- Integrated Electrode Engagement paths/mechanism Non diffusing dye to indicate distribution of the drug/dna
- Corkscrew
  - 0.2ml injection
  - Tested in bovine liver
  - Small injections with every half turn of coil retraction
- Great distribution!

Table 1. Schedule of Aims (in Months)

| Aims / Duration in Months | 1 | 2 | 3 | 4 | 5 | 6 | 7 | 8 | 9 | 10 | 11 | 12 |
|---|---|---|---|---|---|---|---|---|---|---|---|---|
| Aim 1 – Evaluate Feedback Parameters | ■ | ■ | ■ | | | | | | | | | |
| Aim 2 – Verification Experiment | | | | ■ | ■ | ■ | ■ | ■ | | | | |
| Aim 3 – Validation Experiment | | | | | | | | | ■ | ■ | ■ | ■ |
| Final Report | | | | | | | | | | | | ♦ |

Figure 49

SYSTEMS AND METHODS FOR IMPROVED TISSUE-SENSING BASED ELECTROPORATION

REFERENCE TO RELATED APPLICATIONS

The present application claim priority to U.S. Provisional Patent Application No. 62/214,807 filed Sep. 4, 2015 entitled "SYSTEM AND METHOD FOR OPTIMIZED ELECTROPORATION," and U.S. Provisional Patent Application No. 62/214,872 filed Sep. 4, 2015 entitled "SYSTEM AND METHOD FOR OPTIMIZED CATHETER-BASED ELECTROPORATION," each of which relates to U.S. Provisional Patent Application No. 62/141,142 filed Mar. 31, 2015 entitled "FOCUSED PULSE ADDITION ELECTROPORATION," U.S. Provisional Patent Application No. 62/141,182 filed Mar. 31, 2015 entitled "ELECTROCHEMICAL TISSUE SENSING," U.S. Provisional Patent Application No. 62/141,256 filed Mar. 31, 2015 entitled "ALL-IN-ONE DEVICE FOR IMPROVED THERAPEUTIC AGENT DELIVERY" and U.S. Provisional Patent Application No. 62/141,164 filed Mar. 31, 2015 entitled "DEVICE FOR IMPROVED THERAPEUTIC AGENT DELIVERY", the disclosures of which are expressly incorporated herein by reference in their entireties.

FIELD OF THE INVENTION

The present invention relates generally to the use of control systems to improve an electroporation process and to increase the permeability of cells, and more specifically to a method and apparatus for optimized application of controlled electric fields for delivery of therapeutic moieties into cells by electroporation therapy (EPT), also known as cell poration therapy (CPT) and electrochemotherapy (ECT).

BACKGROUND OF THE INVENTION

In the 1970's it was discovered that electric fields could be used to create pores in cells without causing permanent damage. This discovery made possible the insertion of large molecules into cell cytoplasm. It is known that therapeutic moieties such as pharmacological compounds can be incorporated into live cells through a process known as electroporation. The genes or other molecules are injected into the live cells in and short pulses of high electric fields are applied. The cell membranes are transiently made porous and the genes or molecules enter the cells, where they can modify the genome of the cell.

In the treatment of certain types of cancer with chemotherapy, it is necessary to use a high enough dose of a drug to kill the cancer cells without killing an unacceptable high number of normal cells. If the chemotherapy drug could be inserted directly inside the cancer cells, this objective could be achieved. Some of the anti-cancer drugs, for example, bleomycin, normally cannot penetrate the membranes of certain cancer cells effectively. However, electroporation makes it possible to insert bleomycin into cells.

Treatment typically is carried out by injecting an anticancer drug directly into the tumor and applying an electric field to the tumor between a pair of electrodes. The field strength must be adjusted reasonably accurately so that electroporation of the cells of the tumor occurs without damage, or at least minimal damage, to any normal or healthy cells. This can normally be easily carried out with external tumors by applying the electrodes to opposite sides of the tumor so that the electric field is between the electrodes. When the field is uniform, the distance between the electrodes can then be measured and a suitable voltage according to the formula $E=V/d$ can then be applied to the electrodes ($E$=electric field strength in V/cm; $V$=voltage in volts; and $d$=distance in cm). When large or internal tumors are to be treated, it is not easy to properly locate electrodes and measure the distance between them.

Treatment of a subject using cell poration therapy provides a means for avoiding the deleterious effects typically associated with administration of anticancer or cytotoxic agents. Such treatment would allow introduction of these agents to selectively damage or kill undesirable cells while avoiding surrounding healthy cells or tissue. One issue, however, with using electroporation techniques is that diseased tissue, particularly cancerous tissue, can be quite heterogeneous, requiring adjustment of electroporation conditions. Thus, the present invention provides the use of electrochemical impedance spectroscopy analysis methods in combination with adaptive control methods for EP to maximize the electroporation of the desired tissues while minimizing tissue damage.

SUMMARY

Accordingly, there is a need for implementing a control system using tissue-sensing based feedback to optimize the EP process with tumor-specific measurements acquired before and between each EP pulse.

In accordance with some embodiments, a system for providing adaptive control to optimize electroporation (EP) pulse parameters during EP of cells and tissue using an EP device comprises a measurement device, an initializing module, a generator, a controller, and a memory module. The measurement device is configured to measure dielectric and conductive properties of cells and tissues, and includes a voltage sensor to measure voltages across the tissue resulting from each of an excitation signal and an EP pulse applied to the tissue, and a current sensor to measure current across the tissue resulting from each of the excitation signal and the at least one applied EP pulse. The initializing module is configured to initialize EP pulsing parameters for performing electroporation in the cells or tissue, where initialized EP pulsing parameters are based at least in part on at least one trained model. The generator is configured to apply at least one of the excitation signals and the EP pulse to the tissue. The voltage sensor and current sensor of the measurement device measure voltage and current across the cells of the tissue in response to the application of the excitation signals. The controller is configured to receive a signal relating to the measured sensor data from the measurement device, corresponding to at least one of the excitation signal and the EP pulse, to fit the data to at least one trained model and to process the data into diagnostics and updated control parameters. The controller comprises a pre-processing module to receive the signal relating to the data from the current and voltage measurements, and process the data to separate desirable data from undesirable data, a feature extraction module to extract relevant features from the desirable data, a diagnostic module to apply at least a portion of the relevant features of the desirable data to at least one trained diagnostic model, and a pulse parameter estimation module to estimate at least one of initialized pulsing parameters and subsequent pulsing parameters based on an outcome of at least one of the measured data, the diagnostic module and the feature extraction module. The memory module stores the desirable and undesirable data, sensor data and the trained models for feature extraction by the controller.

In some embodiments, the EP device comprises a central probe, an applicator, and at least two oppositely charged electroporation electrodes (EPEs). The central probe defines at least a central lumen and extends from a proximal end to a distal end, at least a portion of the central probe has a spiral geometry to create a channel for delivery of therapeutic moieties to the tissue. The portion of the central probe has at least one ejection port positioned along the spiral geometry. The proximal end of the central probe is configured to receive the therapeutic moieties delivered to the central probe, and the distal end of the central probe is open to define an opening for delivery of the therapeutic moieties to the tissue and has a shape configured to pierce the tissue. The applicator houses the central probe at least partially, and has a distal end through which the portion of the central probe is configured to extend to an outside of the applicator to contact the tissue and to retract back into the applicator. The at least two oppositely charged EPEs are configured to be positioned surrounding the tissue and adapted to extend from proximal to distal ends. The distal ends have a needle shape configured to pierce the tissue. The measurement device is coupled to the EPEs, and the EPEs are adapted to be coupled to the generator to receive at least one of the excitation signal and the electrical waveform for the EP pulse.

In some embodiments, the EP device comprises a central probe, at least one channeling wire, a ramp, an electrical connector, a small bore connector, a handle, and at least two oppositely charged electrodes. The central probe defines at least a central lumen and having a proximal end and a closed distal end. A tip of the distal end has a needle shape configured to pierce tissue and has at least one exit port positioned at a predetermined position from the distal end. The exit port fluidly connects the central lumen to an outside of the central probe. The at least one channeling wire is positioned in the central lumen and slidable within the central probe, and has a proximal end positioned in the central probe and a distal end configured to extend to the outside of the central probe and retract back into the central lumen through the exit port. A tip of the distal end of the channeling wire has a shape configured to pierce through the tissue and define an opening through which at least a portion of the channeling wire enters the tissue to create a fluid channel through which the therapeutic moieties are delivered to the tissue. The therapeutic moieties are delivered from the central lumen into the channel through the exit port. The ramp is integrally formed with or coupled to the inner surface of the central probe, the inner surface defining the central lumen, and the ramp is configured to contact and guide the channeling wire to exit the central probe to the outside of the central probe. The electrical connector electrically connects the central probe and channeling wire to the generator. The small bore connector connected to the central probe for delivery of the therapeutic moieties. The handle houses the electrical connector at least in part and is coupled to the proximal end of the central probe and the channeling wire to facilitate a depth of penetration of the distal end of the central probe and the channeling wire. The at least two oppositely charged electrodes are configured to be positioned surrounding the tissue, and extend from proximal to distal ends. Tips of the distal ends have a needle shape, configured to pierce the tissue. The electrodes are adapted to be coupled to the generator, receive at least one electrical waveform from the generator, and supply the at least one excitation signal and at least one EP pulse to the tissue. The measurement device is coupled to the electrodes.

In some embodiments, the EP device comprises a trocar including a cannula and an obturator, at least two oppositely charged electrodes, and a central probe. The cannula extends from a proximal end to an open distal end and defines a first lumen configured to receive the obturator. The obturator extends from a proximal end to a distal end. The distal end has a sharp pointed shape configured to pierce through skin, penetrate into body cavities and form a path through which the cannula may be at least partially inserted into the cavity. The obturator is configured to be slidable within the first lumen, and distal end of the obturator configured to extend to an outside of the first lumen through the open distal end of the cannula. The at least two oppositely charged electrodes are retractably disposed at a distal end of an anchor and configured to be positioned surrounding the tissue. The measurement device is coupled to the electrodes and the electrodes are adapted to be coupled to a generator, receive at least one electrical waveform from the generator, and supply the at least one excitation signal and EP pulse to the zone. The central probe is retractably disposed at the distal end of the anchor and has an inner surface defining a central lumen and extending from the distal end of the anchor. At least a portion of the central probe has a spiral geometry configured to create a channel for delivery of the therapeutic moieties to the tissue. A distal end of the central probe has a shape configured to pierce the tissue and is open to define an opening for the delivery of the therapeutic moieties to the tissue.

In some embodiments, the EP device comprises an electroporation wand housing comprising an array of electroporation electrodes (EPEs), an array of electrical measurement electrodes (EMEs), where the EPEs and EMEs are offset, and a wand delivery system comprising at least one injection probe defining a first lumen. The injection probe extends from a proximal end to a distal end thereof and has an elongate cylindrical shape. The distal end of the injection probe has a needle shape and is open for delivering the therapeutic moieties to the cells. The generator is configured to supply EP pulses at a plurality of waveforms to the array of EPEs, and configured to supply excitation signals at a plurality of waveforms to the array of EMEs. The EP device further comprises electrical connectors electrically connecting the array of EPEs and EMEs to the generator, and a switching mechanism between the electrical connectors and the generator.

In some embodiments, the EPEs and the EMEs are both configured as EPEs, i.e., the electrodes are all EPEs capable of switching between EP and Electrochemical Impedance Spectroscopy (EIS) modes. The generator is configured to supply the EPEs with EP pulses at the plurality of waveforms in the EP mode and with the excitation signals at the plurality of waveforms in the EIS mode, the measurement device is coupled to the EPEs, and the switching mechanism is adapted to switch the generator between the EIS and EP modes.

In accordance with some embodiments, an adaptive control method for controlling EP pulse parameters during electroporation (EP) of cells or tissue using an EP system, comprises a) providing any one of the EP devices described herein, b) initializing, by the initialization module, EP pulse parameters for performing the EP in the cells or tissue, the initialized EP pulse parameters based at least in part on the at least one trained model, c) applying, by the generator, the voltage and current excitation signals to the cells and tissue and measuring, by the measurement device, the voltage and current across the cells and tissue corresponding to the applied excitation signals, d) obtaining, by the controller, data from the current and voltage measurements, and processing the data to separate the desirable data from the undesirable data, e) extracting, by the controller, relevant features from the desirable data, f) applying, by the controller, at least a portion of the relevant features of the desirable data to the at least one trained diagnostic model, g) estimating, by the controller, EP pulsing parameters, based on an outcome of the applied relevant features to the trained models, wherein the initialized EP pulsing parameters are based on the at least one trained model and the relevant features, to optimize the EP pulsing parameters, and h) applying, by the generator, a first EP pulse based on the first pulsing parameters.

In some embodiments, the adaptive control method further comprises predicting subsequent EP pulsing parameters after the first EP pulse has been applied, by the controller, using the trained model based on a previous EP pulse, and a change in at least one of the relevant features between applied EP pulses.

In some embodiments, the adaptive control method further comprises generating a diagnostic response, by the controller, based at least in part on the applying. The diagnostic response comprises a) tissue detection, b) tumor type detection, c) needle placement detection, d) colocalization detection, and e) cell permeabilization detection.

In some embodiments, the adaptive control method further comprises f) applying a subsequent EP pulse, by the generator, based on the subsequent EP pulsing parameters, and g) repeating the applying the voltage and current excitation signals, repeating the measuring the cells or tissue, repeating the obtaining the data and separating desirable data from undesirable data; repeating the extracting relevant features; and repeating the applying, until either i) a predetermined limit of number of EP pulse sequences or cycles of EP pulses is reached, or ii) the diagnostic response prompts a diagnostic decision to terminate the adaptive control method.

In some embodiments, the adaptive control method further comprises storing the desirable data in the memory module.

In some embodiments, the at least one trained model is trained using empirical data observed during initial operation of an EP system using fixed EP pulse parameters.

In some embodiments, the adaptive control method further comprises determining dielectric and conductive properties of cells and tissues resulting from the applied excitation signals.

In some embodiments, the dielectric and conductive properties are determined by applying band-limited signals repeated over a fixed frequency range.

In some embodiments, the adaptive control method further comprises validating the current and voltage sensors of the measurement device, from which the measured data is obtained to assess quality of the data and the validating comprises statistically analyzing a quality of the measured data.

In some embodiments, the separating desirable data from undesirable data comprises at least one of a) de-noising the sensor signals, b) removing a direct current (DC) bias from the sensor signals, c) scaling the data based on standardized values, wherein the standardized values include standard deviation, d) mean filtering, and e) removing outliers from the data.

In some embodiments, the features are derived from a parametric model fit of magnitude and phase measurements of the voltage and current signals selected from the group comprising intracellular resistance, extracellular resistance, solution resistance, membrane capacitance, admittance, constant phase element exponent, and charging time constant.

In some embodiments, the parametric model fit of magnitude and phase measurements of the voltage and current signals of the excitation voltage and the current signals applied to the cells and tissue is determined by cross-correlating the excitation voltage and current signals with known reference signals stored in the memory module.

In some embodiments, dielectric and conductive properties of the cells or tissue are determined by the magnitude ratio and phase difference of the excitation voltage and current applied to of the cells or tissue.

In some embodiments, the features are derived from magnitude ratio or phase difference of the excitation voltage and current signals. The features comprise a) values of magnitude ratio and phase difference of the excitation voltage and current signals at fixed frequencies, b) at least one of a mean, median, maximum, and minimum of i) magnitude ratio or phase difference of the excitation voltage and current signals magnitude over a narrow frequency band, and ii) magnitude ratio or phase difference of the excitation voltage and current signals magnitude phase over a wide frequency band, and c) curvature, slope and noise of the magnitude ratio or phase difference of the excitation voltage and current signals with respect to frequency.

In accordance with some embodiments, a system for electroporation (EP) of cells in a tissue of a subject comprises a) an electroporation wand housing comprising i) an array of electroporation electrodes (EPEs); and ii) an array of electrochemical impedance spectroscopy (EIS) electrodes (EISEs), where the EPEs and EISEs are offset, b) an EP power supply configured to supply electric signals at a plurality of waveforms to the array of EPEs, c) an EIS power supply configured to supply electric signals at a plurality of waveforms to the array of EISEs, d) electrical connectors electrically connecting the array of EPEs to say EP power supply, and e) electrical connectors electrically connecting the array of EISEs to say EIS power supply, and f) an EIS sensor.

In accordance with some embodiments, the system further comprises a wand delivery system configured to deliver therapeutic moieties to the cells, the delivery system comprising at least one injection probe defining a first lumen, the injection probe extending from a proximal end to a distal end thereof and having an elongate cylindrical shape, wherein the distal end of the injection probe has a needle shape and is open for delivering the therapeutic moieties to the cells.

In accordance with some embodiments, a system for electroporation (EP) of cells in a tissue of a subject comprises a) an electroporation wand housing comprising an array of electrodes, b) an EP power supply configured to supply electric signals at a plurality of waveforms to the array of electrodes, c) an EIS power supply configured to supply electric signals at a plurality of waveforms to the array of electrodes, d) electrical connectors electrically connecting the array of electrodes to the EP power supply, e) electrical connectors electrically connecting the array of electrodes to the EIS power supply, f) a switching mechanism between the electrical connectors and the power supply, and g) an EIS sensor.

In some embodiments, the system according further comprises a wand delivery system configured to deliver therapeutic moieties to the cells, the delivery system comprising at least one injection probe defining a first lumen, the injection probe extending from a proximal end to a distal end thereof and having an elongate cylindrical shape, wherein the distal end of the injection probe has a needle shape and is open for delivering the therapeutic moieties to the cells.

In some embodiments, the electrodes are needles configured to penetrate skin and contact cells in the electric field zone.

In some embodiments, the electrodes are non-penetrating contacts.

In accordance with some embodiments, a method for electroporating cells of a tissue in a patient comprises a) providing any one of the EP systems described herein, b) inserting the electrodes into the tissue, c) applying at least one voltage pulse from the EIS power supply to the EIS electrodes to determine tissue parameters, d) calculating a voltage pulse to be used for electroporation using an electronic signal processing device, and e) applying at least one voltage pulse between a plurality of pairs of electrodes in the EP electrode array inserted in the tissue so as to establish an electric field in cells of the tissue sufficient to cause electroporation of cells in the tissue.

In some embodiments, the method further comprises a) providing a wand delivery system configured to deliver therapeutic moieties (TMs) to the cells, the delivery system comprising at least one injection probe defining a first lumen, the injection probe extending from a proximal end to a distal end thereof and having an elongate cylindrical shape, wherein the distal end of the injection probe has a needle shape and is open for delivering the therapeutic moieties to the cells, and b) delivering the TMs to the cells.

In some embodiments, the TM is delivered either prior to, simultaneously with, or after electroporation.

In some embodiments, the TM is injected locally into the tissue.

In some embodiments, the method is in vivo.

In some embodiments, the TM is a nucleic acid.

In some embodiments, the cells are tumor cells.

In some embodiments, the cells are melanoma or basal cell carcinoma cells.

In some embodiments, the electric field ranges from approximately 10 V/cm to about 2000 V/cm.

In some embodiments, a number of applied electrical pulses ranges from 1 to 100.

In some embodiments, duration of each electrical pulse ranges from about 10 s to about 100 ms in duration.

In some embodiments, at least one electrical pulse is selected from the group consisting of a square wave pulse, an exponential wave pulse, a unipolar oscillating wave form, and a bipolar oscillating wave form.

In some embodiments, each electrical pulse is comprised of a square wave pulse.

In accordance with some embodiments, a method of electroporating an agent into cells of a tissue, comprises a) introducing a therapeutic agent into a tissue of a patient in need of treatment, b) performing tissue impedance sensing to determine a suitable EP protocol, c) using an electrode apparatus placed in contact with the tissue to deliver voltage pulses that establish electric fields sufficient to introduce the therapeutic agent into cells of the tissue by way of electroporation, wherein the electrode apparatus comprises i) a support member having disposed thereon two or more opposing pairs of needle electrodes arranged relative to one another to form an electrode array, and ii) a power supply in electrical communication with pairs of needle electrodes disposed in the support member, wherein the power supply provides voltage pulses to at least two of the opposing pairs of needle electrodes to effect electroporation.

In some embodiments, a device for delivery of therapeutic moieties to cells in a treatment zone of a tissue comprises a) a central probe defining at least a central lumen and extending from a proximal end to a distal end, at least a portion of the central probe having a spiral geometry to create a channel for delivery of the therapeutic moieties to the tissue, the portion of the central probe having at least one ejection port positioned along the spiral geometry. The proximal end of the central probe is open and fluidly connects the first central lumen with a lumen of an injector through which the therapeutic agent is delivered to the central probe. The distal end of the central probe is open to define an opening for delivery of the therapeutic moieties into the tissue and has a shape configured to pierce the tissue. The device for delivery further comprises b) an applicator housing the central probe at least in part, the applicator having a distal end through which the portion of the central probe is configured to extend to an outside of the applicator to contact the tissue and to retract back into the applicator.

In some embodiments, the device further comprises at least one electrode pair positioned on the portion of the central probe.

In some embodiments, the distal end of the central probe is closed.

In some embodiments, at least one of a diameter of the first lumen of the central probe, an outer diameter, a spiral diameter and a pitch of the central probe are adjustable to change a distribution and volume of the delivered therapeutic moieties.

In some embodiments, the central probe is actuated to advance toward and through the distal end of the central probe and through the tissue.

In some embodiments, the device further comprises a) an electrical connector electrically connecting the central probe to a power source, and b) a handle housing the electrical connector and coupled to the applicator.

In some embodiments, the proximal end of the central probe is formed of or coated with a non-conductive material to prevent or reduce a generation of electrical fields at the portion.

In some embodiments, the device further comprises an electroporation system comprising at least two oppositely charged electroporation electrodes configured to be positioned surrounding the zone, the electrodes being adapted to extend from proximal to distal ends, tips of the distal ends having a needle shape configured to pierce the tissue. The electrodes are adapted to be coupled to an electrode power supply, receive at least one electrical waveform from the power supply, and supply a pulsed electric field sufficient for electroporation to the zone.

In some embodiments, the electrodes are housed at least in part in the applicator, positioned around the central probe and configured to be deployed from the applicator to surround the zone.

In some embodiments, the handle includes a power supply interface for supplying power from the power source to actuate the extending and retracting of the central probe, and to actuate extension and retraction of the electroporation electrodes.

In some embodiments, the device further comprises a sensor system configured to sense a capacitance of cell membranes. The sensor system comprises a) a pair of capacitance or EIS sensing electrodes powered by a low voltage power supply, b) a voltage sensor configured to sensor a voltage or voltage drop across the cell membranes, c) a current sensor configured to sense a current across the cell membranes, and d) an electronic signal processing device, configured to process the voltage drop and the current across the cell membranes and determine the capacitance of the cell membranes.

In some embodiments, the central probe is an electrode probe connected to the electrode power supply configured to generate an electric field between the central probe and the electroporation electrodes to facilitate electroporation.

In some embodiments, the device further comprises at least a second probe having defining at least a second lumen and extending from a proximal end to a distal end of the other probe, at least a portion of the other probe having a spiral geometry configured to create at least a second channel for delivery of the therapeutic moieties to the tissue. The proximal end of the other probe is open and fluidly connects the second lumen with a lumen of an injector through which the therapeutic agent is delivered to the other probe. The distal end of the other probe is open to define an opening for delivery of the therapeutic moieties into the tissue and has a shape configured to pierce the tissue. The other probe is housed in the applicator and the portion of the other probe is configured to extend to the outside of the applicator to contact the tissue and to retract back into the applicator.

In accordance with some embodiments, a device for delivery of therapeutic moieties to cells in a treatment zone of a tissue comprises a) a central probe defining at least a first lumen and extending from a proximal end to a distal end, at least a portion of the central probe having a spiral geometry configured to enhance anchoring of the central probe in the tissue and to create a channel for delivery of the therapeutic moieties to the tissue The portion of the central probe is formed of or coated with a conductive material. The proximal end of the central probe is open and fluidly connects the first lumen with a lumen of an injector through which the therapeutic agent is delivered to the central probe. The distal end of the central probe is open to define an opening for delivery of the therapeutic moieties into the tissue and has a shape configured to pierce the tissue. The device further includes b) an applicator housing the central probe, the applicator having a distal end through which the portion of the central probe is configured to extend to an outside of the applicator to contact the tissue and to retract back into the applicator, and c) at least one distal electrode positioned the distal end of the applicator and configured to generate an electric field with the portion of the central probe.

In some embodiments, the at least one distal electrode is configured based on a ring configuration, a straight wire configuration, a spiral wire configuration or a collapsible hoop configuration.

In some embodiments, the device further comprises at least one ejection port positioned on the portion of the central probe.

In some embodiments, the distal electrode is configured to be positioned external to the tissue.

In some embodiments, the distal electrode is configured to be positioned below a surface of the tissue.

In some embodiments, the distal electrode is formed of the spiral wire configuration, positioned below the surface of the tissue and spirals of the central probe and the distal electrode are wound in opposing directions.

In some embodiments, the device further comprises an electroporation system comprising at least two oppositely charged electroporation electrodes configured to be positioned surrounding the zone, the electrodes being adapted to extend from proximal to distal ends, tips of the distal ends having a needle shape configured to pierce the tissue. The electrodes are adapted to be coupled to an electrode power supply, receive at least one electrical waveform from the power supply, and supply a pulsed electric field sufficient for electroporation to the zone.

In some embodiments, the electrodes are housed in the applicator, positioned around the central probe and configured to be deployed from the applicator to surround the zone.

In some embodiments, the device further comprises a sensor system configured to sense a capacitance of cell membranes. the sensor system comprising a) a pair of capacitance sensing or EIS electrodes powered by a low voltage power supply, b) a voltage sensor configured to sense a voltage or voltage drop across the cell membranes, c) a current sensor configured to sense a current across the cell membranes, and d) an electronic signal processing device, configured to process the voltage drop and the current across the cell membranes and determine the capacitance of the cell membranes.

In some embodiments, the handle includes a power supply interface for supplying power from the power source to actuate the extending and retracting of the central probe, and to actuate extension and retraction of the electroporation electrodes.

In some embodiments, the device further comprises a sensor system configured to sense a capacitance of cell membranes. The sensor system comprises a) a pair of capacitance or EIS sensing electrodes powered by a low voltage power supply, b) a voltage sensor configured to sensor a voltage or voltage drop across the cell membranes, c) a current sensor configured to sense a current across the cell membranes, and d) an electronic signal processing device, configured to process the voltage drop and the current across the cell membranes and determine the capacitance of the cell membranes.

In accordance with some embodiments, a device for delivery of therapeutic moieties to cells in a treatment zone of a tissue comprises a) a central probe having an inner surface defining at least a first central lumen and extending from a proximal end to a distal end of the central probe, at least a portion of the central probe having a spiral geometry configured to enhance anchoring of the central probe in the tissue and to create a channel for delivery of the therapeutic moieties to the tissue, wherein the portion of the central probe is formed of or coated with a conductive material. The proximal end of the central probe is open and fluidly connects the central lumen with a lumen of an injector through which the therapeutic agent is delivered to the central probe. The distal end of the central probe is open to define an opening for delivery of the therapeutic moieties into the tissue and has a shape configured to pierce the tissue. The device further comprises b) an applicator housing the central probe, the applicator having a distal end through which the portion of the central probe is configured to extend to an outside of the applicator to contact the tissue and to retract back into the applicator, c) at least one straight probe having open proximal and distal ends for delivery of the therapeutic moieties to the tissue, and a vertical axis coaxially aligned with a center axis of a diameter of the central probe and configured to generate an electric field with the portion of the central probe.

In some embodiments, the device further comprises at least one ejection port positioned on the portion of the central probe.

In some embodiments, the spiral probe is configured to transmit acoustic energy received from an acoustic horn mounted to the distal end of the applicator.

In some embodiments, the device further comprises a sensor system configured to sense a capacitance of cell membranes, the sensor system comprising:

In some accordance with some embodiments, a method for delivery of therapeutic moieties to a treatment zone of a tissue comprises a) providing a device for delivery of therapeutic moieties to the treatment zone of the tissue. The device comprises i) a central probe and ii) and applicator. The central probe has at least a first central lumen and extends from a proximal end to a distal end, at least a portion of the central probe having a spiral geometry configured to enhance anchoring of the central probe in the tissue and to create a channel for delivery of the therapeutic moieties to the tissue. The portion of the central probe has a plurality of ejection ports positioned along the spiral geometry. The proximal end of the central probe is open and fluidly connects the central lumen with a lumen of an injector through which the therapeutic agent is delivered to the central probe. The distal end of the central probe is open to define an opening for delivery of the therapeutic moieties into the tissue and has a shape configured to pierce the tissue. The applicator houses the central probe and has a distal end through which the portion of the central probe is configured to extend to an outside of the applicator to contact the tissue and to retract back into the applicator. The method further comprises b) contacting the central probe to a diseased cell in the treatment zone of the tissue, c) actuating and extending the central probe from the applicator in an axial direction, d) piercing the tissue with at least a portion of the central probe and creating an opening through which at least a portion of the central probe enters the tissue to create a fluid channel for delivery of the therapeutic moieties to the tissue, and e) injecting the therapeutic moieties into the first central lumen and delivering the therapeutic moieties to the tissue through the at least one ejection port and the open distal end of the central probe.

In some embodiments, the method further comprises f) providing an electroporation system comprising at least two oppositely charged electroporation electrodes configured to be positioned surrounding the zone. The electroporation electrodes are adapted to extend from proximal to distal ends, tips of the distal ends have a needle shape, configured to pierce the tissue and the electroporation electrodes are adapted to be coupled to the power source. The method further comprises g) contacting the zone of the tissue with the electroporation electrodes, h) delivering an electric pulse to the electrodes from the power source, and i) applying a pulsed electric field to the zone which is sufficient for electroporation from the electroporation electrodes.

In some embodiments, the method further comprises providing a sensor system to sense a capacitance of cell membranes. The capacitance sensing comprises a) contacting the tissue with at least one pair of capacitance sensing electrodes powered by a low voltage power supply, b) transmitting, by the low voltage power supply, a low power interrogative signal to the at least one pair of capacitance sensing electrodes to produce low strength electric field excitations in the zone, c) sensing a voltage or voltage drop across the cell membranes by a voltage sensor, d) sensing a current across the cell membranes by a current sensor; and e) determining the capacitance of the cell membranes, based on the voltage drop and the current across the cell membranes, by an electronic signal processing device.

In accordance with some embodiments, a method for delivery of therapeutic moieties to a treatment zone of a tissue comprises a) providing a device for delivery of therapeutic moieties to the treatment zone of the tissue. The device comprises i) a central probe connected to a power source and having an inner surface defining at least a first central lumen and extending from a proximal end to a distal end of the central probe. At least a portion of the central probe has a spiral geometry configured to enhance anchoring of the central probe in the tissue and to create a channel for delivery of the therapeutic moieties to the tissue. The portion of the central probe is formed of or coated with a conductive material. The proximal end of the central probe is open and fluidly connects the central lumen with a lumen of an injector through which the therapeutic agent is delivered to the central probe. The distal end of the central probe is open to define an opening for delivery of the therapeutic moieties into the tissue and has a shape configured to pierce the tissue. The device further comprises ii) an applicator housing the central probe, the applicator having a distal end through which the portion of the central probe is configured to extend to an outside of the applicator to contact the tissue and to retract back into the applicator, and iii) at least one distal electrode positioned the distal end of the applicator, connected to the power source and configured to generate an electric field with the portion of the central probe. The method further comprises b) contacting the central probe and the distal electrode to a diseased cell in the treatment zone of the tissue, c) actuating and extending the central probe and the distal electrode from the applicator in an axial direction, d) piercing the tissue with the distal electrode and with at least a portion of the central probe and creating an opening through which at least a portion of the central probe enters the tissue to create a fluid channel for delivery of the therapeutic moieties to the tissue, e) injecting the therapeutic moieties into the first central lumen and delivering the therapeutic moieties to the tissue through the at least one ejection port and the open distal end of the central probe, f) delivering an electric pulse to the distal electrode and the central probe from the power source, g) applying a pulsed electric field to the zone which is sufficient for electroporation from the distal electrode and the central probe, and h) retracting the distal electrode and the central probe from the tissue.

In accordance with some embodiments, a device for delivery of therapeutic moieties to a zone of target cells of a tissue comprises a) a central probe defining at least a first lumen and having a proximal end and a closed distal end, a tip of the distal end having a needle shape configured to pierce tissue and having at least one exit port positioned at a predetermined position from the distal end, the exit port fluidly connecting the first lumen to an outside of the central probe, and b) at least one channeling wire positioned in the first lumen and slidable within the central probe, the channeling wire having a proximal end positioned in the central probe and a distal end configured to extend to an outside of the central probe and retract back into the first lumen through the exit port, a tip of the distal end of the channeling wire having a shape configured to pierce through the tissue and define an opening through which at least a portion of the channeling wire enters the tissue to create a fluid channel through which the therapeutic moieties are delivered to the tissue. The therapeutic moieties are delivered from the first lumen into the channel through the exit port. The device further comprises c) a ramp integrally formed with or coupled to the first lumen, the ramp configured to contact and guide the channeling wire to exit the central probe to the outside of the central probe, d) an electrical connector electrically connecting the central probe and channeling wire to a power source, e) a small bore connector connecting the central probe to a syringe for delivery of the therapeutic moieties, and f) a handle housing the electrical connector at least in part and coupled to proximal ends of the central probe and the channeling wire to facilitate a depth of penetration of the distal ends of the central probe and the channeling wire.

In some embodiments, the device further comprises an electroporation system comprising at least two oppositely charged electrodes configured to be positioned surrounding the zone of target cells, the electrodes being adapted to extend from proximal to distal ends, tips of the distal ends having a needle shape, configured to pierce the tissue wherein the electrodes are adapted to be coupled to the power source, receive an electrical waveform from the power supply, and supply a pulsed electric field sufficient for electroporation to the zone of target cells.

In some embodiments, electrodes surround the central probe.

In some embodiments, the device comprises a plurality of the exit ports and a plurality of the channeling wires configured to simultaneously extend to the outside of the central probe and configured to retract back into the central lumen of the central probe through the exit ports.

In some embodiments, the handle includes a power supply interface for supplying power from the power source to actuate the extending and retracting of the channeling wire, and to actuate extension and retraction of the electrodes.

In some embodiments, the device further comprises a catheter shaft surrounding an outer surface of the central probe to support and protect the central probe during insertion into a body having the tissue.

In some embodiments, the channeling wire includes a cutting blade at the tip of the distal end of the channeling wire.

In some embodiments, the cutting blade at the distal end is configured to enter the tissue and is configured to rotate about a central axis of the cutting blade to form the fluid channel.

In some embodiments, an angle at which the ramp contacts the channeling wire is adjustable to vary a trajectory angle of the channeling wire exiting the central lumen.

In accordance with some embodiments, a device for delivery of therapeutic moieties to a zone of target cells of a tissue comprises a) a central probe defining at least a first lumen and having a proximal end and an open distal end, a tip of the distal end having a needle shape configured to pierce the tissue and the open distal end fluidly connecting the first lumen to an outside of the central probe, b) at least one channeling wire positioned in the first lumen, and slidable within the central probe, and having a proximal end positioned in the central probe and a distal end configured to extend to an outside of the central probe and retract back into the central lumen through the distal end of the central probe, the channeling wire comprising a super-elastic material configured to be heat set with a curve, wherein the channeling wire is adapted to be elastically straightened when positioned in the central lumen, and adapted to be curved with the curve when extended to the outside of the central probe to form a channel extending to the cells, the channeling wire having an elongate cylindrical shape and the distal end thereof further configured to pierce through the tissue and define an opening through which at least a portion of the channeling wire enters the tissue to create a fluid channel through which the therapeutic moieties are delivered to the tissue. The therapeutic moieties are delivered from the first lumen into the channel through the exit port. The device further comprises b) a ramp integrally formed with or coupled to an inner surface of the central probe, the ramp configured to contact and guide the channeling wire to exit the central probe to the outside of the central probe, c) an electrical connector electrically connecting the central probe and channeling wire to a power source, d) a small bore connector connecting the central probe to a syringe for delivery of the therapeutic moieties, and e) a handle housing the electrical connector at least in part and coupled to proximal ends of the central probe, and the channeling wire to facilitate a depth of penetration of the distal ends of the central probe and the channeling wire.

In some embodiments, the super-elastic material is any one or a combination of materials selected from a group comprising NiTi, Cu—Al—Ni, Fe—Mn—Si, NiTi—Zr, Cu—Zr, Ni—Al and Cu-based alloy.

In some embodiments, the device comprises a plurality of the exit ports and a plurality of the channeling wires configured to simultaneously extend to the outside of the central probe and configured to retract back into the central lumen of the central probe through the exit ports.

In some embodiments, the device further comprises at least two oppositely charged electrodes configured to be positioned surrounding the zone of target cells for treatment of the cells, the electrodes being adapted to extend from proximal to distal ends, tips of the distal ends having a needle shape, configured to pierce the tissue, wherein the electrodes are adapted to be coupled to the power source, receive an electrical waveform from the power supply, and supply a pulsed electric field sufficient for electroporation to the target tissue region.

In some embodiments, the handle includes a power supply interface for supplying power from the power source to actuate the extending and retracting of the channeling wire, and to actuate extension and retraction of the electrodes.

In some embodiments, the device further comprises a catheter shaft surrounding an outer surface of the central probe to support and protect the central probe during insertion into a body having the tissue.

In accordance with some embodiments, a device for delivery of therapeutic moieties to a zone of target cells of a tissue comprises a) an injection probe defining at least a first lumen, the injection probe extending from a proximal end to a distal end thereof and having an elongate cylindrical shape, the distal end having a needle shape and being open for delivering the therapeutic moieties to the zone, b) a central probe coupled to the injection probe and having an inner surface defining at least a second lumen, the central probe having a proximal end and a closed distal end, a tip of the distal end having a needle shape configured to pierce tissue and having at least one exit port positioned at a predetermined distance between the distal and proximal ends of the central probe, the exit port fluidly connecting the second lumen to an outside of the central probe, c) at least one channeling wire positioned in the second lumen and slidable within the central probe, the channeling wire having a proximal end positioned in the central probe and a distal end configured to extend to an outside of the central probe and retract back into the second lumen through the exit port, a tip of the distal end of the channeling wire having a shape configured to pierce through the tissue and define an opening through which at least a portion of the channeling wire enters the tissue to create a fluid channel through which the therapeutic moieties are injected into the zone by the injection probe, d) a ramp integrally formed with or coupled to an inner surface of the central probe defining the inner surface of second lumen, and the ramp configured to contact and guide the channeling wire to exit the central probe to the outside of central probe, e) an electrical connector electrically connecting the central probe and channeling wire to a power source, and f) a handle housing the electrical connector at least in part and coupled to the proximal end of the central probe and the proximal end of the injection probe, and the channeling wire to facilitate a depth of penetration of the distal ends of the injection probe and central probe.

In some embodiments, the device comprises a plurality of the exit ports and a plurality of the channeling wires configured to simultaneously extend to the outside of the central probe and configured to retract back into the central lumen of the central probe through the exit ports.

In some embodiments, the device further comprises at least two oppositely charged electrodes configured to be positioned surrounding a target tissue region for treatment of the cells, the electrodes being adapted to extend from proximal to distal ends, tips of the distal ends having a needle shape, configured to pierce the tissue, wherein the electrodes are adapted to be coupled to the power source, receive an electrical waveform from the power supply, and supply a pulsed electric field sufficient for electroporation to the target tissue region.

In some embodiments, an angle at which the ramp contacts the channeling wire is adjustable to vary a corresponding trajectory angle of the channeling wire exiting the second lumen.

In accordance with some embodiments, a method for delivery of therapeutic moieties to a zone of target cells in a tissue comprising a) providing a device for delivery of therapeutic moieties to a zone of target cells of a tissue. The device comprises i) a central probe having an inner surface defining at least a first central lumen and having a proximal end and a closed distal end, a tip of the distal end having a needle shape configured to pierce tissue and having at least one exit port positioned at a predetermined position from the distal end, the exit port fluidly connecting the central lumen to an outside of the central probe, ii) at least one channeling wire positioned in the central lumen and slidable within the central probe, the channeling wire having a proximal end positioned in the central probe and a distal end configured to extend to an outside of the central probe and retract back into the central lumen through the exit port. A tip of the distal end of the channeling wire has a shape configured to pierce through the tissue and define an opening through which at least a portion of the channeling wire enters the tissue to create a fluid channel through which the therapeutic moieties are delivered to the tissue. The therapeutic moieties are delivered from the first central lumen into the channel through the exit port. The device further comprises iii) a ramp integrally formed with or coupled to the inner surface of the central probe, the inner surface defining the central lumen, and the ramp configured to contact and guide the channeling wire to exit the central probe to the outside of the central probe, iv) an electrical connector electrically connecting the central probe and channeling wire to a power source, v) a small bore connector connecting the central probe to a syringe for delivery of the therapeutic moieties, vi) a handle housing the electrical connector and coupled to proximal ends of the central probe and the channeling wire to facilitate a depth of penetration of the distal ends of the central probe and the channeling wire. The method further comprises b) inserting the central probe into a diseased cell in the zone of target cells, c) actuating and extending the channeling wire from the central lumen in an axial direction of the central probe, the tip of the distal end of the channeling wire having the needle shape piercing through the tissue and making an opening through which at least a portion of the channeling wire enters the tissue and creates a fluid channel through which the therapeutic moieties are delivered, d) actuating the ramp which is integrally formed with or coupled to the inner surface of the central probe, the ramp contacting the channeling wire and guiding a trajectory of the channeling wire through the exit port towards a distal end of the central probe, the exit port fluidly connecting the central lumen with an outside of the central probe, e) piercing the tissue with the channeling wire and creating an opening through which at least a portion of the channeling wire enters the tissue to create a fluid channel for delivery of the therapeutic moieties to the tissue, f) retracting the channeling wire back into the central lumen, and g) injecting the therapeutic moieties into the central lumen and delivering the therapeutic moieties to the tissue through the fluid channel.

In some embodiments, the method further comprises a) rotating the device for delivery at least once and piercing the tissue with the channeling wire to create additional fluid channels for delivery of the therapeutic moieties to the tissue before the injecting of the therapeutic moieties and the delivering of the therapeutic moieties to the tissue through the fluid channel.

In some embodiments, the method further comprises a) providing an electroporation system comprising at least two oppositely charged electroporation electrodes configured to be positioned surrounding the zone of target cells, in which the electroporation electrodes are adapted to extend from proximal to distal ends, tips of the distal ends have a needle shape configured to pierce the tissue, and the electroporation electrodes are adapted to be coupled to the power source, b) contacting the zone of target cells with the electroporation electrodes, c) delivering an electric pulse to the electrodes from the power source, and d) applying a pulsed electric field to the zone of target cells which is sufficient for electroporation from the electroporation electrodes.

In accordance with some embodiments, a method for delivery of therapeutic moieties to a zone of target cells in a tissue comprises a) providing a device for delivery of therapeutic moieties to the zone of target cells of the tissue. The device comprises a) an injection probe defining at least a first lumen, the injection probe extending from a proximal end to a distal end thereof and having an elongate cylindrical shape, the distal end having a needle shape and being open for delivering the therapeutic moieties to the zone, b) a central probe coupled to the injection probe and having an inner surface defining at least a second lumen, the central probe having a proximal end and a closed distal end, a tip of the distal end having a needle shape configured to pierce tissue and having at least one exit port positioned at a predetermined distance between the distal and proximal ends of the central probe, the exit port fluidly connecting the second lumen to an outside of the central probe, c) at least one channeling wire positioned in the second lumen and slidable within the central probe, the channeling wire having a proximal end positioned in the central probe and a distal end configured to extend to an outside of the central probe and retract back into the second lumen through the exit port, a tip of the distal end of the channeling wire having a shape configured to pierce through the tissue and define an opening through which at least a portion of the channeling wire enters the tissue to create a fluid channel through which the therapeutic moieties are injected into the zone by the injection probe, d) a ramp integrally formed with or coupled to an inner surface of the central probe defining the inner surface of second lumen, and the ramp configured to contact and guide the channeling wire to exit the central probe to the outside of central probe, e) an electrical connector electrically connecting the central probe and channeling wire to a power source, and f) a handle housing the electrical connector at least in part and coupled to the proximal end of the central probe and the proximal end of the injection probe, and the channeling wire to facilitate a depth of penetration of the distal ends of the injection probe and central probe. The method further comprises b) inserting the central probe into a diseased cell in the zone of target cells, c) actuating and extending the channeling wire from the central lumen in an axial direction of the central probe, the tip of the distal end of the channeling wire having the needle shape piercing through the tissue and making an opening through which at least a portion of the channeling wire enters the tissue and creates a fluid channel through which the therapeutic moieties are delivered, d) actuating the ramp which is integrally formed with or coupled to the inner surface of the central probe, the ramp contacting the channeling wire and guiding a trajectory of the channeling wire through the exit port towards a distal end of the central probe, the exit port fluidly connecting the central lumen with an outside of the central probe, e) piercing the tissue with the channeling wire and creating an opening through which at least a portion of the channeling wire enters the tissue to create a fluid channel for delivery of the therapeutic moieties to the tissue, f) retracting the channeling wire back into the central lumen, g) injecting the therapeutic moieties into the central lumen and delivering the therapeutic moieties to the tissue through the fluid channel.

The method further comprises a) rotating the device for delivery at least once and piercing the tissue with the channeling wire to create additional fluid channels for delivery of the therapeutic moieties to the tissue before the injecting of the therapeutic moieties and the delivering of the therapeutic moieties to the tissue through the fluid channel.

The method further comprises a) providing an electroporation system comprising at least two oppositely charged electroporation electrodes configured to be positioned surrounding the zone of target cells, in which the electroporation electrodes are adapted to extend from proximal to distal ends. Tips of the distal ends have a needle shape, configured to pierce the tissue. The electroporation electrodes are adapted to be coupled to the power source. The method further comprises b) contacting the zone of target cells with the electroporation electrodes, c) delivering an electric pulse to the electrodes from the power source, and d) applying a pulsed electric field to the zone of target cells which is sufficient for electroporation from the electroporation electrodes.

In accordance some embodiments, a system for electroporation of cells in an electroporation location of an electric field zone in a tissue in a subject comprises a) an electroporation wand housing. The housing comprises i) a first pair of electroporation electrodes, and ii) at least a second pair of electroporation electrodes housed in the wand housing, the first and second pairs of electroporation electrodes configured to be oppositely charged, offset from each other at a predetermined angle, and configured to define an outer periphery of the electric field zone. The system further comprises b) a power supply configured to supply electric signals at a plurality of waveforms to the first and second pairs of electroporation electrodes, and c) an electrical connector electrically connecting each of the first and second pairs of electroporation electrodes to the power supply.

In some embodiments, the system further comprises a wand delivery system configured to deliver therapeutic moieties to the electroporation location, the delivery system comprising at least one injection probe defining a first lumen, the injection probe extending from a proximal end to a distal end thereof and having an elongate cylindrical shape, wherein the distal end of the injection probe has a needle shape and is open for delivering the therapeutic moieties to the electroporation location.

In some embodiments, the system comprises two pairs of electroporation electrodes and the angle is about 90 degrees.

In some embodiments, the first pair of electroporation electrodes is configured to receive a first electric signal represented by a first waveform from the power supply, and the second pair of electroporation electrodes are configured to receive a second electric signal represented by a second waveform from the power supply.

In some embodiments, the first and second pairs of electroporation electrodes are needles configured to penetrate skin and contact cells in the electric field zone.

In some embodiments, the first and second pairs of electroporation electrodes are non-penetrating contacts.

In accordance with some embodiments, a method for electroporating cells in an electroporation location of an electric field zone in a tissue in a subject comprises a) providing an electroporation system comprising i) an electroporation wand housing comprising 1) a first pair of electroporation electrodes, and 2) at least a second pair of electroporation electrodes housed in the wand housing, the first and second pairs of electroporation electrodes oppositely charged, offset from each other at a predetermined angle, and configured to define an outer periphery of the electric field zone, ii) a power supply configured to supply electric signals at a plurality of waveforms to the first and the at least second pairs of electroporation electrodes, and iii) an electrical connector electrically connecting the pair of electroporation electrodes to the power supply. The method further comprises b) contacting the electroporation wand housing to the tissue, such that the electric field zone is between the pairs of electroporation electrodes, c) applying a first signal from the power supply to the first pair of electroporation electrodes at a first waveform and applying a second signal from the power supply to the second pair of electroporation electrodes at a second waveform, wherein the first waveform has a predetermined phase difference from the second waveform, d) applying a pulsed electric field to the electric field zone from the first pair of electroporation electrodes, the pulsed electric field being based on the first signal, wherein the pulsed electric field and each subsequent pulsed electric field of the first pair of electroporation electrodes have a voltage and duration lower than a minimum threshold for electroporation, e) applying another pulsed electric field to the electric field zone from the second pair of electroporation electrodes, the other pulsed electric field being based on the second signal, where the other pulsed electric field and each subsequent pulsed electric field of the second pair of electroporation electrodes have a voltage and duration lower than a minimum threshold for electroporation. Paths of the pulsed electric fields of the first and second pairs of electroporation electrodes cross at the electroporation location, and the application of each pulsed electric field of the first pair of electroporation electrodes to the electroporation location alternates with the application of each pulsed electric field of the second pair of electroporation electrodes to the electroporation location to amount to a continuous pulsed electric field having a voltage and duration sufficient for electroporation to be applied to the cells in the electroporation location. The application of each pulsed electric field of the first pair of electroporation electrodes to tissue adjacent to the first pair of electroporation electrodes and outside of the electroporation location alternates with a rest period to cause the tissue adjacent to the first pair of electroporation electrodes and outside of the electroporation location to receive an alternating on and off pulsed electric field of the first pair of electroporation electrodes having the voltage and duration lower than the minimum threshold for electroporation. The application of each pulsed electric field of the second pair of electroporation electrodes to tissue adjacent to the second pair of electroporation electrodes and outside of the electroporation location alternates with a rest period to cause the tissue adjacent to the second pair of electroporation electrodes and outside of the electroporation location to receive an alternating on and off pulsed electric field of the second pair of electroporation electrodes having the voltage and duration lower than the minimum threshold for electroporation.

In some embodiments, the method further comprises delivering therapeutic moieties to the electroporation location by a wand delivery system, comprising at least one injection probe defining a first lumen, the injection probe extending from a proximal end to a distal end thereof and having an elongate cylindrical shape. The distal end of the injection probe has a needle shape and is open for delivering the therapeutic moieties to the electroporation location.

In some embodiments, the method further comprises providing a sensor system to sense a capacitance of cell membranes. The capacitance sensing comprises a) contacting the tissue with at least one pair of capacitance sensing electrodes powered by a low voltage power supply, b) transmitting, by the low voltage power supply, a low power interrogative signal to the at least one pair of capacitance sensing electrodes to produce low strength electric field excitations in the electroporation location, c) sensing a voltage or voltage drop across the cell membranes by a voltage sensor, d) sensing a current across the cell membranes by a current sensor, and e) determining the capacitance of the cell membranes, based on the voltage drop and the current across the cell membranes, by an electronic signal processing device.

In some embodiments, the capacitance of the cell membranes is determined prior to applying the pulsed electric fields, and between the pulsed electric fields.

In some embodiments, the method further comprises, upon determination of the capacitance of the cell membranes between the pulsed electric fields, adjusting pulse width of the pulsed electric fields based on time constants associated with the membrane capacitance.

In some embodiments, the first and second waveforms have a same wavelength.

In some embodiments, the voltage of the power supply is variable from about 50V to 1000V.

In some embodiments, each pulsed electric field of the first and second electrode pairs has a pulse width variable from 1 µs to 1 ms.

In some embodiments, each pair of electroporation electrodes fire each pulsed electric field for a time period of 1/(no. of electrode pairs) of the period of the wavelength of each corresponding waveform.

In some embodiments, the cells are selected from a group consisting of a pancreas, a larynx, a pharynx, a lip, a throat, a lung, a kidney, a muscle, a breast, a colon, a uterus, a prostate, a thymus, a testis, a skin, and an ovary cell.

In some embodiments, the cells are prostate tumor cells.

In some embodiments, the cells are mammalian cells.

In some embodiments, the cells are human cells.

In some embodiments, the pulsed electric fields of the first and second pairs of electroporation electrodes ranges from about 200 to 500 mV.

In some embodiments, the pulsed electric fields of the first and the second pairs of electroporation electrodes are applied as from about 1 to about 5 electrical pulses.

In some embodiments, the first and second pulsed electric fields are selected from a group consisting of a square wave pulse, an exponential wave pulse, a unipolar oscillating wave form of limited duration, and a bipolar oscillating wave form of limited duration.

In some embodiments, the first and second pulsed electric fields comprise a square wave pulse.

In some embodiments, the therapeutic moieties are selected from the group consisting of a nucleic acid, a polypeptide, and a chemotherapeutic agent.

In some embodiments, the chemotherapeutic agent is selected from a group consisting of Bleomycin, Cisplatin, and Mitomycin C.

In some embodiments, the electroporation wand housing consists of a non-conductive fixture.

In some embodiments, the non-conductive fixture is made of plastic.

In some embodiments, each pair of electroporation electrodes determines a field vector and a current path of the corresponding electric field.

In some embodiments, the first and second waveforms have a predetermined phase difference.

In accordance with some embodiments, a system for electroporation (EP) of cells in a tissue of a subject comprises a) a trocar and b) an EP device. The trocar comprises i) a cannula extending from a proximal end to an open distal end and defining a first lumen configured to receive an obturator, and ii) the obturator extending from a proximal end to a distal end, the proximal end including a handle mounted thereon, the distal end including a blade configured to pierce through skin, penetrate into body cavities and form a path through which the cannula may be at least partially inserted into the cavity. The obturator is configured to be slidable within the first lumen, the distal end of the obturator configured to extend to an outside of the first lumen through the open distal end of the cannula. The EP device is slidably mountable and retractable within the cannula to access cancerous cells and comprises i) an anchor extending from a proximal to a distal end, ii) at least two oppositely charged electrodes retractably disposed at the distal end of the anchor and configured to be positioned surrounding a zone of target cells. The electrodes are adapted to be coupled to a generator, receive at least one electrical waveform from the generator, and supply at least one of an excitation signal and an EP pulse. The Ep device further comprises iii) a central probe retractably disposed at the distal end of the anchor and having an inner surface defining at least a central lumen and extending from the distal end of the anchor, at least a portion of the central probe having a spiral geometry configured to enhance anchoring of the central probe in the tissue and to create a channel for delivery of the therapeutic moieties to the tissue. The distal end of the central probe is open to define an opening for delivery of the therapeutic moieties into the tissue and has a shape configured to pierce the tissue.

In some embodiments, the blade of the obturator is configured to extend to an outside of the cannula through an opening at the distal end of the cannula In some embodiments, the EP device electrodes are adapted to extend from proximal to distal ends, tips of the distal ends having a needle shape, configured to pierce the tissue. The electrodes are adapted to be coupled to a power supply, receive an electrical waveform from the power supply, and supply at least one of an excitation signal and an EP pulse to the zone of target cells.

In some embodiments, an adaptive control method for controlling EP pulse parameters during electroporation (EP) of cells or tissue using an EP system comprises a) providing any of the systems for providing adaptive control to optimize electroporation (EP) pulse parameters during EP of cells and tissue using any of the EP device described herein, b) initializing, by the initialization module, EP pulse parameters for performing the EP in the cells or tissue, the initialized EP pulse parameters based at least in part on the at least one trained model, c) applying, by the generator, the voltage and current excitation signals to the cells and tissue and measuring, by the measurement device, the voltage and current across the cells and tissue corresponding to the applied excitation signals, d) obtaining, by the controller, data from the current and voltage measurements, and processing the data to separate the desirable data from the undesirable data, e) extracting, by the controller, relevant features from the desirable data, f) applying, by the controller, at least a portion of the relevant features of the desirable data to the at least one trained diagnostic model, g) estimating, by the controller, EP pulsing parameters, based on an outcome of the applied relevant features to the trained models, wherein the initialized EP pulsing parameters are based on the at least one trained model and the relevant features, to optimize the EP pulsing parameters, h) applying, by the generator, a first EP pulse based on the first pulsing parameters.

In some embodiments, the method further comprises predicting subsequent EP pulsing parameters after the first EP pulse has been applied, by the controller, using the trained model based on a previous EP pulse, and a change in at least one of the relevant features between applied EP pulses.

In some embodiments, the method further comprising generating a diagnostic response, by the controller, based at least in part on the applying, where the diagnostic response includes a) tissue detection, b) tumor type detection, c) needle placement detection, d) colocalization detection, and d) cell permeabilization detection.

In some embodiments, the method further comprises a) applying a subsequent EP pulse, by the generator, based on the subsequent EP pulsing parameters, and b) repeating the applying the voltage and current excitation signals, repeating the measuring the cells or tissue, repeating the obtaining the data and separating desirable data from undesirable data, repeating the extracting relevant features; and repeating the applying, until either i) a pre-determined limit of number of EP pulse sequences or cycles of EP pulses is reached, or ii) the diagnostic response prompts a diagnostic decision to terminate the adaptive control method.

BRIEF DESCRIPTION OF THE DRAWINGS

FIG. 3 depicts a schematic for EIS determinations using 4 EP and 4 EME electrodes. FIG. 3 depicts a top view of the electrodes of the device inserted into a hypothetical tissue that includes a blood vessel and an irregularly shaped tumor (note that EM can find use in non-penetrating electrode devices as well). For non-limiting exemplary purposes, two sets of electroporation electrodes (EPEs) and two sets of electrochemical impedance spectroscopy electrodes (EMEs) are shown although other numbers and geometries are contemplated. These electrode sets are shown basically equidistant in FIG. 3, although as will be appreciated by those in the art, any number of sets can be used in conforming with the present invention.

FIGS. 4A and 4B show two embodiments utilizing insertion EP electrodes with insulative materials for the creation of different electrical field zones (for simplicity, only a single pair of electrodes is shown). FIG. 4A shows a single pair of electrodes, with alternating areas of insulative material and bare electrodes; stated differently, the electrodes have conductors alternating evenly spaced along the length of the electrode, where each conductor is separated by insulating materials. FIG. 4B shows a similar set, but in this case each conductor is not evenly spaced, such that asymmetrical electric fields can be generated.

FIGS. 6A, 6B and 6C depict three different configurations of EPEs and EMEs. In FIG. 6C, a single set of electrodes are used, that are connected via a switching mechanism to the respective EPE and EME power sources. The switching mechanism switches on and off when a small excitation voltage is applied across its control terminals. These switches use coupling mechanisms which include electromagnetic, electromechanical, piezoelectric and photoelectric mechanisms. In FIG. 6A, two sets of electrodes are used, EPEs and EMEs, and each is configured and connected to the appropriate power source. FIG. 6B is similar, except that the EPEs and EMEs are offset from each other at a predetermined angle, depending on the number of each electrode type to be used. In this embodiment, the tissue in the zone can be interrogated in different ways. For example, the tissue right against the EPEs can suffer damage (e.g. the tissue is in a "kill zone"). In FIG. 6B, measuring impedance (including capacitance) between EME #1 and EME #2 can help determine the tissue damage at EPE #1, for example, or alternatively could be used in a sort of "electronic tumor tomography", as is more fully described in relation to EM, below.

FIGS. 7A, 7B, 7C and 7D depict different EPE configurations, although only a single pair of electrodes are depicted for simplicity. FIG. 7A depicts one set of non-penetrating solid EPEs, applied topically to the surface of the skin. Additional sets of EPEs are not shown, but are included.

FIG. 7B depicts one set of solid EPEs that are penetrating into the tissue; in this embodiment, the tip of the EPEs is generally pointed to facilitate insertion into the tissue, such as a solid needle tip. In this embodiment, the electric field zone is "deeper" in the tissue, e.g. below the surface. This results in a three dimensional electric field along the length and radial dimensions between the electrodes. In general, these penetrating EPEs can be from about 1 to about 20 mm, depending on the geometry and physiology of the tissue to be treated. In FIG. 7C, the penetrating solid EPEs are coated with an insulating (non-conductive) material, such that only a distal portion of the electrode is exposed. In the embodiments of FIGS. 7A, 7B and 7C, the TM delivery system will generally be a needle that is shallowly inserted into the EP location between the EPEs (not shown). In FIG. 7D, the penetrating EPEs are hollow, with a lumen for TM delivery and a pointed, open tip connected to the lumen. On the left hand side, the penetrating electrode has a portion along the axis which is coated with an insulating material. As will be appreciated by those in the art, when capacitance measurements are done, the EPEs can either be used as electrical measurement electrodes (EMEs) or there can be separate set(s) of EMEs, as generally depicted in FIG. 6.

FIGS. 8A, 8B, 8C and 8D depict components of the EP device of the invention (all of which rely on cylindrical needles, although other geometries can be used as well; also, only a single pair of EP electrodes is depicted). FIGS. 8A and 8B depict one set of EPEs (second set not shown) with a TM delivery (TMD) system. FIG. 8A shows the EPEs and TM delivery system inserted into the tissue, with the TMD hollow need with an open end, a lumen for delivering the TM, and the TM whimsically being delivered. FIG. 8B shows the underside of the device, which may be in the distal end of the wand. Alternatively, as shown in FIG. 8C, the TMD system may comprise a standard syringe, inserted manually by the administering physician during the procedure. In this embodiment, the syringe may have an optional needle stop to physically prevent deeper penetration, at a depth that correlates with the depth of the electric field zone. FIG. 8D depicts a TM delivery needle that has multiple openings to delivery TMs. This may be of use when larger biological molecules such as plasmids and antibodies are delivered, as in general, larger molecules (which are additionally usually charged) diffuse more slowly in tissue than other molecules. Thus having multiple delivery loci within the EP location can serve to have a higher percentage of cells in a zone take up the TMs. FIG. 8D depicts three openings or ports, although any number can be used. In addition, FIG. 8D depicts the openings on one "side" of the needle, but openings can be located on any part of the outer surface of the needle, forming spirals or other shapes.

FIG. 17A is a schematic illustration of an exemplary EP device with electrodes integrated around a centralized injection element and centralized moiety delivery probe for use in the adaptive control system for optimizing electroporation (EP) pulse parameters, and FIG. 17B is a bottom view of the EP device.

FIG. 22A, FIG. 22B, and FIG. 22C are schematic views of an EP device having distal electrode and a central probe according to the present invention.

In FIG. 34A, a plurality of channel wires are used, all deployed at once, creating a "starburst" pattern. In FIG. 34B, a single channel wire is used, that is deployed, retracted, rotated and re-deployed, creating the same "starburst" pattern but sequentially. In FIG. 34C, a single channel wire is used but after deploying and retracting the channel wire, the wand housing is withdrawn slightly and the channel wire is deployed again, forming a "comb" structure.

FIG. 49 illustrates a table.

DETAILED DESCRIPTION OF THE INVENTION

I. Overview

Figure 1:
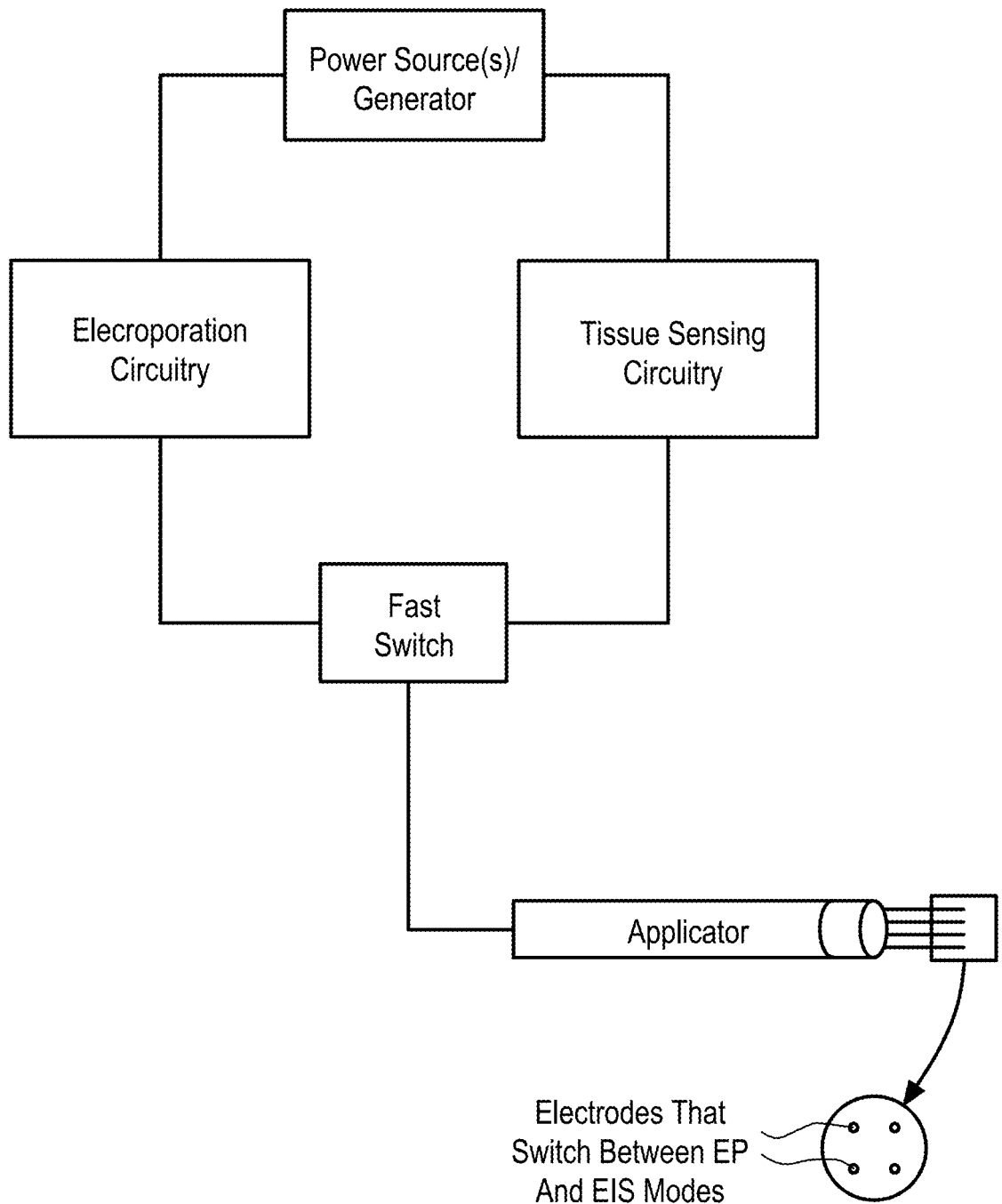
FIG. 1 is simple schematic depicting some of the components of an EP device used to apply electric pulses for EIS according to the present invention.

The present invention is generally directed to devices, systems and methods useful in the controlling of electroporation (EP) pulsing parameters for improvement and ideally optimization of EP of cells and tissues of a patient. As further described herein, there are a variety of uses for the invention, including, but not limited to, for example, the ability to insert therapeutic moieties (including small molecule drugs, plasmids encoding therapeutic proteins, etc.) into cells. The invention finds particular use in oncology applications. The invention allows suitable EP conditions and/or an EP protocol to be determined in real time, using electrical measurements (EM), including but not limited to electrochemical impedance spectroscopy (EIS). The present invention aims to improve EP processes by integrating feedback control mechanisms. Thus, the systems and methods of the invention can be used with any EP devices/applicators and any methods such as those outlined in U.S. Provisional Patent Application Nos. 62/214,807, 62/214,872, 62/141,142, 62/141,182, 62/141,256, and 62/141,164, all of which are expressly incorporated by reference in their entirety, specifically including the Figures, Legends and descriptions of the Figures and components therein.

EP parameters currently used in clinical trials are empirically established in preclinical mouse studies using homogeneous syngeneic tumor models. Commonly, electrical parameters are selected that give the highest rise in mean expression of the electroporated nucleic acid over injection alone. Previous studies in the field have analyzed the effects of pDNA concentration, electric field (e-field) strength, pulse width, tissue type, electrical conditions, injection volume, molecule of interest, concentration, and applicator geometry on expression. It has been determined that each of the aforementioned parameters significantly impacted the resulting expression.

To maximize the efficacy of EP, a quantifiable metric of membrane integrity that is measurable in real-time is desirable. Electrochemical impedance spectroscopy (EIS) is a method for the characterization of physiologic and chemical systems and can be performed with standard EP electrodes. This technique measures the electrical response of a system over a range of frequencies to reveal energy storage and dissipation properties. In biologic systems the extracellular and intracellular matrix resist current flow and therefore can be electrically represented as resistors. The lipids of intact cell membranes and organelles store energy and are represented as capacitors. Electrical impedance is the sum of these resistive and capacitive elements over a range of frequencies. To quantify each of these parameters, tissue impedance data can be fit to an equivalent circuit model. Real-time monitoring of electrical properties of tissues will enable feedback control over EP parameters and lead to optimum transfection in heterogeneous tumors. Using EIS feedback, will allow (1) delivery parameters to be adjusted in real-time, (2) delivery of only the pulses necessary to generate a therapeutic response, and (3) reduce the overall EP-mediated tissue damage as a result.

Various embodiments of the present invention are directed to providing closed-loop EP control systems using tissue-sensing based feedback to optimize the EP process with tumor-specific measurements acquired before and between each EP pulse. Tissue sensing is used to measure the membrane charge time for a specific tumor to tailor each EP pulse for optimal treatment.

As will be appreciated by those in the art, successful EP occurs when the cellular membrane is disrupted, resulting in a change of capacitance. Thus, by monitoring and measuring electrical properties, e.g. impedance (including capacitance) before, during and/or after the EP pulses, relevant empirical data can be collected and used to create models during initial training phases.

Various embodiments of the present invention are directed to an adaptive control method and systems for improving or optimizing controlled EP pulse parameters during EP of cells and tissues using the aforementioned closed-loop EP control systems and devices.

In some embodiments, the control systems may include a measurement device, an initializing module, a signal generator, a controller and a memory module. The control methods described herein are implemented in the control systems.

In one aspect, the measurement device measures tissue/cell conditions such as dielectric and conductive properties of cells and tissues. The measurement device may include one or more different measuring devices to facilitate measuring the tissue/cell conditions. For example, the measuring device may include a voltage sensor/device and/or a current sensor/device. The voltage sensor may be configured to measure voltages across cells or tissues when an excitation signal and/or EP pulses are applied to the cells or tissues. The current sensor measures current across the cells or tissues when an excitation signal and/or EP pulses are applied to the cells or tissues. The results of the measurements (e.g. measured data) may be sent to the controller for further processing.

The initializing module may be configured to initialize EP pulsing parameters for performing EP on the cells and tissues. The EP pulsing parameters may be predetermined EP pulsing parameters empirically established based on previous experiments/clinical trials. Alternatively, the pre-determination of the EP pulsing parameters may be based at least in part on one or more trained models. A signal generator may generate the excitation signal and/or electroporation pulses that are applied to the cells and tissues. The measurement device measures the tissue/cell conditions such as dielectric and conductive properties of cells and tissues in response to the application of the excitation signal and/or electroporation pulses.

As noted, the controller receives the measured data, which corresponds to results of the measurements of the tissue/cell conditions. The controller then processes the measured data to facilitate diagnosis/identification of characteristics of the tissues and cells and/or determine updated control parameters for the system. For example, the hetero- or homogeneity of the tissue can be evaluated. The controller may include (in any combination) a pre-processing module, a feature extraction module, a diagnostic module and a pulse parameter estimation module.

The pre-processing module obtains measured data from the measurement device and pre-processes the measured data to separate desirable data from undesirable data. For example, the undesirable data may include noise, direct current bias. The pre-processing may include scaling the measured data based on standardized values such as standard deviation, performing digital filtering of the measured data and validating the measured data.

The feature extraction module extracts information such as relevant features from the desirable data. The relevant features may be quantitative information. For example, the quantitative information may be extracted using computational routines described herein. The relevant features of the desirable data are sent to the diagnostic module for further processing. For example, the diagnostic module applies at least a portion of the relevant features of the desirable to one or more trained diagnostic models to determine whether the next step is to select next applied EP pulsing parameters or to stop the control process if a diagnostic issue is detected, e.g., electrodes not placed in tissue. The pulse parameter estimation module is configured to select or generate the next applied EP pulsing parameters based on an outcome of the diagnostic module and the feature extraction module.

In some embodiments, the present invention is directed to a "one-step ahead feedforward control". By "one step ahead feedforward control" it is meant that before a first EP pulse is applied, the parameter estimation routine initializes the initial control parameters for the first pulse based on the model trained in the initial training phase using the empirical data from the previously conducted experiments. These previously conducted experiments may be based for example on tissue samples with tumors having similar characteristics to those of the current tissue to be subjected to the control method of the present invention. For example, types, sizes or locations of melanoma tumors can be used to build a dataset to serve as the basis for the initial model. Initial excitation signals including voltage and current signals are applied through a signal generator (e.g. the proprietary signal generator described herein). The measurement device measures the response of the tissue to the excitation signals. The controller derives "features" based on the measurements and uses the trained model to compare the extracted features to old features derived from the empirical data obtained in the previously conducted experiments. The old and derived "features" are obtained from tissue sensing measurements, e.g. EIS. The models may be trained based on a tissue or tumor type identified by the diagnostic module in a diagnostic phase, and then used to select optimal parameters/conditions for the first EP pulse. These first pulse parameters are thus "fed forward" to be applied as the first pulse for the control routine as opposed to the conventional EP systems and methods in which parameters/conditions of the first pulse are based on fixed or static conditions. In this sense, the methods of the present invention utilize feedforward control to provide optimal EP parameters based on a sensed tissue type, in conjunction with feedback control to sense cell conditions, e.g., degree of permeabilization and adjust the pulse parameters accordingly.

Variations in tumor characteristics, e.g., tumor location, size, and degree of vascularization, fibrosis, and necrosis which normally affect treatment outcome result in poor predictability of effective EP conditions for gene delivery and, consequently, variable therapeutic outcomes. Conventional EP systems apply an open-loop control system using static parameters that rely on a priori knowledge determined by preclinical studies in homogeneous syngeneic tumor models. However, preliminary data has shown that even in homogeneous tumors, the time required to apply an electrostatic field across a cell membrane follows a log-normal distribution. Applying static parameters to different tumors, even in a homogenous model, results in a wide range of applied electrostatic fields across cell membranes and leads to treatment variability. The present invention overcomes the aforementioned deficiencies of the prior art by implementing control methods employing closed-loop control systems using tissue-sensing based feedback to optimize the EP process with tumor-specific measurements acquired before and between each EP pulse. Thus, by using EIS feedback control combined with the "one-step ahead feedforward control," the present invention is able to more effectively predict effective parameters for EP taking into account the variations in tumor characteristics that normally affect the treatments.

II. Electrochemical Impedance Spectroscopy (EIS)

The systems and methods of the invention may include Electrochemical Impedance Spectroscopy EIS (or tissue sensing) measurements which may be conducted using an EP device. In some embodiments, the EP device may include electroporation electrodes (EPEs) for applying EP pulses and electrical measurement electrodes (EMEs) for applying low voltage interrogation signals to the cells. In some embodiments, the electrodes of the EP device function as both EMEs and EPEs and solid state relays may be used to switch between high voltage EP pulse circuitry and low voltage EIS interrogation circuitry, as illustrated in FIG. 1. FIG. 1 is simple schematic depicting some of the components of an EP device used to apply electric pulses for EIS according to the present invention. Although an electrode array of 4 electrodes is shown, this is not limiting, with arrays of pairs of electrodes including 2, 4, 6, 8, 10 and 12 or more electrodes all finding use in the invention. Furthermore, although the electrodes are shown as having a straight shape, this is not limiting as the electrodes may have curved or spiral shapes, as shall be described below with respect to various EP devices that may be used in the systems and methods of the present invention. FIG. 1 depicts the situation where the electrodes of the array function either as EP electrodes when connected to the EP circuitry or serve as electrical measurement (EM) electrodes when connected to the tissue sensing/EIS circuitry. As discussed herein, when the electrodes of the EP device function as both EMEs and EPEs, the electrodes switch between EPE and EME modes through relay switch. That is, solid state relays are used to switch between the high voltage EP pulse circuitry and the low voltage EIS interrogation circuitry, as illustrated in FIG. 1. That is, the proprietary generator of the present invention is capable of supplying both high voltage pulses and low voltage interrogation signals to the EP device as necessary. In other embodiments where the EP device is provided with separate EPEs and EMEs, the EP device may be connected to two power sources via a switching mechanism that switches on and off when a small excitation voltage is applied across its control terminals. These switches use coupling mechanisms which include electromagnetic, electromechanical, piezoelectric and photoelectric mechanisms.

Due to general knowledge about electroporation conditions, capacitance and resistance measurements acquired prior to applying EP pulses enables a priori knowledge of the conditions that will cause destabilization of capacitive elements such as cell membranes. Measuring capacitance between pulses allows the electrical conditions, including pulse width (which can be calculated from associated time constants) to be adjusted based on the time constants associated with membrane capacitance and resistance. In addition, this information allows the process to be stopped when an ideal drop in time constant is reached, e.g. when membrane integrity has been compromised, thus allowing the introduction of therapeutic moieties.

In some embodiments, the EP device uses different sets of EPEs and EMEs, as is generally depicted in FIG. 3. In some cases, as is more fully outlined below, when different sets of sets of EPEs and EMEs are used, the EMEs and the EPEs can be offset, allowing for impedance measurements in different areas of the electric field zone, as generally discussed below and in the legend for FIG. 3. In these embodiments, an additional low voltage EME power supply is used, in addition to the higher voltage EPE power supply, along with the appropriate circuitry and connectors.

Figure 48:
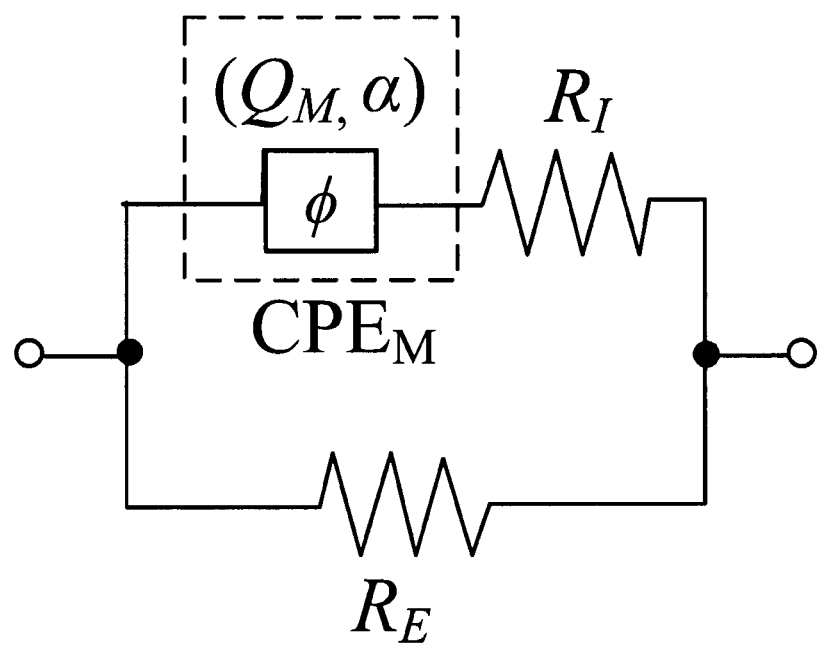
FIG. 48 illustrates an equivalent circuit model of the tissue.

In other preferred embodiments, as described above, and as shall be used to illustrate the systems and method of the present invention, the EP device uses a single set of electrodes for both EP and EIS measurements. EIS measurements can be performed using EPEs without negatively impacting tissue characteristics. Using the same electrodes to perform low power EIS measurements and high power EP pulses is ideal, as this reduces the number of required electrodes and directly measures tissue responses. EIS is a low power technique capable of real-time monitoring of tissues. This technique is performed by applying a series of low voltage excitation signals across a pair of electrodes and measuring a response current over a range of frequencies. The magnitude and phase of each applied excitation is then computed and fit to an equivalent circuit model of the tissue as illustrated in FIG. 48, hereinafter termed "CPE-based Tissue Model."

Impedance measurements may be obtained using the equation below:

$$Z(f) = \frac{1}{Q_0(2\pi f)^a} e^{-j\pi a/2} + R_s$$

In the above equation, Z(f) is Z(f) is tissue impedance in Ohms; f is frequency in Hertz; j is a constant representing $\sqrt{-1}$; $Q_0$ is admittance (at f=1 Hz) in Siemens; $R_s$ is resistance in Ohms; and a is the constant phase element (CPE) in no units.

As illustrated in the model, resistive elements ($R_I$ and $R_E$) are due to the intracellular and extracellular matrix, respectively, and lipid structures are represented by the constant phase element ($CPE_M$) of the tissues and cells. $CPE_M$ is a function that represents the charge or capacitance of the lipid bilayers (denoted by $Q_M$) and a scalar ranging from 0 to 1 representing the non-ideal nature of the capacitor (denoted by α). As shall be discussed further below, the time-constant for charging the lipid bilayer, may then be computed as $\tau=(R_I Q_m)^{1/\alpha}$. Computing of the time constant in this manner is integral to the methods of the present invention, as the time constant is then used to identify the optimal EP pulse durations before, during and/or after each treatment.

By using the array of EPEs and/or additional electrical measurement electrodes, EMEs, the tissue in the zone surrounded by the electrode arrays can be interrogated. This information can be used to direct EP conditions, for example. That is, using different EIS interrogation input signals, such as chirp pulses (or many others as outlined below), the output signals allow the device to fit to the tissue models to determine the properties of the tissue and the EP signals to use. For example, with reference to FIG. 3, after insertion of the electrodes, different interrogations can be run. For example, comparing impedance between electrodes 1 and 2 to impedance between 1 and 8 can help determine that the tissue between electrodes 1 and 8 is "normal" tissue, as compared to "abnormal" or "diseased" tissue between 1 and 2. Similarly, interrogation between electrodes 7 and 8 or 6 and 7 can help determine that electrode 7 is near or in a blood vessel, and thus should not be used for electroporation. Thus, for example, these measurements can be used to address the four following questions, and any other relevant inquiries depending on data necessary based on the scope of experimentation.

1) Is each electrode making good contact with the tissue? As will be appreciated by those in the art, using electrodes in difficult to access areas or on particularly compliant skin can result in uncertainty if both electrodes adequately inserted into the tissue to be treated. This results in nonhomogeneous electric fields and poor delivery. 2) Are electrodes inserted into viable tissue? Inserting electrodes into abnormal tissue, particular tumor tissue, can be heterogeneous in texture and/or cell integrity, etc., with many tumors having necrotic and/or apoptotic cellular areas. Thus an electrode can be inserted into a location that might not result in good and/or even electric fields, and thus that electrode might not be used in the procedures of the present invention. 3) Is the therapeutic moiety (TM) or drug in the right location? In this embodiment, this measurement can be made pre- and post-injection of the TM solution, and the differences can inform whether more TM solution should be injected. 4) Are there electrodes that should not be used due to their location and/or contact? Again, making reference to FIG. 3, these EIS measurements can allow the determination that electrode 7 is placed irregularly (e.g. in or close to a blood vessel, etc.), or that the location into which the electrode is inserted results in poor electrical contact due to tissue heterogeneity and/or integrity. 5) Is the tissue (e.g. tumor) getting electroporated sufficiently? This is the same as tissue sensing, as this measures the integrity of the cell membrane. Thus, these measurements can be made before EP (to establish a baseline), during EP and after EP, to insure that EP did occur.

In addition, these EIS measurements can be used to determine ideal EP conditions as will be described below in relation to the adaptive control methods of the present invention for providing improved or optimized EP pulsing parameters. In some embodiments, the method of the present invention may include contacting the tissue in the electric field zone 100 or in the electroporation location 110 (shown in FIG. 10) with a pair of EPEs/EMEs 120. A low voltage power supply electrically connected to the EPEs/EMEs is used to apply a low voltage interrogation signal to the EPEs/EMEs. Methods for sensing the impedance and/or capacitance may include but are not limited to waveforms such as phase locked loops, square wave pulses, high frequency pulses, and chirp pulses. A voltage sensor and a current sensor are used to sense a voltage drop and current flowing through the circuit, and these parameters may then be processed by a controller, as illustrated in FIG. 1, to determine an average impedance for all cells in the measured area.

As described above, capacitance and resistance measurements are an indicator of how healthy the cells are, and may be used to determine how long an electric pulse to apply in order to disrupt the cell membrane and provide conditions sufficient for electroporation. Once the average impedance of the cells has been determined, it is possible to determine several characteristics of the measured cells including, but not limited to Initial condition of cells or tissue—for example, whether the cells are diseased (demonstrated by lower than average capacitance), whether the cells are healthy, positioning of electrodes—whether the electrodes are properly positioned surrounding area around tissue/cells of interest/and whether they are in right location for effective electroporation, and the time constant, as briefly discussed above (to be described further below) for the cells.

In some embodiments, impedance measurements may be made across several EI sensing electrode pairs to determine whether the average across all cells in the electric field zone 100 is consistent and for more accurate reading in a specific location. If EI measurements across are not consistent across several electrode pairs, this may indicate inconsistency in homogeneity of cells, thus requiring different time constants to be applied to different sets of electrodes. The time constant gives an indication of pulse width to be applied to the cells for electroporation to occur. Charging a capacitor to its maximum (i.e., where the capacitor/cell cannot store energy due to electroporation, where good transfection occurs) takes about 5 time constants. As a result pulse width for charging a capacitor to a point just before electroporation occurs can be determined therefore pulse width necessary to charge capacitor to at least 5 time constants ($\tau_C$). After the time constant is determined, the pulse width is set accordingly for each set of EPEs based on the time constant determined for the cells in the area which the EPEs are surrounding.

The time constant may be based on the circuit model illustrated and described above and derived from the series of equations below. The time constant for the purposes of the present invention is described as the amount of time ($\tau$) required for the potential applied across the terminal ($V_a$) to drive the CPE to one-half of the applied potential ($V_{CPE}=V_a/2$).

$$|V_{CPE}| = |V_a| \left( \frac{Q_0^{-1}(2\pi f)^{-\alpha}}{Q_0^{-1}(2\pi f)^{-\alpha} + R_s} \right) \quad (1)$$

$$|V_{CPE}| = |V_a| \left( \frac{1}{1 + R_s Q_0 (2\pi f)^{\alpha}} \right) \quad (2)$$

$$f = \frac{1}{2\pi}(R_s Q_0)^{-1/\alpha} \quad (3)$$

$$\tau = (R_s Q_0)^{1/\alpha} \quad (4)$$

Here, $|V_{CPE}|$ is the voltage across the CPE, and $|V_a|$ is the voltage applied across the terminal or membrane. At (2) $|V_{CPE}|$ is substituted with $|V_a|/2$, thus leading to step (3) where f is computed, and f is substituted with $$f = \frac{1}{2\pi\tau}$$

to derive the final time constant equation which is used in computations of ideal pulse width for EP pulses.

Thus, the methods and systems of the present invention utilize electrical-based measurements and feedback to drastically improve EP process, as shall be described further below. Since the EPEs are used as both EPEs and EMEs, feedback is provided by the EPEs, thus no extra hardware needed. Fitting electrical data to the modified Randles model circuit allows parameter monitoring for conditions of membranes. Tumor tissue can thus be fit in real time to a modified Randles equation. Modification involves substituting capacitive/resistive element for constant phase element (CPE). CPE provides a realistic representation of membranes where Q=admittance; and $0 \leq \alpha \leq 1$.

Figure 10:
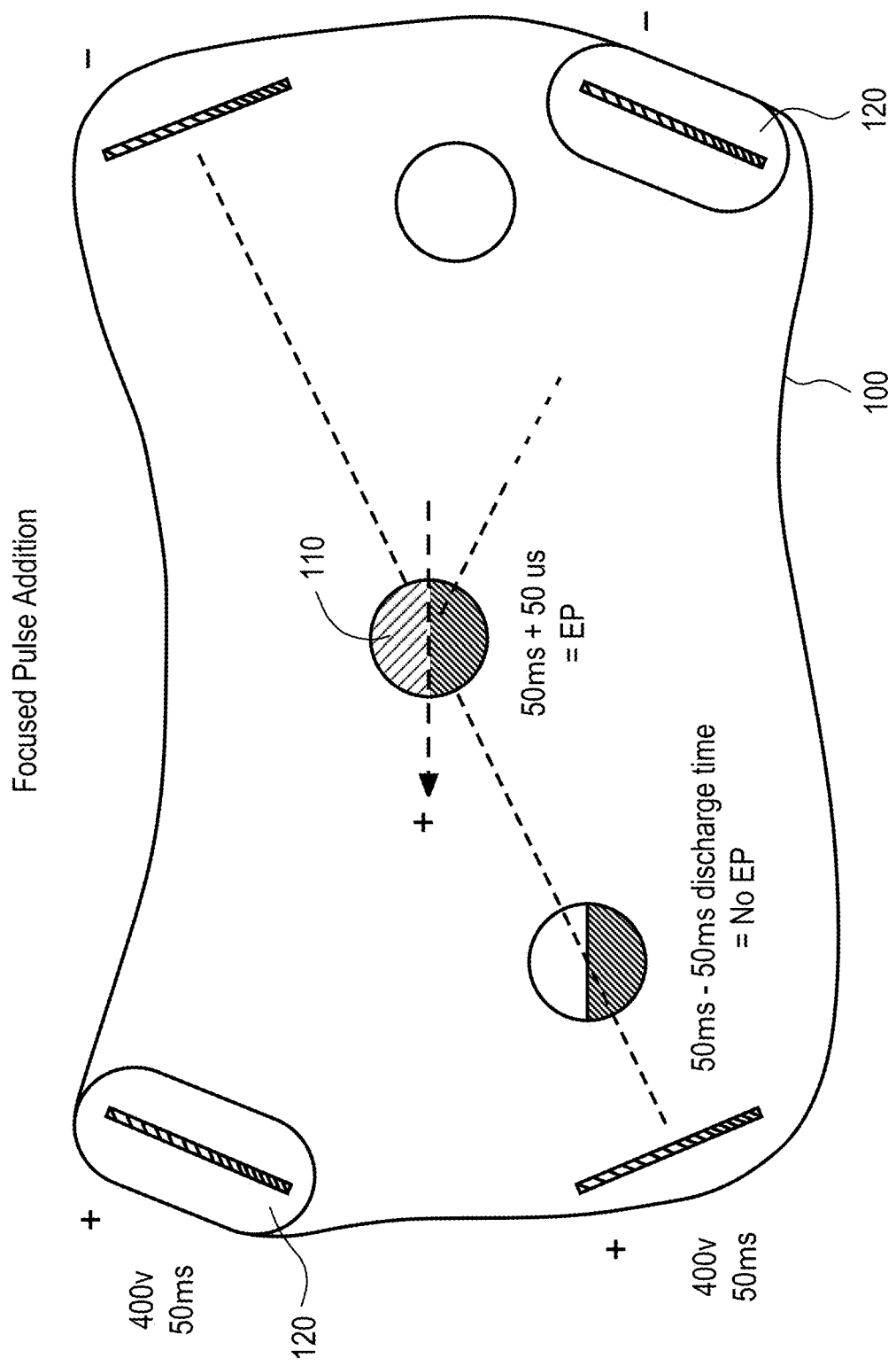
FIG. 10 is a schematic illustration of a first pair and a second pair of EPEs defining an electric field zone and an electroporation location according to the present invention.
Figure 14A:
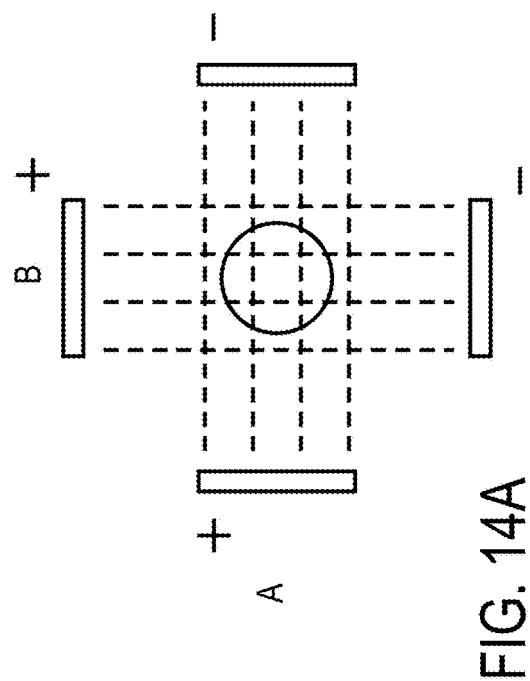
FIG. 14A and FIG. 14B are illustrations of a continuous pulsed electric field in the electroporation location and an alternating on and off pulsed electric field in the electric field zone but outside the electroporation location, according to the present invention.
Figure 14B:
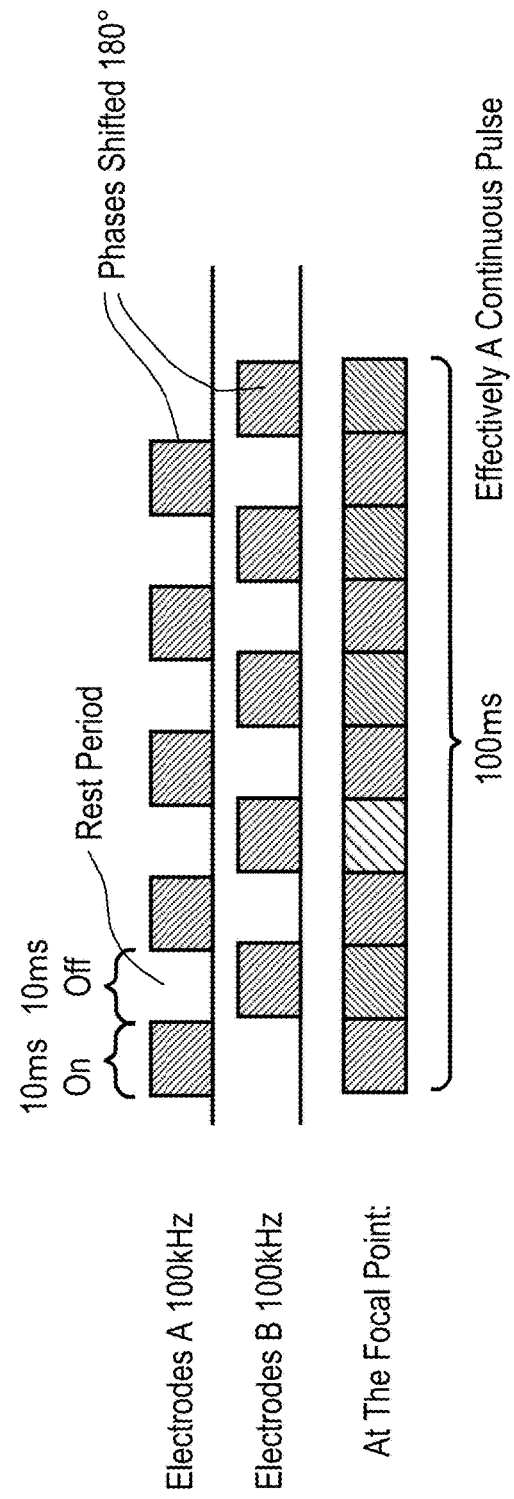
Figure 15:
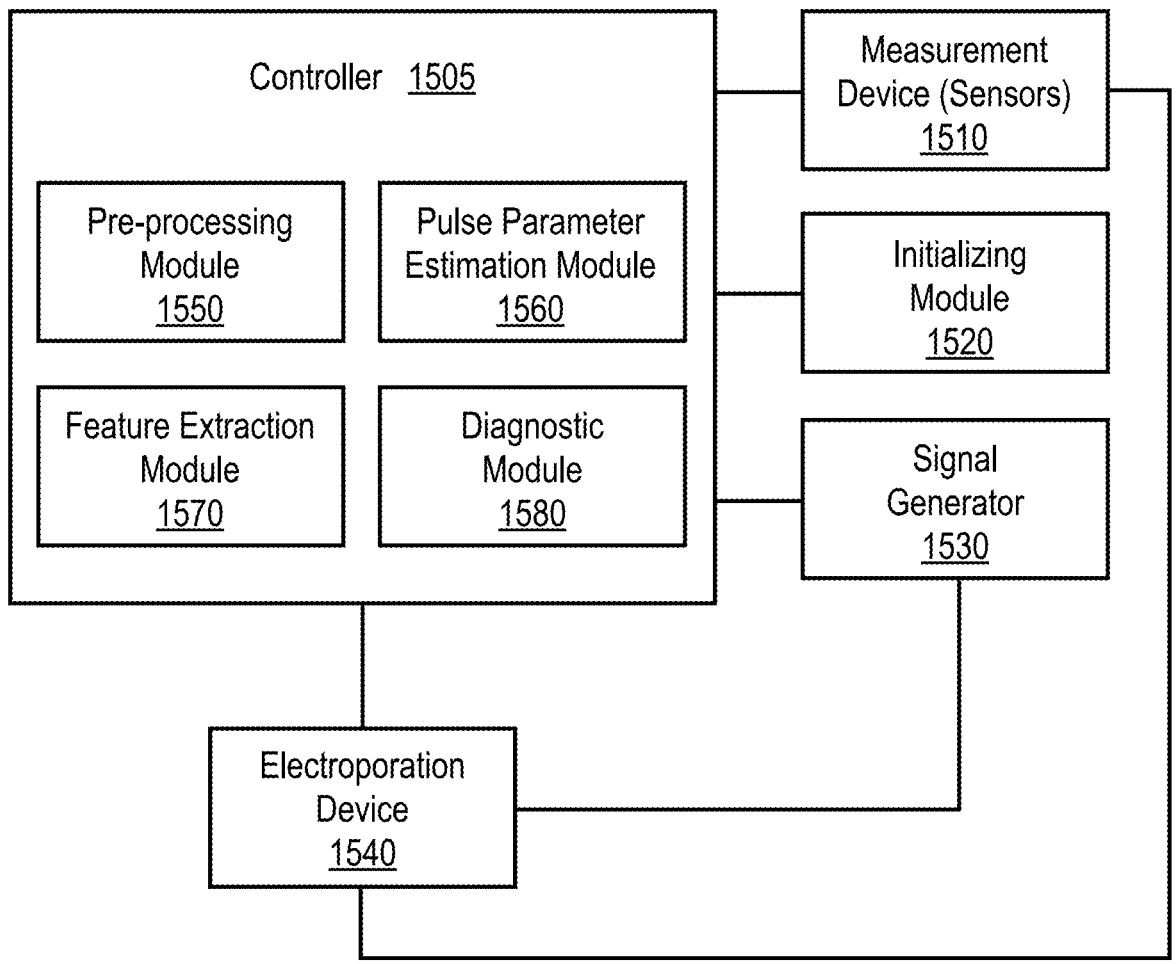
FIG. 15 is a simple schematic illustrating an adaptive control system for optimizing electroporation (EP) pulse parameters during electroporation (EP) of cells in a tissue of a subject according to the present invention.

FIG. 10 is a schematic illustration of a first pair and a second pair of EPEs defining an electric field zone and an electroporation location according to the present invention. FIG. 14A and FIG. 14B are illustrations of a continuous pulsed electric field in the electroporation location and an alternating on and off pulsed electric field in the electric field zone but outside the electroporation location, according to the present invention. As will be appreciated by those in the art, successful electroporation occurs when the cellular membrane is disrupted, resulting in a change of capacitance and resistance. When subjected to an electric field, cells generally act as capacitors. When the electric field is applied for a long enough period (depending on the cell properties, health, size, etc. . . . ) charge accumulates at the cell membrane until it reaches a certain threshold and causes a breakdown of membrane integrity. In the embodiments where the EPEs and EMEs are different electrodes, the EMEs may be powered by a low voltage interrogation circuit. The present invention also includes a voltage sensor, and a current sensor, as illustrated in FIG. 15 to measure current and voltage across cell membranes and tissue and the controller to process the voltage and current to determine an average capacitance for cells in the electric field zone 100.

Impedance may be measured based on charge redistribution in the cells in response to low frequency electric field excitations of the low voltage interrogation circuit. Impedance may be measured before, between and after electroporation electric fields are applied to determine cell conditions, including, but not limited to cell health, placement of electrodes relative to cells for optimum electroporation, and most importantly a time constant which can be used to determine pulse width of electric fields to be applied to the cells in the electric field zone. As described before, in general, charging a capacitor to its maximum, i.e. right before electroporation occurs, takes a period of five time constants, therefore the pulse width of the initial electroporation electric field pulse may be set to 5 times the time constant. This pulse width is insufficient to cause electroporation in the cells which are outside of the electroporation location 110, as described above, but sufficient to cause electroporation in the cells of the tissue in the electroporation location 110 which is subjected to the additive effects of the electric fields from all sets of EPEs being applied as one continuous electric field. Impedance measurements may be applied again after the first EP electric fields have been applied, and a percentage drop in impedance or time constant may be calculated and compared to a predetermined value to determine whether cells in the electroporation location have been electroporated sufficiently. If not, the systems and methods of the present invention adjust the pulse width—based on the calculated percentage drop in capacitance—for the next set of electroporation pulsed electric fields until it is determined sufficient EP has occurred in the EP location. Therefore, impedance measurements between pulses allows for electrical conditions, namely pulse width to be adjusted based on time constants associated with cell membrane capacitance and resistance, and the electroporation process can be stopped when an ideal prop in capacitance, time constant, or membrane integrity is reached.

Various embodiments of the present invention are directed to control systems and methods for electroporating cells in an EP location of a tissue using the various electroporation devices of the present invention, described herein.

III. Adaptive Control Systems of the Invention

Figure 16:
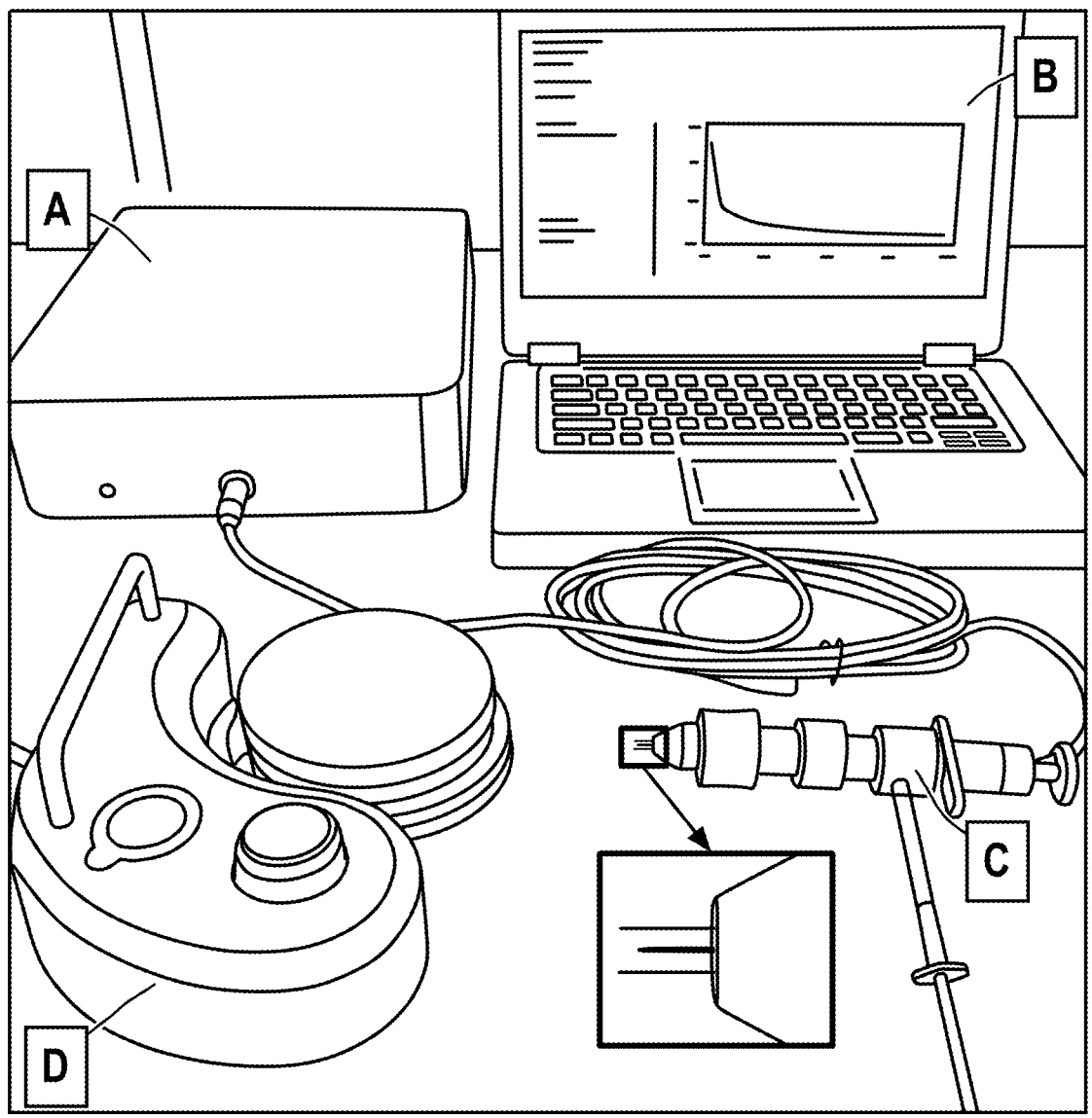
FIG. 16 illustrates an EP system for use in the adaptive control system during electroporation (EIS) of cells in a tissue of a subject according to the present invention.

Various embodiments of the present invention are directed to systems for providing adaptive control, implemented in an electroporation (EP) device, to optimize controlled parameters during EP of cells and tissues. In some embodiments, as illustrated in FIG. 15 and FIG. 16, the adaptive control system includes a measurement device configured to measure dielectric and conductive properties of cells and tissues.

Examples of dielectric and conductive properties may include capacitance, resistance and impedance. In some embodiments, the measurement device includes a voltage sensor configured to measure voltages across cells or tissues resulting from each of an excitation signal and each EP pulse applied to the cells or tissue, and a current sensor configured to measure current of the cells or tissues resulting from each of the excitation signal and the at least one applied EP pulse. The voltage and current measurements are indicative of and are used to calculate various dielectric and conductive properties of the cells and tissues FIG. 15 is a simple schematic illustrating an adaptive control system for optimizing electroporation (EP) pulse parameters during electroporation (EP) of cells in a tissue of a subject according to the present invention and FIG. 16 illustrates an EP system used in the adaptive control system during electroporation (EIS) of cells in a tissue of a subject according to the present invention. In some embodiments, as illustrated in FIG. 16, the EP system of the present invention includes (A) an EIS equipped EP generator (e.g., generator 1530 of FIG. 15) with data logging, (B) a graphical user interface for programming pulse conditions, setting feedback criteria, and downloading EIS and pulse performance characteristics, (C) a proprietary applicator (EP device) consisting of dual electrodes surrounding a central injection lumen, and (D) a foot pedal switch to remotely activate the EP process. Although the EP system of FIG. 16 illustrates one type of EP device, it should be understood that the control system of the present invention may incorporate any of the EP devices described herein to perform the adaptive control methods described herein.

In some embodiments, the adaptive control system includes an initializing module 1520 configured to initialize EP pulsing parameters for performing electroporation in the cells or tissue. The EP pulsing parameters may include but are not limited to voltage magnitude, repetition rate, and pulse width. The initialized EP pulsing parameters are based at least in part on at least one trained model. The trained model may be, but is not limited to a physics-based model, an empirical model, or a data-driven model. EP pulsing parameters may include but are not limited to pulse width, number of pulses, amplitude/field strength, and frequency.

In some embodiments, the adaptive control system further includes a signal generator 1530 configured to generate the excitation signals and deliver EP pulses through the (EPEs/EMEs) to the cells and tissue. The signal generator 1530 may be an EIS equipped pulse generator which provides the initial excitation signal at a predetermined pulse width based on experimental data observed offline, i.e. in previous electroporation experiments conducted with tissues/cells having similar properties as those to be subjected to the control methods of the present invention. In some embodiments, the signal generator 1530 is capable of supplying both a low voltage excitation (interrogatory) signal, as well as a high voltage signal for an EP pulse. An example of such a generator is the proprietary generator (A) illustrated in FIG. 16. The generator is capable of performing real-time feedback control based on EIS data before and between each EP pulse. The generator can output a minimum of 10 V and maximum of 300 V with pulse durations ranging from 100 s to 10 ms. EIS data captured before and between pulses is obtained by the generator over a range of 100 Hz to 10 kHz with 10 data points acquired per decade. Acquisition of EIS data over this spectra is accomplished in 250 ms, which is rapid enough to: (1) execute routines to determine a time constant for the next pulse; (2) store EIS data for post analysis; and (3) not interrupt clinically used EP conditions. The generator may be capable of a minimum output load impedance of 20 ohms and a maximum load impedance of an open circuit. The custom generator interfaces with a variety of standard EP device applicators, and is capable of supporting up to 6 electrodes. Solid state relays may be used to switch between high voltage EP pulse circuitry and low voltage EIS interrogation circuitry. To allow hands-free operation of the generator a foot pedal may be added to trigger, pause, or abort the EP process.

The measurement device 1510, including the voltage sensor and current sensor, measures voltage and current across the cells and tissues in response to application of the excitation signals and/or EP pulses. In some embodiments, the measurement device is incorporated into the electrodes of the EP devices 1540 of the present invention, but is not limited thereto. In other embodiments, the measurement device may be separate from the electrodes and implemented elsewhere in the control system.

In some embodiments, the control system of the present invention includes a controller 1505 configured to receive sensor data from the measurement device corresponding to results of the measured cells or tissue properties (i.e. dielectric and conductive, e.g. capacitance, resistance and impedance) and to process the data into diagnostics and updated control parameters. In some embodiments, the controller consists of four modules, including a pre-processing module 1550, a feature extraction module 1570, a diagnostic module 1580, and a pulse parameter estimation module 1560. The preprocessing module obtains data from the current and voltage measurements, and pre-processes the data to separate desirable data from undesirable data. Undesirable data may include but is not limited to outliers, out of range values, and missing values. Data gathered from the EIS measurements is fit to the tissue impedance model, i.e., the CPE-based Tissue Model described above, in real-time using the controller, e.g. a microprocessor with a reduced instruction set computing architecture.

In some embodiments, the feature extraction module extracts quantitative information from the desirable data using computational routines. The computational routines may include but are not limited to linear curve fitting parameters, non-linear curve fitting parameters, cross correlation, curvature, mean, averages, medians, range, standard deviation, variance, and kurtosis. When operating in feedback mode, features of the measured EIS data can be used to control parameters associated with the EP process.

In some embodiments, the diagnostic module applies at least a portion of the relevant features of the desirable data to at least one trained diagnostic model. The diagnostic model along with the relevant features is used to make decisions for the applied pulse. The diagnostic module may combine several features to identify whether there is correct needle placement of the EP device, whether the drug or gene is located between EPE pairs, whether the EP pulse was effectively applied for transfection, and whether another pulse can be applied to the same electrode pair.

In some embodiments, the pulse parameter estimation module is used to generate the next applied EP pulsing parameter based on the outcome of the diagnostic module and feature extraction module. In some embodiments, the control system of the present invention further includes a memory module to store the processed device/sensor data and said trained models for feature extraction by said controller.

IV. Electroporation Devices and Methods

A. EP Electrode Configurations

The EP devices of the present invention find use in two main therapeutic areas: delivery of therapeutic moieties and tissue electroporation/ablation. In general, and for many of the embodiments outlined herein, the patient is suffering from a disease such as cancer that is localized in particular tissues that will benefit from the intracellular delivery of therapeutic moieties (TMs). Alternatively, in some embodiments, it is desirable to kill small loci of cells within a tissue (sometimes referred to in the context of electroporation as "irreversible electroporation" or "electroporation ablation"). As is known in the art, one advantage of irreversible electroporation is that it results in apoptosis rather than necrosis as for other common ablation techniques. While most of the discussion herein is related to the former, the FPA systems and methods in the absence of TM delivery are contemplated throughout.

The EP devices and methods of the invention are used to electroporate cells in a tissue of a patient or subject as well as deliver TM to the electroporation location for treatment thereof. In general, the EP devices of the invention are used to treat diseased or abnormal tissue, such as cancerous tissues. The term "cancer" includes a myriad of diseases generally characterized by inappropriate cellular proliferation, abnormal or excessive cellular proliferation. Examples of cancer include but are not limited to, breast cancer, colon cancer, prostate cancer, pancreatic cancer, skin cancers (including melanoma, basal cell carcinoma and squamous cell carcinoma), lung cancer, ovarian cancer, kidney cancer, brain cancer, or sarcomas. Accordingly, cancerous tissues including skin tissue, connective tissues, adipose tissues, etc. can be treated using the systems of the invention. Such cancers may be caused by chromosomal abnormalities, degenerative growth and developmental disorders, mitogenic agents, ultraviolet radiation (UV), viral infections, inappropriate tissue expression of a gene, alterations in expression of a gene, or carcinogenic agents. The term "treatment" includes, but is not limited to, inhibition or reduction of proliferation of cancer cells, destruction of cancer cells, prevention of proliferation of cancer cells or prevention of initiation of malignant cells or arrest or reversal of the progression of transformed premalignant cells to malignant disease or amelioration of the disease. The term "subject" or "patient" refers to any animal, preferably a mammal such as a human. Veterinary uses are also intended to be encompassed by this invention.

The systems and methods of the invention find use in the electroporation of cells in a tissue. By the terms "electroporation", "electro-permeabilization," or "electro-kinetic enhancement" ("EP") as used interchangeably herein refer to the use of a transmembrane electric field pulse to induce microscopic pathways (pores) in a bio-membrane; their presence allows therapeutic moieties (including but not limited to biomolecules such as plasmids, oligonucleotides, siRNA, drugs, ions, and water) to pass from one side of the cellular membrane to the other. Through the application of the electric field over a period of time, the cell membrane accumulates charge and creates a trans-membrane voltage, according to the formula $Vm=1.5 \times Radius \times E_{ext}$, with Radius being the radius of the cell, and $E_{ext}$ being the external electric field of the cell. In general, the cell membrane breaks down (e.g. forms pores) at roughly one volt, although the size and shape of the cells, in addition to their placement in the electric field, can make a difference. For example, long muscle cells have a higher capacitance across the cell width than along their length. Similarly, larger cells are generally electroporated at lower voltages. As discussed herein, the use of either the EM or capacitance sensing techniques of the invention can help optimize the EP pulses and duration by determining the bulk properties of cells in the electric field.

"Electroporated cells" include those that have transitory pores open in the cellular membrane, which close as the charge on the cell membrane dissipates ("open pore cells"), and those that have undergone electroporation such that the cells now contain the exogeneously added therapeutic moieties and have closed pores (e.g. are intact again).

Figure 9:
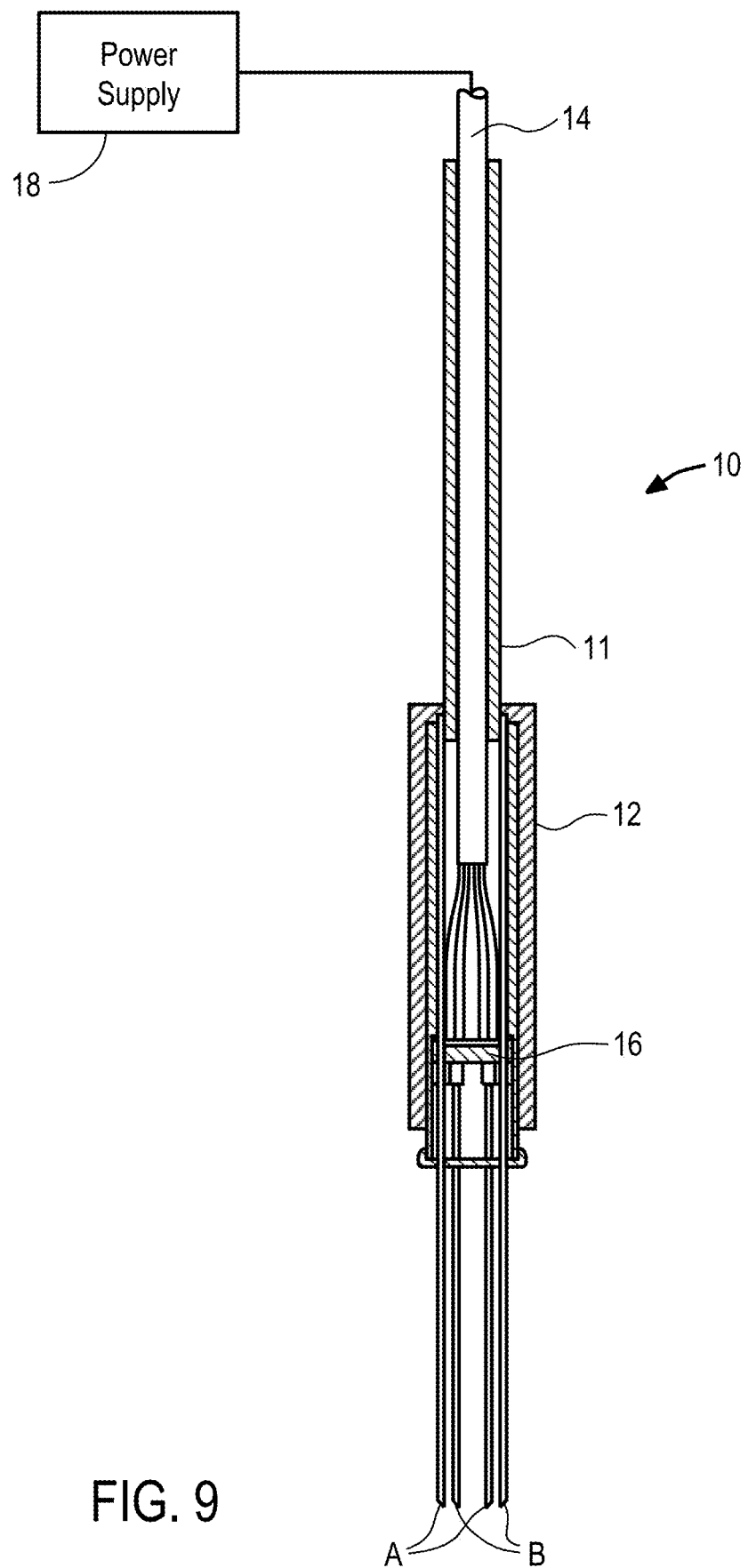
FIG. 9 is a schematic of an EP device including a wand housing with a first pair and a second pair of electrodes according to the present invention.

Referring to FIG. 9, an electroporation device according to various embodiments of the present invention is illustrated and designated generally by the numeral 10. The electroporation device 10 may generally include an electroporation wand housing 12 which is optionally in the form of a cylindrical tube (although other geometries can be used), a first pair of electroporation electrodes A and at least a second pair of electroporation electrodes B housed in the wand housing. The wand housing can optionally include other components, including the systems for TM delivery, the switching circuitry, etc.

In some embodiments, the wand housing is formed for ease of physician use, for example having molded handle parts or grips, optional lighting elements at the distal end, cameras for observing and documenting treatment sites, biopsy forceps, tissue scissors, ligation devices, suturing systems, etc.

By "pair of electroporation electrodes" "EPE" herein is meant a pair consisting of two electrodes, which, when connected to a power supply are configured to be oppositely charged. The first and second pairs of electroporation electrodes may be stationary or retractable within the electroporation wand housing 12. The electroporation wand housing 12 may further include a circuit board 16 having a plurality of sliding through-sockets through which the electroporation electrodes A and B are slidably retractable and extendable. The electrode pairs A and B are mounted in the electroporation housing 12 which is slidably engaged with an indicator or gage 11. As the electroporation wand housing 12 is moved along the gage 11, it alternately extends and retracts the electrode pairs A and B. The device indicator or gage 11 may provide an indication of the length of extension of the electrode pairs A and B. The electroporation device may further include an electrical connector 14 to electrically connect each of the first A and second B electrode pairs to a power supply 18, e.g. a pulse generator. The electrical connector includes four or more conducting wires (depending on the number of electroporation electrodes for transmitting electrical signals from the power supply to the each of the electroporation electrodes. These signals may include needle voltage setpoint, pulse width, pulse shape, the number of pulses, and switching sequence. As described above, and as will be appreciated by those in the art and more fully described below, the EPEs may also serve as EMEs, in which case the generator may be capable of supplying both high voltage EP pulses and low voltage EIS interrogation signals, or a second low voltage power supply is used with appropriate switching mechanisms to allow the delivery of higher voltage EP signals and then lower voltage EIS signals.

Figure 11:
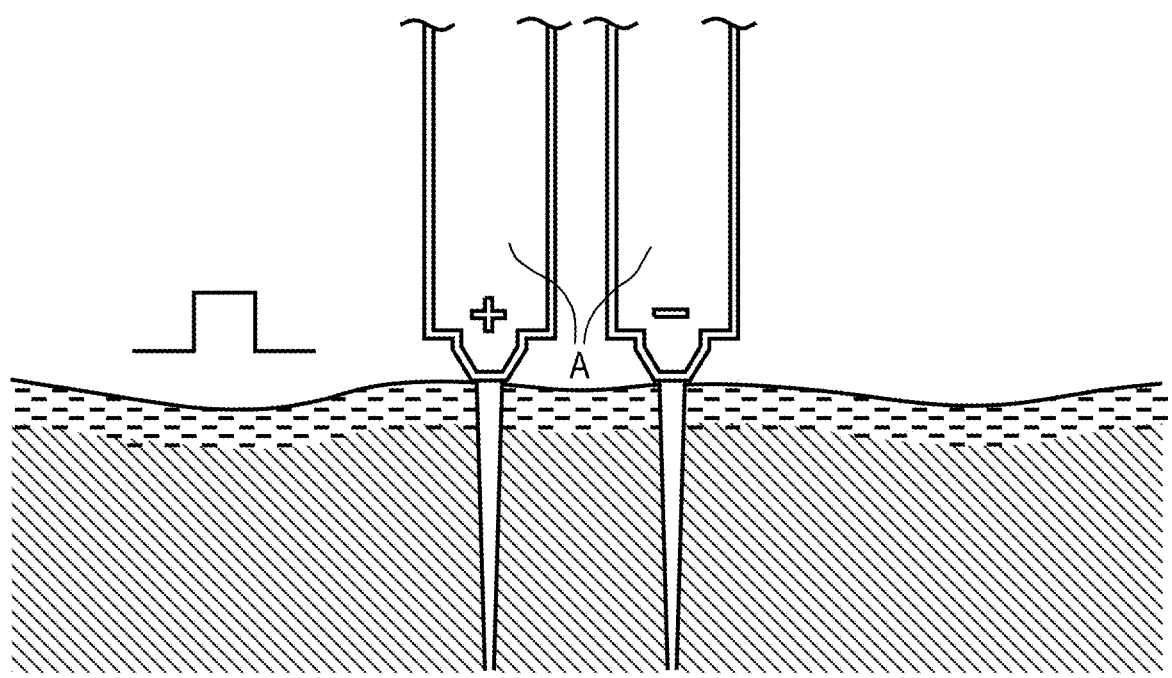
FIG. 11 is an illustration of a pair of non-penetrating EPEs according to the present invention.

In some embodiments of the present invention, one or more of the EPEs may be non-penetrating electrodes which may have an open distal end for administering therapeutic moieties to the tissue, as illustrated in FIG. 7A and FIG. 11. The non-penetrating electrodes could be any suitable shape conductor such as a button or plate to contact the surface tissue. The injectors may be disposed in spaced relation to one another and in close contact with a surface region of the tissue of the subject. The portion of the non-penetrating electrodes in contact with the tissue surface is electrically conductive and electrically connected to a power supply e.g., power supply 18 through an electrical connector, e.g., electrical connector 14, such that EP is accomplished by delivering an electrical current through the region of tissue by completing the circuit between the electrically conducting distal ends of the non-penetrating EPEs.

The EPEs may be formed of material which is conductive, although optional insulative coatings may be used as discussed herein. The EPEs may be made of any conductive material able to pass the large instantaneous current densities associated with high-voltage pulses applied, including, but not limited to certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include AgCl, cobalt-chromium, titanium, stainless steel, platinum, gold, or metal of high electrical conductivity which is plated in gold or platinum.

In some embodiments, for example when non-penetrating electrode pairs are used, distal ends of the electrodes are exposed for generation of the electric fields, but proximal ends thereof may be coated with a non-conductive substance so as to limit application of the electric field to only the distal ends of the electrodes adjacent to the tissue.

In some embodiments, EP electrodes configured for insertion can similarly be coated with insulative material such that electric fields are generated using the distal end of the electrodes and not along the length of the electrodes, for example to allow EP "deeper" in the tissue but not at "shallow" regions.

In some embodiments, the insertion EP electrodes can have areas of alternating insulative material and bare electrodes, as generally depicted in FIGS. 4A and 4B. In this embodiment, the electrodes can be coated in the same pattern, resulting in more uniform electric fields, or different patterns, resulting in asymmetrical electric fields. Similarly, for all the electrode configurations herein, the electrodes can have the same lengths or different lengths.

The pulsed electric fields generated by such partially insulated electroporation electrodes are primarily concentrated in regions between and near exposed tip portions at the distal ends of the electrodes during a treatment, and are small in regions between and near the insulated portions. A partially insulated needle array can be used to confine the electroporation in a targeted area with a tumor and significantly shield the skin and tissues beyond the target area from the electroporation process. This provides protection to the healthy skin and tissues, which may be at risk due to undesired or even adverse effects caused by some therapeutic moieties when injected into healthy surface tissue above the target area.

FIGS. 7A, 7B, 7C and 7D depict different EPE configurations, although only a single pair of electrodes are depicted for simplicity. FIG. 7A depicts one set of non-penetrating solid EPEs, applied topically to the surface of the skin. Additional sets of EPEs are not shown, but are included.

FIG. 7B depicts one set of solid EPEs that are penetrating into the tissue; in this embodiment, the tip of each EPEs is generally pointed to facilitate insertion into the tissue, such as a solid needle tip. In this embodiment, the electric field zone is "deeper" in the tissue, e.g. below the surface. This results in a three dimensional electric field along the length and radial dimensions between the electrodes. In general, these penetrating EPEs can be from about 1 to about 20 mm, depending on the geometry and physiology of the tissue to be treated. It should be noted that this measurement is the depth of insertion and not the total length of the electrodes; in general there will be a portion of the electrode that extends up from the point of contact with the tissue and extends into the wand housing for attachment to the appropriate circuitry, to hold the electrodes in the correct spatial configuration, etc. In FIG. 7C, the penetrating solid EPEs are coated with an insulating (non-conductive) material, such that only a distal portion of the electrode is exposed. In the embodiments of FIGS. 7A, 7B and 7C, the TM delivery system will generally be a needle that is shallowly inserted into the EP location between the EPEs (not shown). In FIG. 7D, the penetrating EPEs are hollow, with a lumen for TM delivery and a pointed, open tip connected to the lumen. On the left hand side, the penetrating electrode has a portion along the axis which is coated with an insulating material. As will be appreciated by those in the art, when capacitance measurements are done, the EPEs can either be additionally used as electrical measurement electrodes (EMEs) or there can be separate set(s) of EMEs, as generally depicted in FIG. 6.

FIGS. 8A, 8B, 8C and 8D depicts components of the EP device of the invention (all of which rely on cylindrical needles, although other geometries can be used as well; also, only a single pair of EP electrodes is depicted). FIGS. 8A and 8B depict one set of EPEs (second set not shown) with a TM delivery (TMD) system. FIG. 8A shows the EPEs and TM delivery system inserted into the tissue, with the TMD hollow need with an open end, a lumen for delivering the TM, and the TM whimsically being delivered. FIG. 8B shows the underside of the device, which may be in the distal end of the wand. Alternatively, as shown in FIG. 8C, the TMD system may comprise a standard syringe, inserted manually by the administering physician during the procedure. In this embodiment, the syringe may have an optional needle stop to physically prevent deeper penetration, at a depth that correlates with the depth of the electric field zone. FIG. 8D depicts a TM delivery needle that has multiple openings to delivery TMs. This may be of use when larger biological molecules such as plasmids and antibodies are delivered, as in general, larger molecules (which are additionally usually charged) diffuse more slowly in tissue than other molecules. Thus having multiple delivery loci within the EP location can serve to have a higher percentage of cells in a zone take up the TMs. FIG. 8D depicts three openings or ports, although any number can be used. In addition, FIG. 8D depicts the openings on one "side" of the needle, but openings can be located on any part of the outer surface of the needle, forming spirals or other shapes.

In some embodiments, the electroporation electrodes are generally of a length so as to fully surround the tissue to be treated. In preferred embodiments, all the sets of electrodes (the "array" of electrodes) are the same length within the array, although in some instances, the use of different lengths of electrodes can result in altered and asymmetrical electric fields.

In many embodiments, the width and cross sectional shaping of the electrodes for insertion are configured to minimize pain. Accordingly, the width of the electrodes may be from 0.05 to 1 to 2 mm, and may depend when the electrodes are also used to deliver TMs. In general, when the electrodes are hollow and used for TM delivery they are generally larger to accommodate the lumen for TM delivery.

In addition, the electrodes and wand housing are preferably made of materials that can be sterilized and configurations that similarly minimize microorganism trapping if the electrode array and wand housing is to be reused. In some embodiments, at least the electrode arrays are disposable, and in some embodiments the entire wand housing is also.

In some embodiments of the present invention, sets of electrode pairs are used. That is, as is depicted in the figures, two sets (two pairs, four electrodes) can be used, e.g. a first and a second pair of electroporation electrodes are utilized. The first and second pairs of electroporation electrodes are offset from each other by a predetermined angle. For a set of two pairs of electrodes, the two electrode pairs are offset from each other by an angle of about 90 degrees as illustrated in FIG. 1, with 90 degrees being preferred in some embodiments. The electrodes may also be positioned a distance of 1-10 mm and define an outer periphery of the electric field zone.

In some embodiments, one or more of the electrodes may be a hollow needle for the introduction of therapeutic moieties as discussed below.

The tissue surrounding the EP electrodes is sometimes referred to as a "burn out zone". By "burn-out" zone is meant the area occupied by the tissue directly adjacent to and/or in contact with each of the individual electrode. It is referred to as the "burn-out" zone because the cells come in direct contact with the electrodes which are heated as a result of the high voltage signal from the power supply, and thus the cells are subject to damage by overheating. However, by using the alternating pulse devices of the present invention, the damage to the cells in the burn out zone can be minimized by reducing the heat and field by 50% (in the case of two sets of electrodes, more if more sets are used). In addition, as the electric field strength is focused/increased at the electrodes, higher voltages can cause EP mediated cell death in a heat independent way.

Figure 5:
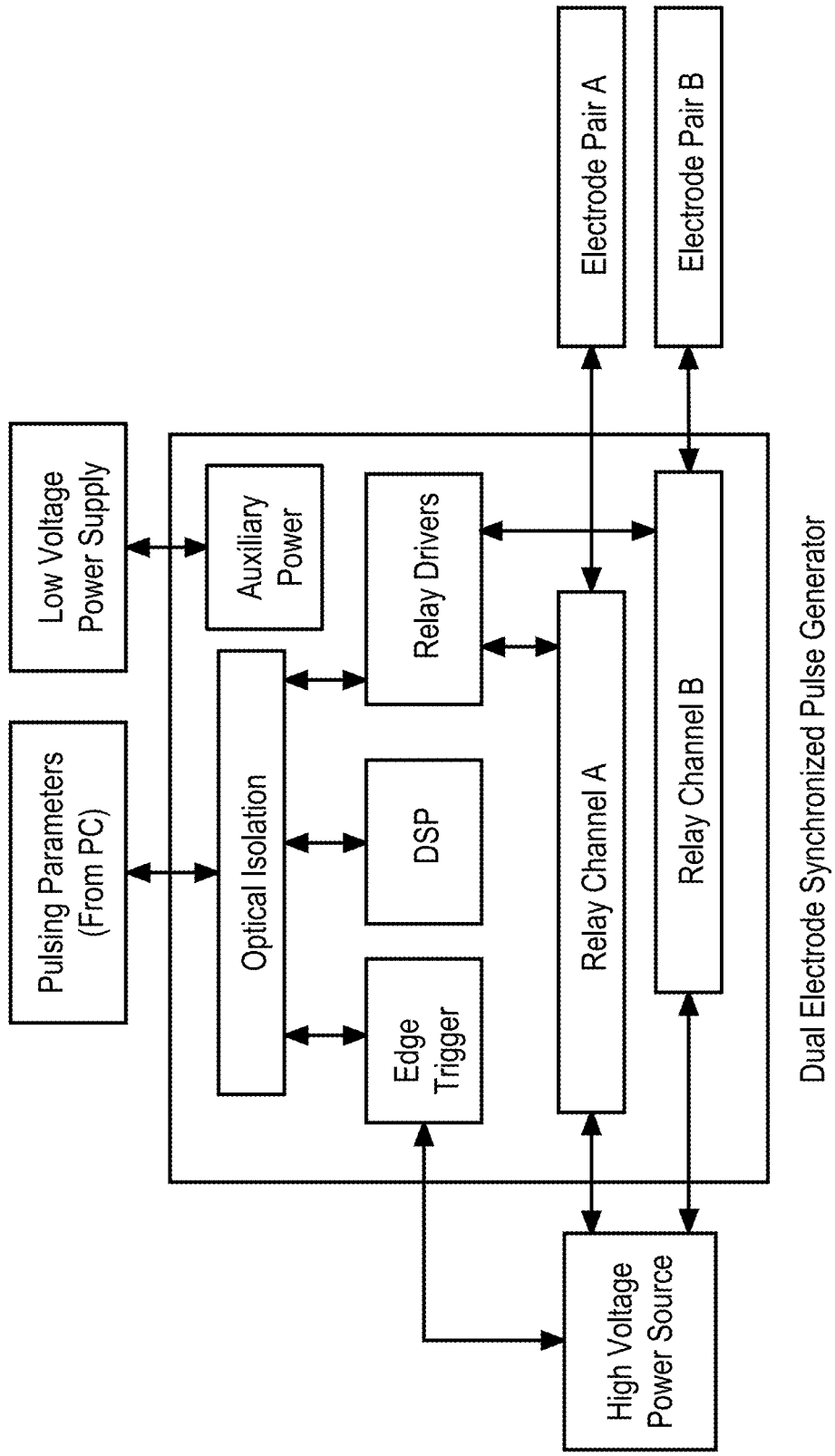
FIG. 5 is an illustration of hardware architecture of an EP generator use for generation of pulsed electric fields to the EPE pairs A and B. The EP device can be based around a digital signal processor (DSP), microprocessor, field programmable gate array (FPGA), application specific integrated circuit, central processing unit (CPU), or any multipurpose programmable device that accepts analog/digital data as an input, processes it according to instructions stored in memory, and provides output as a result. The switching sequence routines of the electrode pairs A and B are programmed and stored in memory. A data bus may be used to display and modify pulsing parameters. High voltage isolation will allow the hardware to be used with the high voltage power supply while plugged into the PC. A low voltage power supply may be used to power all auxiliary circuitry, e.g. EMEs for capacitance and impedance measurements, analog-to-digital converter, digital-to-analog converters, relays, DSP, optical switches, etc.

FIG. 5 is an illustration of hardware architecture of use for generation of pulsed electric fields to the electroporation electrode pairs A and B. The electroporation device can be based around a digital signal processor (DSP), microprocessor, field programmable gate array (FPGA), application specific integrated circuit, central processing unit (CPU), or any multipurpose programmable device that accepts analog/digital data as an input, processes it according to instructions stored in memory, and provides output as a result. The switching sequence routines of the electrode pairs A and B are programmed and stored in memory. A data bus may be used to display and modify pulsing parameters. High voltage isolation will allow the hardware to be used with the high voltage power supply while plugged into the PC. A low voltage power supply may be used to power all auxiliary circuitry, e.g. capacitance or impedance sensing electrodes, analog-to-digital converter, digital-to-analog converters, relays, DSP, optical switches, etc.

In some embodiments, as illustrated in FIG. 5, the first and second pairs of electrodes may further be connected to a generator capable of supplying electric signals at various waveforms for each respective EPE pair. The first pair of EPEs A may be supplied with a waveform of a predetermined phase difference from a waveform supplied to the second pair of electroporation electrodes B by the power supply. For example, the first and second pair of EPEs may receive waveforms which have a phase difference of 180 degrees, as illustrated by the rectangular electrode pair A waveform and electrode pair B waveform shown in FIG. 13. As will be appreciated by those in the art and more fully described below, when EIS, the generator or power supply is capable of delivering both high voltage EP pulses and low voltage interrogation signals, and if not, an additional low voltage EIS power supply is provided.

In some embodiments, highly specialized medical grade fast-switching high-voltage/high current solid-state relays are used to switch the generator from a low voltage EIS mode supplying interrogation signals for EIS to a high voltage EP mode supplying EP pulses for EP, using optically coupled relay drivers. Each relay driver may be connected between the high voltage power supply and a corresponding pair of electroporation electrodes. Each relay channel may be implemented in a push-pull configuration to ensure stray charge is removed from each of the electrode pairs during a turn-off event.

The power supply having the first and second waveform generators may be electrically connected to a solid-state high-voltage relay channel A and relay channel B to control and output the first and second electrical signals, with the first and second waveforms to the respective electroporation electrodes A and B.

B. Therapeutic Delivery System

In some embodiments, the EP devices of present invention may include a therapeutic moiety (TM) delivery system. The TM delivery system may be integrated into EP device in the form of a central probe or channel for delivery of the TM. In some embodiments, as described above, the EPEs may be formed as hollow electrodes with an open distal end for delivery of the TM there through. By "therapeutic moiety" ("TM") herein is meant a moiety suitable for EP that can treat diseased tissues, including cytotoxic agents, chemotherapeutic agents, toxins, radioisotopes, cytokines, or other therapeutically active agent. The TM can be small molecule drugs, nucleic acids (including those that encode therapeutic proteins of interest), or proteins (including polypeptides and peptides) that have biological activity.

In some embodiments, the TM is a drug; drugs contemplated for use in the method of the invention are typically chemotherapeutic agents having an antitumor or cytotoxic effect. Such drugs or agents include bleomycin, neocarcinostatin, suramin, doxorubicin, carboplatin, taxol, mitomycin C, and cisplatin. Other chemotherapeutic agents will be known to those of ordinary skill in the art (see, for example, The Merck Index). EP facilitates entry of bleomycin or other similar drugs into the tumor cell by creating pores in the cell membrane.

In some embodiments, the TM is a nucleic acid. In general, TMs that are nucleic acids are of two different functional types. In one embodiment, the nucleic acids encode proteins that are used to treat the disease; in others, the nucleic acid is the TM, for example when the nucleic acid is siRNA or snRNA. By "nucleic acid" or "oligonucleotide" or grammatical equivalents herein means at least two nucleosides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments, for example when the nucleic acids are siRNA, etc.

In some embodiments, the nucleic acid is DNA or RNA encoding a therapeutic biomolecule, including proteins, including antibodies.

In some embodiments, the nucleic acid encodes an interleukin, which can serve to stimulate the patient's immune system and/or cause cells transformed with the nucleic acids to apoptose or necrose. Suitable interleukins include, but are not limited to, IL-12.

In some embodiments, the nucleic acid encodes a chemotherapeutic antibody. Generally, in this embodiment, there are two nucleic acids that are electroporated into the tissue, one encoding a heavy chain and one encoding a light chain. In some cases, these can be in a single expression vector or two expression vectors can be used.

The term "antibody" is used generally. Antibodies that find use in the present invention can take on a number of formats as described herein, including traditional antibodies as well as antibody derivatives, fragments and mimetics, described below. Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4, with the former finding particular utility in a number of applications, particularly oncology. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

In some embodiments, the antibodies are full length. By "full length antibody" herein is meant the structure that constitutes the natural biological form of an antibody, including variable and constant regions, optionally including one or more amino acid modifications as is known in the art. Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

As will also be appreciated by those in the art, the nucleic acid TMs can be incorporated into plasmids and/or expression vectors, including additional components, including but not limited to expression promoters, In some embodiments, the delivery system may include a wand delivery system configured to deliver TM to the electroporation location. The delivery system may include at least one injection probe defining a first lumen, and the injection probe may be of a cylindrical shape and have a needle tip at an end of the injection probe. The needle tip may be hollow and have an open end for delivering the TM to the electroporation location. In some embodiments, the TM is injected into the middle of the outer periphery defined by the EPEs, and electroporated into the cells in the electroporation location using any of the EP devices described herein.

It should be understood that the EP of tissue can be performed in vitro, in vivo, or ex vivo. EP can also be performed utilizing single cells, e.g., single cell suspensions, in vitro, or ex vivo in cell culture.

The EP wand housing, e.g. wand housing 12 is grasped and the EPEs are inserted into the tissue to the desired depth. Thereafter, a suitable generator or power supply as described herein is connected to the EPEs and the appropriate voltage applied to each of the EPE pairs. A suitable quantity of therapeutic moieties such as genes or molecules of a suitable chemical or pharmaceutical for treatment of the tissue is then injected into the tissue, using the wand delivery system described above, before the EP pulse is applied.

In some embodiments, the delivery system may include at least one injection probe defining a first lumen, and the injection probe may be of a cylindrical shape and have a needle tip at an end of the injection probe. The needle tip may be hollow and have an open end for delivering the therapeutic moieties to the electroporation location. In some embodiments, the therapeutic moieties are injected into the middle of the outer periphery defined by the electroporation electrode pairs A and B, and electroporated into the cells in the electroporation location 110 using the EP devices of the present invention.

C. Electroporation Methods

Various embodiments of the present invention are directed to a method for electroporating cells in an electroporation location of a tissue using an electroporation system, e.g. system 10 (illustrated in FIG. 9) of the present invention. Various embodiments of the present invention are directed to the use of focused pulse addition electroporation. By "focused pulse addition (FPA) electroporation" herein is meant applying short electric field pulses to an electric field zone through at least a first and a second pair of electroporation electrodes to create transitory pores in cell membranes without causing permanent damage to the cells. "Electroporated cells" include those that have transitory pores open in the cellular membrane, which close as the charge on the cell membrane dissipates ("open pore cells"), and those that have undergone electroporation such that the cells now contain the exogeneously added therapeutic moieties and have closed pores (e.g. are intact again).

Figure 2:
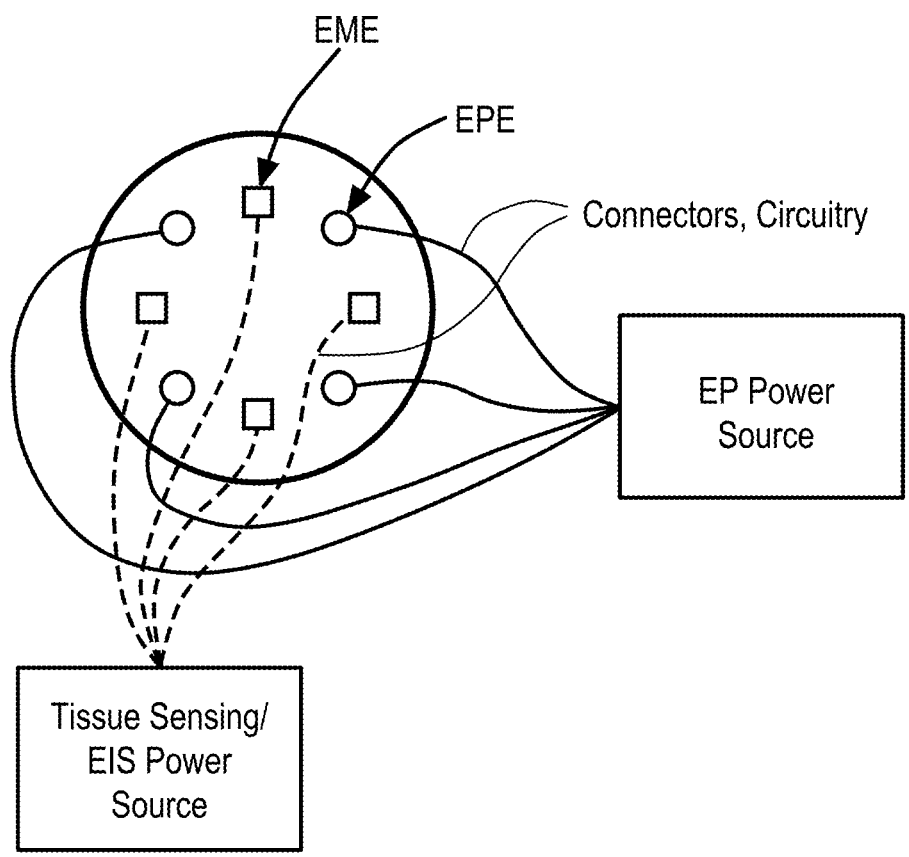
FIG. 2 depicts an EP electrode array of 4 electrodes (two pairs or sets) and an EM electrode array of 4 electrodes (two pairs or sets), each attached via connectors and circuitry to the appropriate power source. Again, each array is a 4 electrode array, although more electrodes can be used. In addition, in these embodiments, where two different electrode arrays are used, the number of electrodes need not be equal in each case; an EP array of 4 electrodes and an EM array of 6 electrodes can be used, etc.

By "pair of electroporation electrodes" herein is meant a pair consisting of two electrodes, which, when connected to a power supply are configured to be oppositely charged. The method may include contacting the electroporation wand housing 12 to the tissue such that the electric field zone 100 is defined by the area encompassed by the electroporation electrode pairs A and B, as illustrated in the figures. The first and second pairs of electroporation electrodes may be stationary or retractable within the electroporation wand housing 12. The electroporation wand housing 12 may further include a circuit board 16 having a plurality of sliding through-sockets through which the electroporation electrodes A and B are slidably retractable and extendable. The electrode pairs A and B are mounted in the electroporation housing 12 which is slidably engaged with an indicator or gage 11. As the electroporation wand housing 12 is moved along the gage 11, it alternately extends and retracts the electrode pairs A and B, as illustrated in FIG. 2. The device indicator or gauge 11 may provide an indication of the length of extension of the electrode pairs A and B. The electroporation system may further include an electrical connector 14 to electrically connect each of the first A and second B electrode pairs to a power supply 18, e.g. a pulse generator. The electrical connector includes four or more conducting wires (depending on the number of electroporation electrodes for transmitting electrical signals from the power supply to the each of the electroporation electrodes. These signals may include needle voltage setpoint, pulse width, pulse shape, the number of pulses, and switching sequence. As will be appreciated by those in the art and more fully described below, the EP electrodes may also serve as CS or EIS electrodes, in which case a second low voltage power supply is used with appropriate switching mechanisms to allow the delivery of higher voltage EP signals and then lower voltage CS or EIS signals.

In some embodiments of the present invention, one or more of the electroporation electrode pairs A and B may be non-penetrating electrodes which may or may not have an open distal end for administering therapeutic moieties to the tissue, as illustrated in FIG. 11. The non-penetrating electrodes could be any suitable shape conductor such as a button or plate to contact the surface tissue. The injectors may be disposed in spaced relation to one another and in close contact with a surface region of the tissue of the subject. The portion of the non-penetrating electrodes in contact with the tissue surface is electrically conductive and electrically connected to the power supply 18 through the electrical connector 14, such that electroporation is accomplished by delivering an electrical current through the region of tissue by completing the circuit between the electrically conducting distal ends of the non-penetrating electroporation electrodes.

Figure 12:
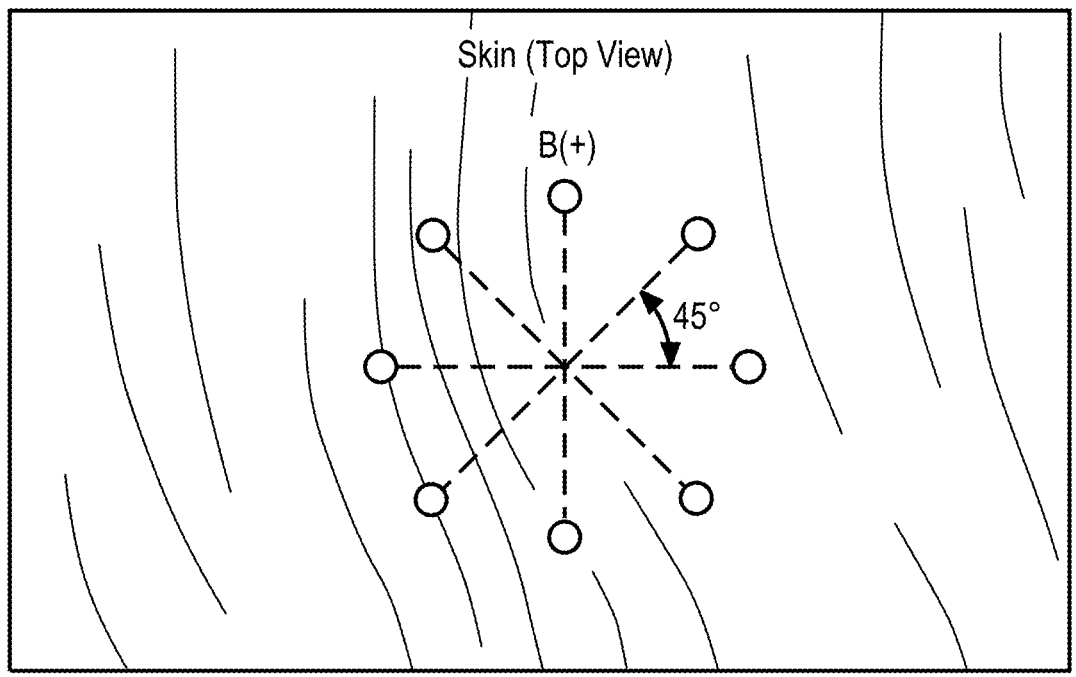
FIG. 12 is a schematic illustration of an offset angle produced by plurality of EPE pairs according to the present invention.

In some embodiments, as illustrated in FIG. 12, more than two pairs of electrodes may be used and the offset angle may be adjusted accordingly. The greater the number of electrodes, the more focused the electroporation location which is crossed by the electric fields of all electrode pairs becomes. Further, a larger number of electrode pairs allows for shorter pulses from each electrode pair, thereby substantially decreasing or even eliminating the cell death and burns around the electrodes in the "burn-out zone".

The tissue surrounding the EP electrodes is sometimes referred to as a "burn out zone". By "burn-out" zone is meant the area occupied by the tissue directly adjacent to and/or in contact with each of the individual electrode. It is referred to as the "burn-out" zone because the cells come in direct contact with the electrodes which are heated as a result of the high voltage signal from the power supply, and thus the cells are subject to damage by overheating. However, by using the alternating pulse systems of the present invention, the damage to the cells in the burn out zone can be minimized by reducing the heat and field by 50% (in the case of two sets of electrodes, more if more sets are used). In addition, as the electric field strength is focused/increased at the electrodes, higher voltages can cause EP mediated cell death in a heat independent way.

Figure 13:
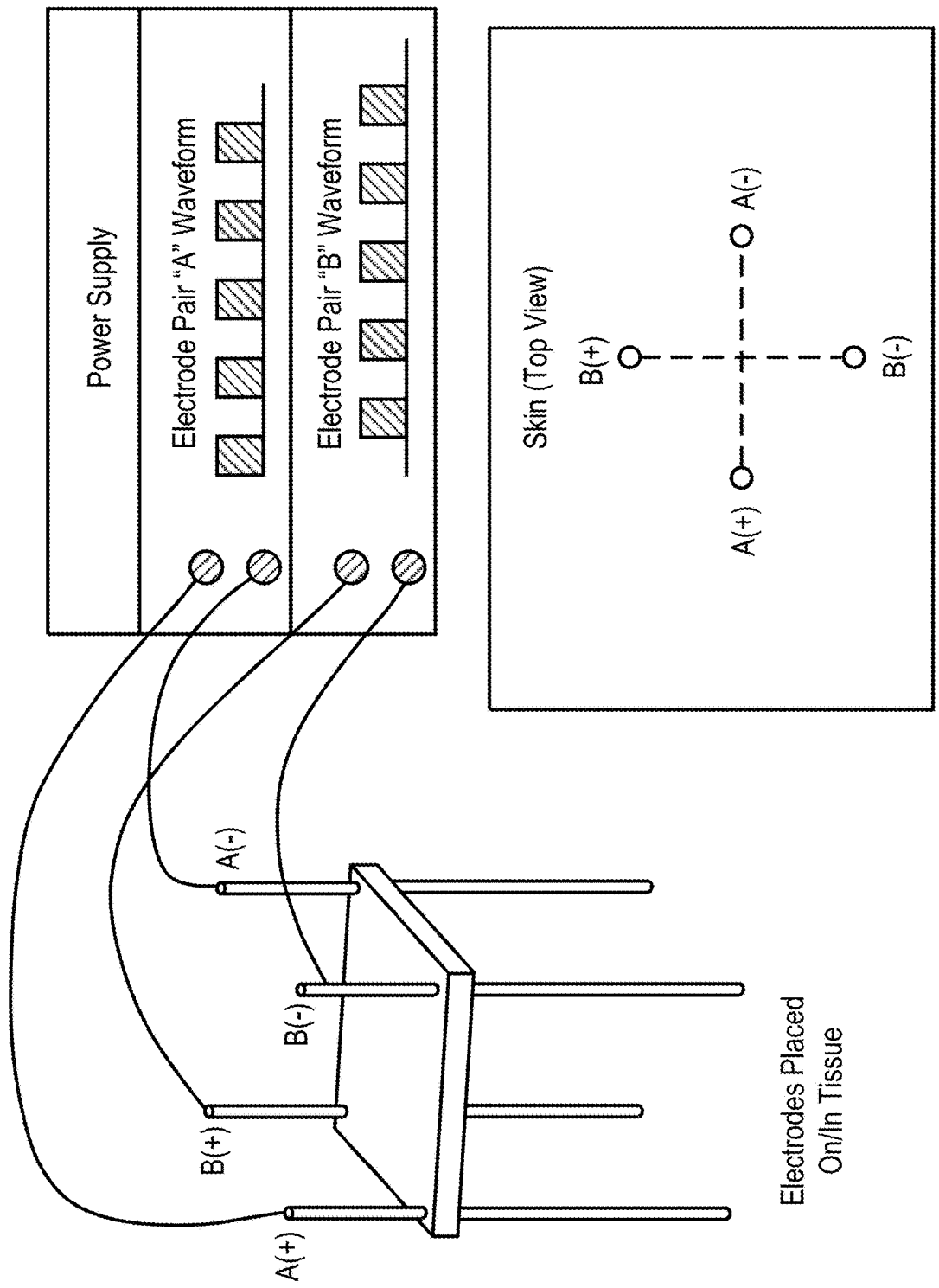
FIG. 13 is an illustration of a first waveform corresponding to the first pair of EPEs, and a second waveform corresponding to the second pair of EPEs, according to the present invention.

In some embodiments, as illustrated in FIG. 13, the first and second pair of electrodes may further be connected to an EP power (EPP) supply capable of supplying electric signals at various waveforms for each respective electroporation electrode pair. That is, the power supply may be a high voltage power supply suitable for waveform generation. The first pair of electroporation electrodes A may be supplied with a waveform of a predetermined phase difference from a waveform supplied to the second pair of electroporation electrodes B by the power supply. For example, the first and second pair of electroporation electrodes may receive waveforms, from a first waveform generator and a second waveform generator of the power supply respectively, which have a phase difference of 180 degrees, as illustrated by the rectangular electrode pair A waveform and electrode pair B waveform shown in FIG. 13 and FIG. 14A and FIG. 14B. As will be appreciated by those in the art and more fully described below, when capacitance sensing is done, a low voltage power supply is optionally used.

The method may include contacting the electroporation wand housing 12 to the tissue such that the electric field zone 100 is defined by the area encompassed by the electroporation electrode pairs A and B, as illustrated in FIG. 10 and FIGS. 14A and 14B. In some embodiments, the electroporation method may further include applying a first signal generated by the from the power supply to the first pair of electroporation electrodes A at a first waveform and applying a second signal from the power supply to the second pair of electroporation electrodes B at a second waveform, in which the first waveform has a predetermined phase difference from the second waveform.

The electroporation system 10 sends multiple, independent electric signals during operation to selected electrode pairs A and B that, when in contact with tissue, can cause electroporation in the cell membrane. When the first and second electrode pairs A and B are in electrical contact with the tissue, the first electrical signal, which has a first frequency and the second electrical signal combine to produce a constant waveform with a frequency and amplitude sufficient to temporarily open pores of the cells for optional introduction of therapeutic moieties into the cells of the tissues without permanently damaging the cells and minimizing pain.

The nature of the tissue, the size of the selected tissue, and its location may determine the nature of the electric signals to be generated. It is desirable that the electric field be as homogenous as possible and of the correct amplitude. An excessive electric field strength may result in death of cells, whereas a low field strength may result in ineffective electroporation of cells, thus a reduced efficiency of delivering agents into the cell.

The method may further include applying a pulsed electric field to the electric field zone 100 from the first pair of electroporation electrodes A, the pulsed electric field being based on the first signal, in which the pulsed electric field and each subsequent pulsed electric field of the first pair of electroporation electrodes A have a voltage and duration lower than a minimum threshold for electroporation. Next, another pulsed electric field is applied to the electric field zone 100 from the second pair of electroporation electrodes B, the other pulsed electric field being based on the second signal, in which the other pulsed electric field and each subsequent pulsed electric field of the second pair of electroporation electrodes B have a voltage and duration lower than a minimum threshold for electroporation.

In some embodiments, the first and second pulsed electric fields are selected from a group consisting of a square wave pulse, an exponential wave pulse, a unipolar oscillating wave form of limited duration, and a bipolar oscillating wave form of limited duration According to the method of the present invention, paths of the pulsed electric fields of the first and second pairs of electroporation electrodes A and B cross at the electroporation location 110, and the application of each pulsed electric field of the first pair of electroporation electrodes to the electroporation location alternates with the application of each pulsed electric field of the second pair of electroporation electrodes to the electroporation location to amount to a continuous pulsed electric field having a voltage and duration sufficient for electroporation being applied to the cells in the electroporation location, as illustrated in FIGS. 14A and 14B.

On the other hand, the application of each pulsed electric field of the first pair of electroporation electrodes to tissue adjacent to the first pair of electroporation electrodes and outside of the electroporation location alternates with a rest period to cause the tissue adjacent to the first pair of electroporation electrodes and outside of the electroporation location to receive an alternating on and off pulsed electric field, from the first pair of electroporation electrodes, having the voltage and duration lower than the minimum threshold for electroporation. wherein the application of each pulsed electric field of the second pair of electroporation electrodes to tissue adjacent to the second pair of electroporation electrodes and outside of the electroporation location alternates with a rest period to cause the tissue adjacent to the second pair of electroporation electrodes and outside of the electroporation location to receive an alternating on and off pulsed electric field of the second pair of electroporation electrodes having the voltage and duration lower than the minimum threshold for electroporation as illustrated in FIGS. 14A and 14B.

Thus, the electroporation method of the present invention yields the advantage that healthy cells outside of the electroporation location but within the electric field zone 100 are subjected to electric pulses for only half of the duration of those in the electroporation location and insufficient for electroporation, these cells sustain minimal to no permanent damage. Further, since the cells outside the electroporation location 110, but within the electric field zone 100 are only subjected to short pulses, this minimizes the extent of damage to the cells directly adjacent to the electroporation electrodes in the "burn-out" zone.

The nature of the tissue, the size of the selected tissue, and its location may determine the nature of the electric signals to be generated. It is desirable that the electric field be as homogenous as possible and of the correct amplitude. An excessive electric field strength may result in death of cells, whereas a low field strength may result in ineffective electroporation of cells, thus a reduced efficiency of delivering agents into the cell.

In some embodiments, the pulsed electric fields are selected from a group consisting of a square wave pulse, an exponential wave pulse, a unipolar oscillating wave form of limited duration, and a bipolar oscillating wave form of limited duration According to various methods of the present invention, as illustrated in FIG. 10, paths of the pulsed electric fields of the first and second pairs of EPEs A and B cross at the electroporation location 110, and the application of each pulsed electric field of the first pair of EPEs to the electroporation location 110 alternates with the application of each pulsed electric field of the second pair of EPEs to the electroporation location 110 to amount to a continuous pulsed electric field having a voltage and duration sufficient for electroporation being applied to the cells in the electroporation location 110, as illustrated in FIGS. 14A and 14B.

V. Preferred Device Embodiments (i) All-in-One EP Device

Figure 18A:
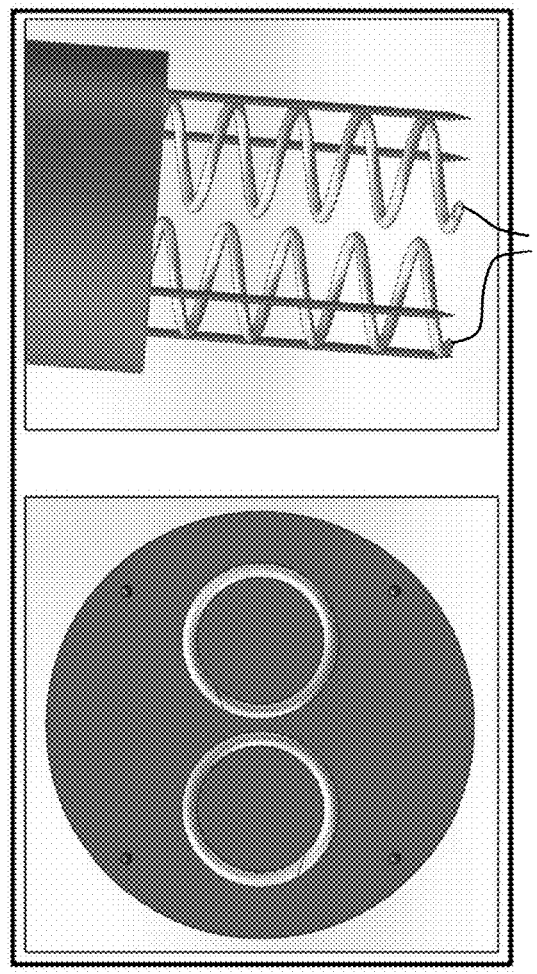
FIG. 18A and FIG. 18B are schematic illustrations of a perspective view and a bottom view of an exemplary EP device with electrodes integrated around injection element and moiety delivery probes for use in the adaptive control system for optimizing electroporation (EP) pulse parameters.
Figure 18B:
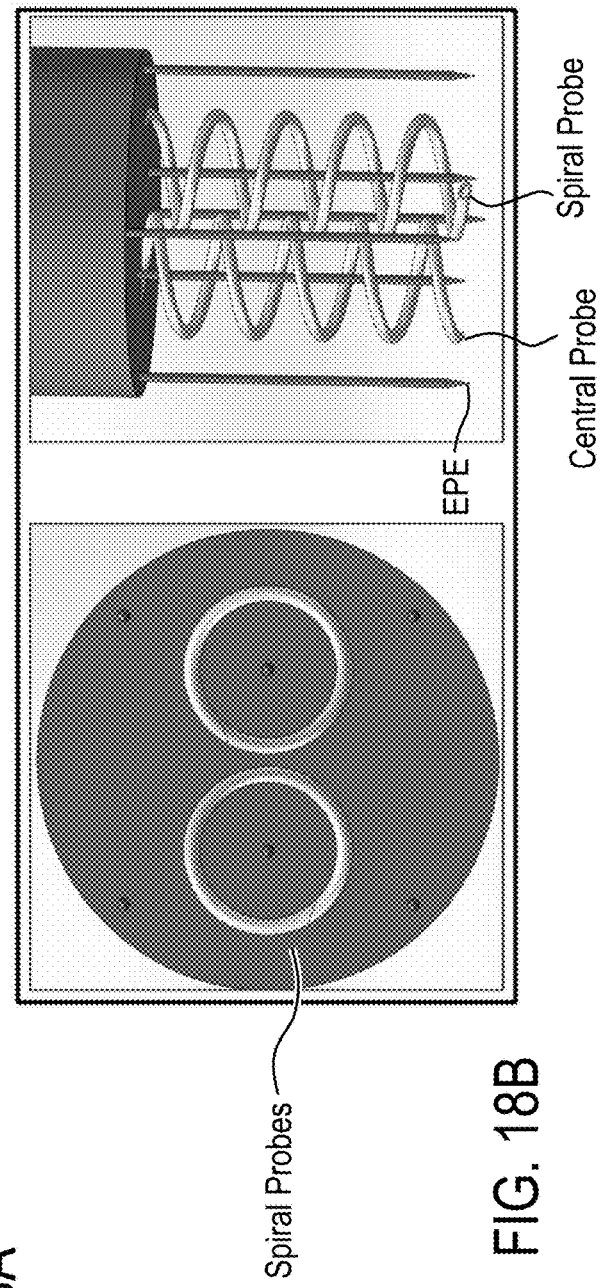

Accordingly, the present invention provides apparatuses and methods for the improved delivery of therapeutic moieties to cells in a tissue of a patient. An all-in-one device for improved delivery of therapeutic moieties to cells in a treatment zone of a tissue is described. The device includes at least a spiral probe 1702 with an inner surface, in some embodiments, the spiral probe may be a central probe, as illustrated in FIG. 17A and in some embodiments, may include at least one additional probe 1702, as illustrated in FIGS. 18A and 18B. Each of the central probes and additional probes may define one or more central lumens 1704 (e.g., a first central lumen).

The first central lumen 1704 extends from a proximal end 1706 to a distal end 1708 of the central probe 1702. In some embodiments, the proximal end of the central probe may be formed of or coated with a non-conductive material to prevent or reduce generation of electrical fields at the proximal end. The proximal end 1706 of the central probe 1702 may define an opening to fluidly connect the central lumen with a lumen of an injector through which the therapeutic agent may be delivered to the central probe 1702. In some embodiments, the distal end 1708 of the central probe also defines an opening for delivery of the therapeutic moieties into the tissue. Alternatively, the distal end 1708 may be closed, as illustrated in FIGS. 22A-22C. A portion or portions of the distal end of the central probe 1702 may have a shape configured to pierce the tissue.

The central lumen 1704 or portions of the central lumen include a spiral geometry configured to enhance anchoring of the central probe in the tissue and to create a channel 1734 for delivery of the TM to the tissue via ejection ports positioned on the central probe 1702. For example, the portions of the central probe 1702 may include one or more ejection ports 1710 positioned along the geometry, e.g. as illustrated in FIG. 17B.

In some embodiments, the central probe 1702 may be housed at least partially in an applicator 1712. The applicator may include a distal end through which the portion of the central probe extends to an outside of the applicator 1712 to contact the tissue and to retract back into the applicator 1712. For example, the EP device may include an actuator to advance the central probe 1702 toward and through the distal end of the applicator and through the tissue 1714.

One or more diameters defined along the inner and/or outer surface of the central probe may be adjustable to change a distribution and volume of the delivered therapeutic moieties. Similarly, a spiral diameter and a pitch of the central probe are adjustable to change a distribution and volume of said delivered therapeutic moieties.

In some embodiments, the EP device may also include an electrical connector 1716 for electrically coupling or connecting the central probe 1702 to a power source. The electrical connector may be included or housed in a handle 1718.

In some embodiments, the EP device may also include an electroporation system including two or more oppositely charged electroporation electrodes (EPE) 1720. The two or more electrodes are configured to be positioned such that they substantially surround the treatment zone 1722 during treatment. The electrodes 1720 are adapted to extend from proximal to distal ends. On or more of the tips 1724 of the distal ends of the electrodes include a needle shape for piercing the tissue. The electrodes may be coupled to an electrode power supply (e.g. the generator A illustrated in FIG. 16 to cause the electrodes to receive one or more electrical waveforms from the power supply, for supplying an electric pulse 1730 to create a pulsed electric field sufficient for electroporation as illustrated in FIG. 14A to the treatment zone 1722.

Similar to the central probe, the electrodes may be housed in the applicator. The electrodes 1720 may be positioned around the central probe 1702 and configured to be deployed from the applicator 1712 to the treatment zone 1722. For example, the electrodes may be advanced toward the treatment from the applicator and retract into the applicator.

In some embodiments, the advancement and retraction of the electrodes may be powered by a power supply interface included in the handle 1718. For example, the power supply interface may supply power to actuate the extending and retracting of the central probe 1702 and the EPEs 1720.

Figure 19:
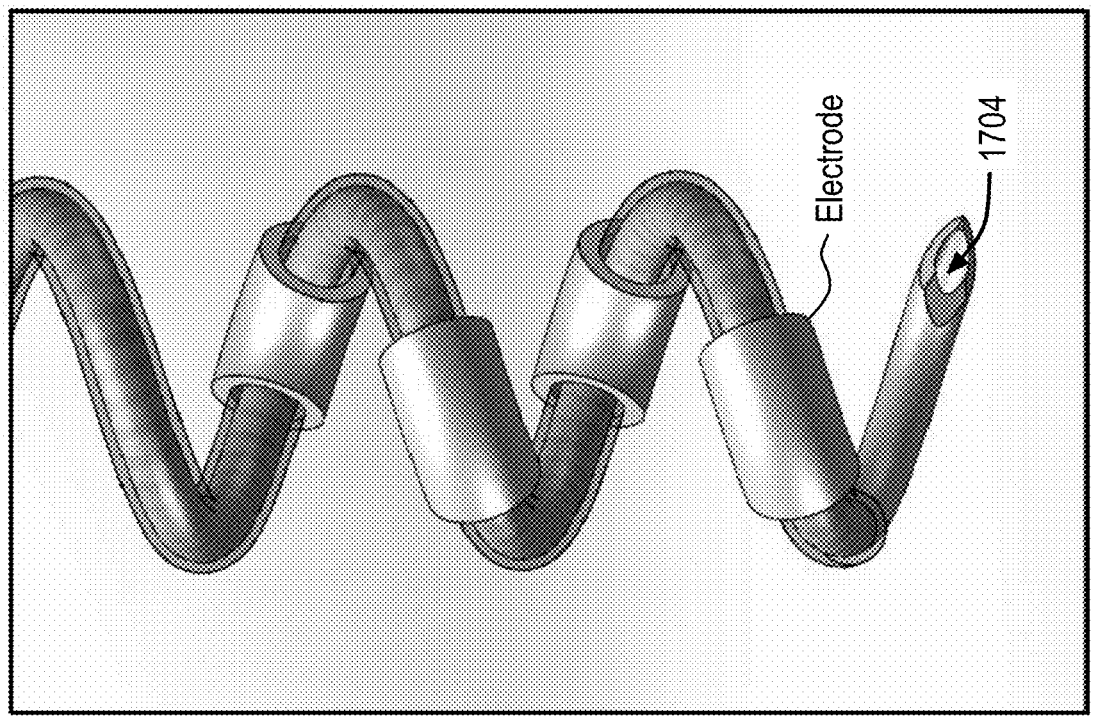
FIG. 19 is a schematic of a plurality of electrodes positioned on a spiral moiety delivery probe of an EP device according to the present invention.

In other embodiments, as illustrated in FIG. 19, the central probe 1702 may include electrodes positioned on the spiral geometry of the central probe 1702. In these embodiments, the electrodes may be integrally formed with the central probe 1702 or may be removably disposed thereon. The electrodes on the central probe 1702 may be used in combination with the electrodes 1720 to generate desired electric field configurations.

Figure 20A:
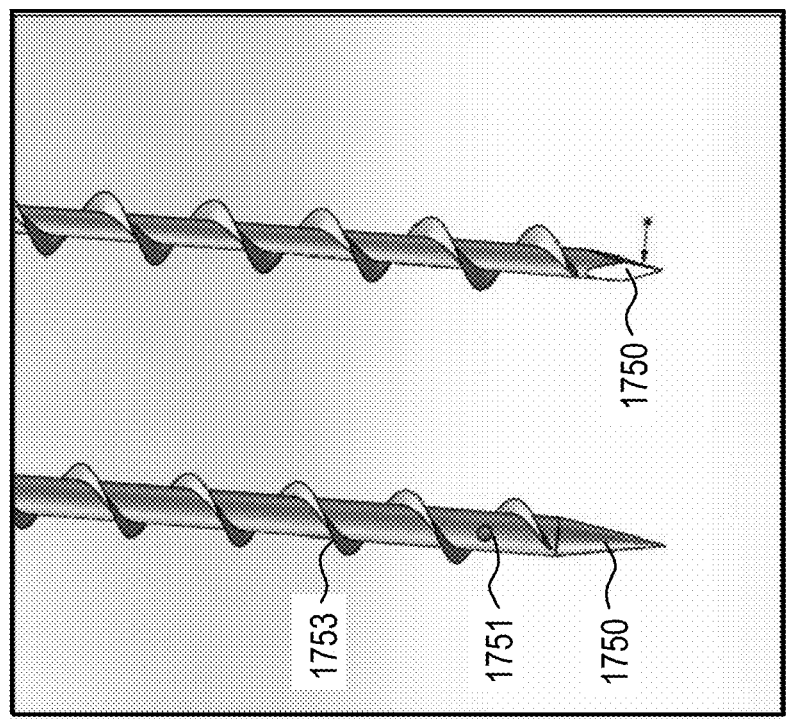
FIG. 20A is an illustration of a plurality of central injection probes of an EP device each including a spiral blade for creating a channel according to the present invention.
Figure 20B:
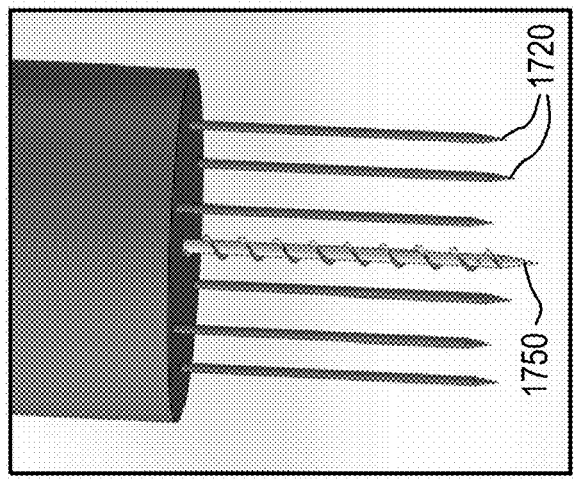
FIG. 20B is a schematic view of an EP device having the central injection probe of FIG. 20A surrounded by a plurality of electrodes.
Figure 20C:
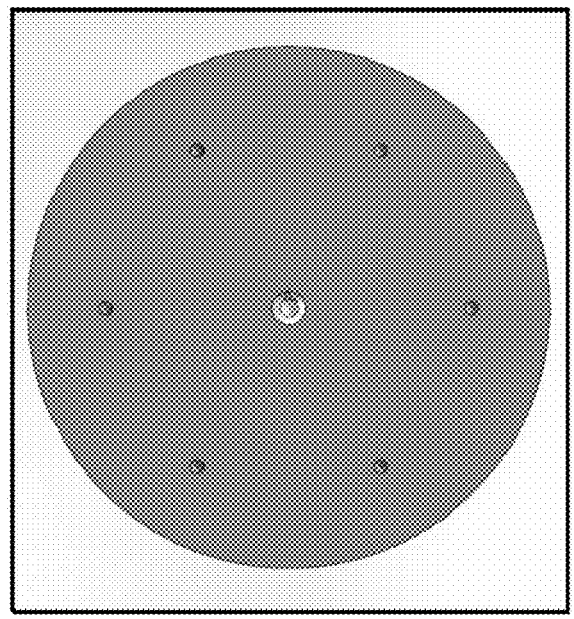
FIG. 20C is a bottom view illustration of FIG. 20B.
Figure 23A:
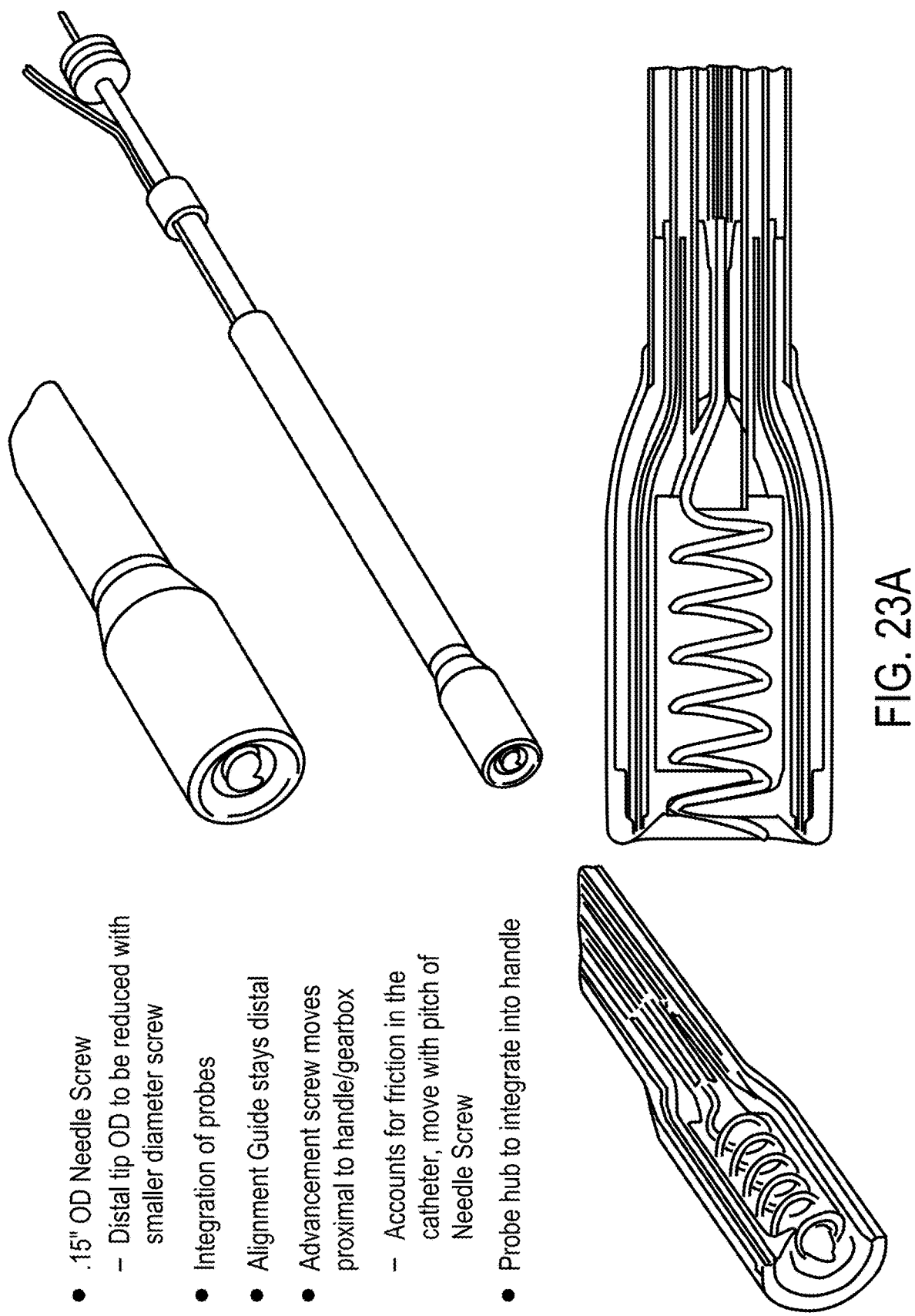
FIG. 23A, FIG. 23B, and FIG. 23C, FIG. 23D, FIG. 23E, and FIG. 23F illustrate a variety of EP devices according to the present invention.
Figure 23B:
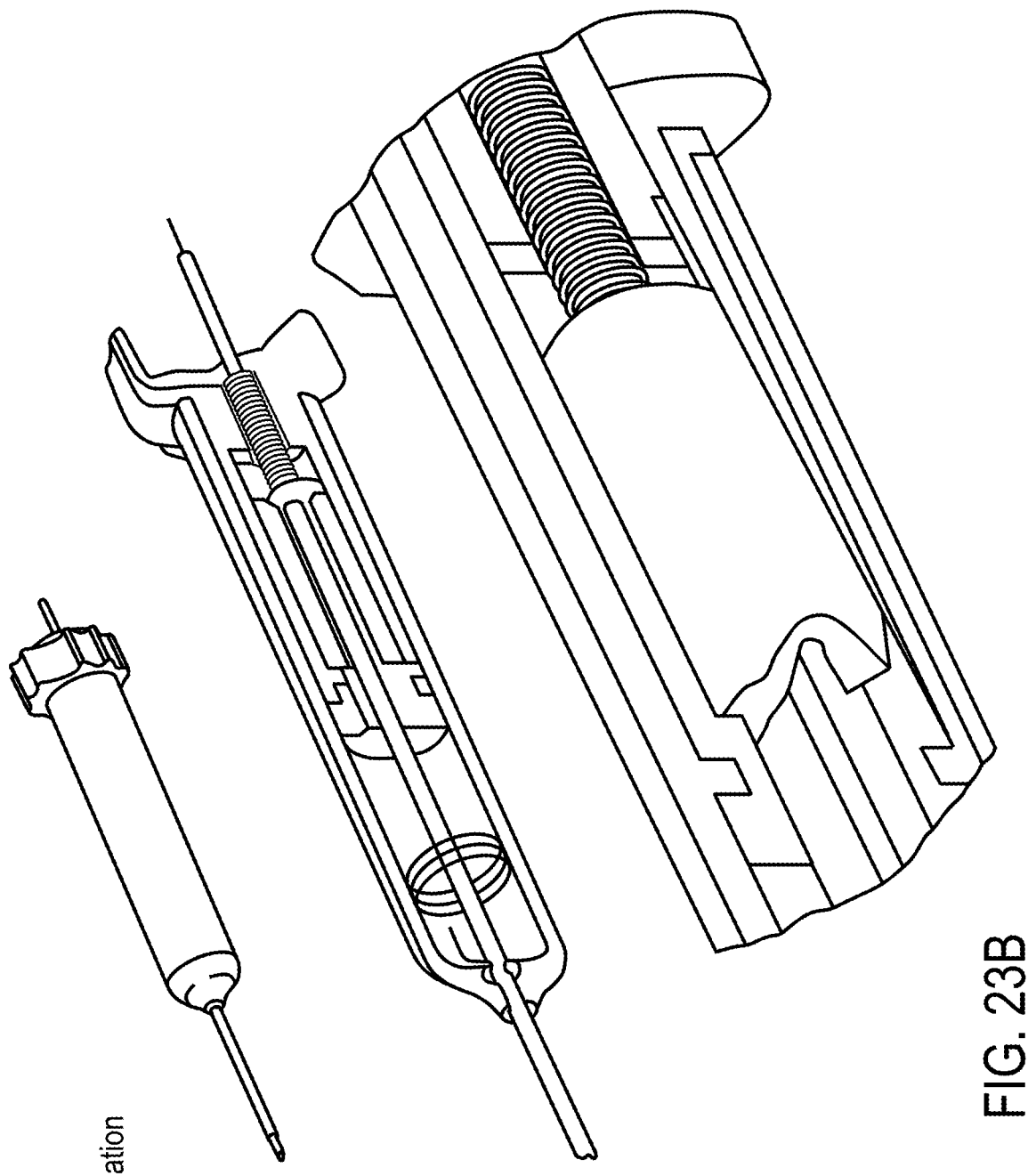
Figure 23C:
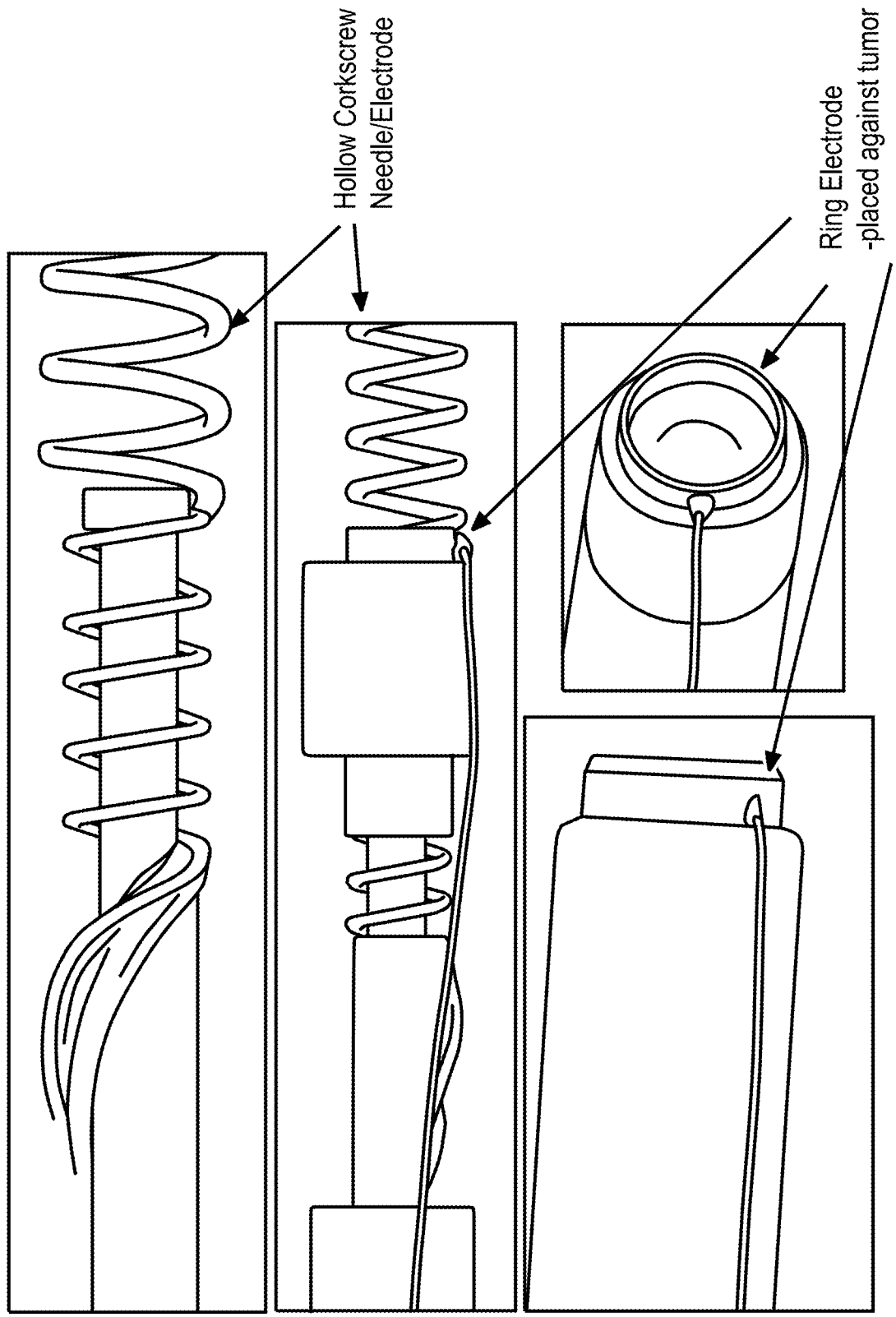
Figure 23D:
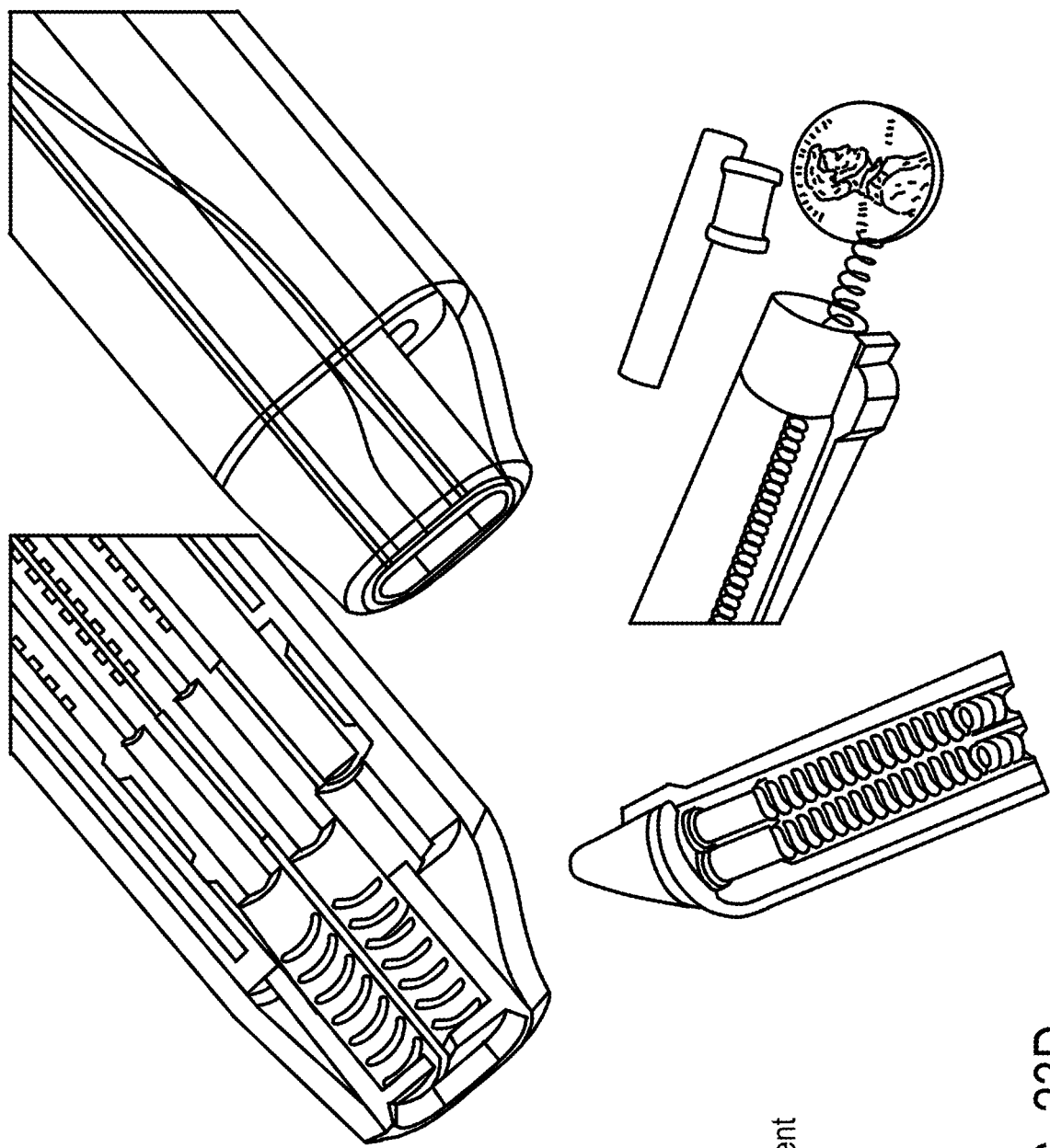
Figure 23E:
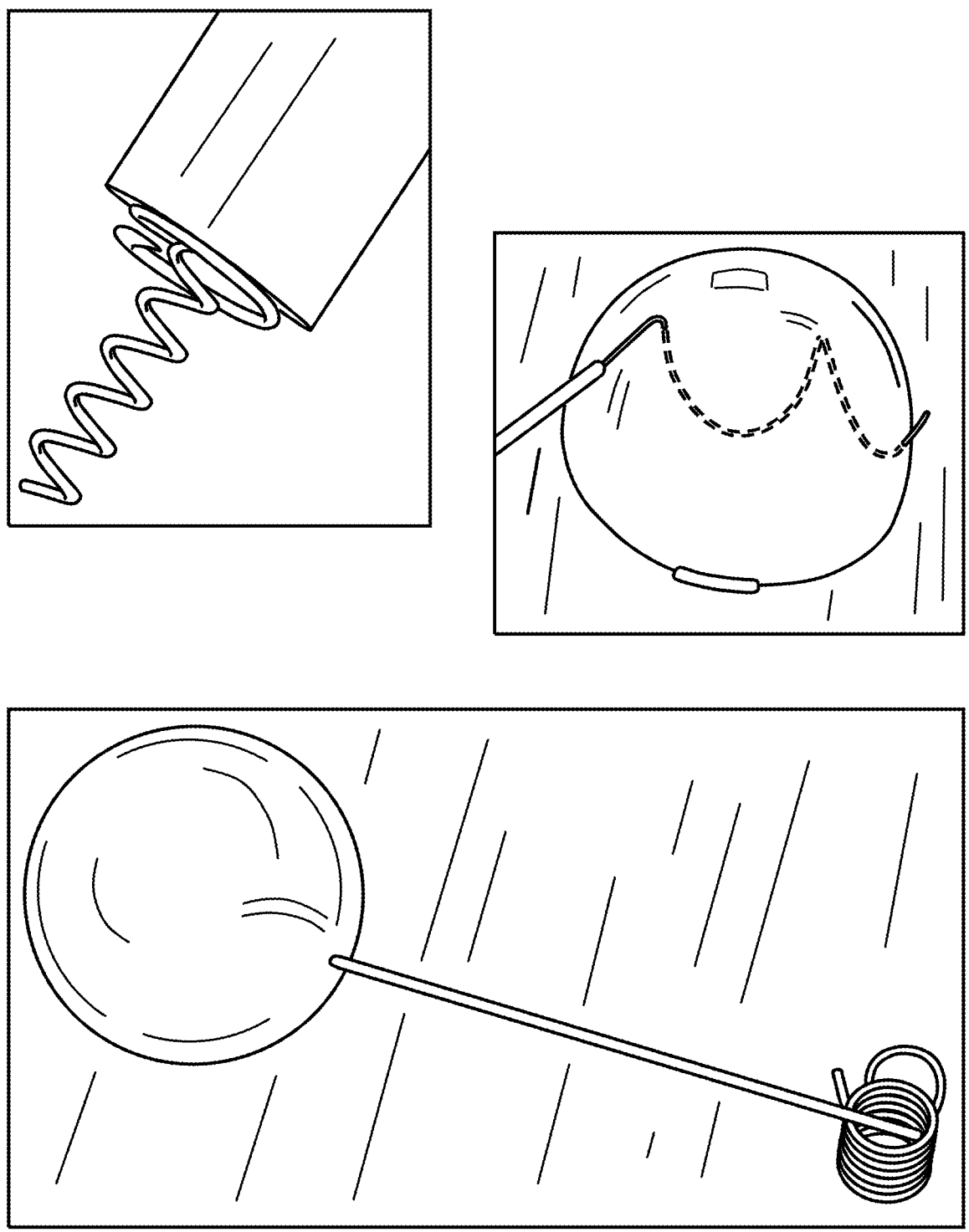
Figure 23F:
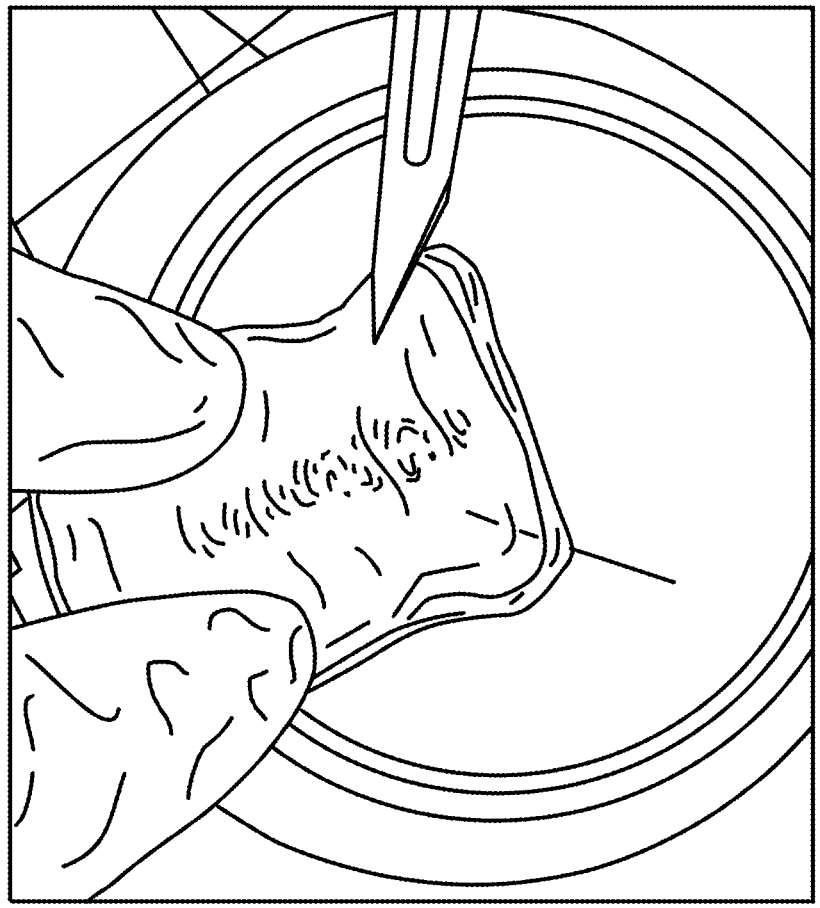

In other embodiments, as illustrated in FIGS. 20A and 20B, the central probe may be an electrode probe 1750 connected to the electrode power supply, e.g., generator A of FIG. 16, such that an electric field is generated between the central probe 1750 and the EPEs 1720 to facilitate electroporation. In some embodiments, as illustrated in FIG. 20A the central probes 1750 may include a spiral blade for creating a channel and for better anchoring of the central probe 1750 in the tissue. FIG. 20B is a schematic view the central 1750 surrounded by a plurality of electrodes 1720, and FIG. 20C is a bottom view illustration of FIG. 20B.

The one or more central probes may include a second spiral probe similarly defined as the central probe 1720 herein. In this case, the second probe offers a second channel for delivery of the therapeutic moieties to the tissue.

Figure 21:
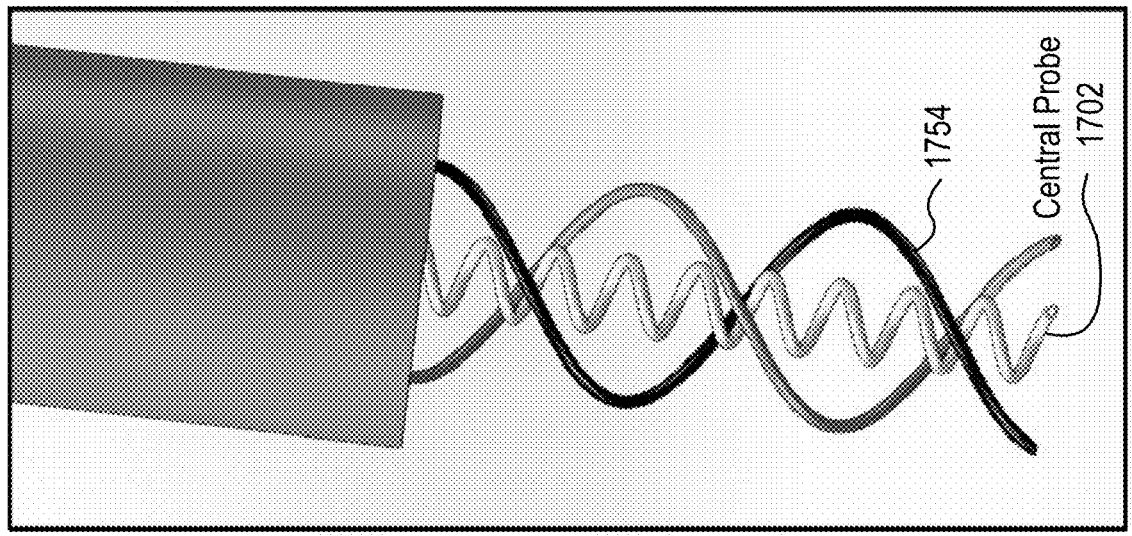
FIG. 21 illustrates an EP device having a spiral central probe and spiral electrodes according to the present invention.

In some embodiments, as illustrated in FIG. 22A, one or more distal electrodes 1752 may be positioned at the distal end of the applicator 1712. These distal electrodes 1752 may be configured to generate an electric field with a portion or portions of the central probe 1702. The one or more distal electrodes may be configured based on a ring configuration, a straight wire configuration, a spiral wire configuration or a collapsible hoop configuration. As noted, the device may include ejection port(s) on one or more portions of the central probe. The distal electrodes may be configured to be positioned external to the tissue to externally generate the electric field to which the tissue is subjected. Alternatively, the distal electrodes 1752 may be configured to be positioned below the surface of the tissue. In some embodiments, as illustrated in FIG. 21, the distal electrodes 1754 may be formed based on the spiral wire configuration such that the spiral wire electrodes are positioned below the surface of the tissue. The spirals of the central probe 1702 and the spirals of the distal electrodes 1754 may be wound in opposing directions, as illustrated in FIG. 21.

In some embodiments, the electrodes described herein (including the distal electrodes) are housed in the applicator 1712 around the central probe 1702 such that they can be deployed from the applicator 1712 accordingly to substantially surround the treatment zone.

In other implementations, one of the probes does not include a spiral geometry. For example, one of the probes is a straight probe having open proximal and distal ends for delivery of the therapeutic moieties to the tissue. A vertical axis of the straight probe is coaxially aligned with a center axis of a diameter of the central probe. The straight probe may be configured to generate an electric field with portion(s) of the central probe. The central probe with the spiral geometry may be configured to transmit acoustic energy received from an acoustic horn mounted to the distal end of the applicator.

a. Sensor System

In some embodiments, the present invention may include a sensor system. As will be appreciated by those in the art, successful electroporation occurs when the cellular membrane is disrupted, resulting in a change of capacitance. When subjected to an electric field, cells generally act as capacitors. When the electric field is applied for a long enough period (depending on the cell properties, health, size, etc. . . . ) charge accumulates at the cell membrane until it reaches a certain threshold and causes a breakdown of membrane integrity. The capacitance sensor system may be a low voltage interrogation or excitation circuit, may include a pair of capacitance sensing electrodes powered by a low voltage power source, a voltage sensor, a current sensor and an electronic signal processing device to process the voltage and current to determine an average capacitance for cells in the zone.

In these embodiments, the sensor system is for performing impedance measurements of cell membranes of the tissue and includes a pair of capacitance sensing electrodes (e.g. electrode 1720) powered by a low voltage power supply (e.g. generator A illustrated in FIG. 16). The sensor system may further include a voltage sensor (integrated into electrodes 1720, 1752 and/or 1754) configured to sense a voltage or voltage drop across the cell membranes. In addition, the sensor system may include a current sensor (integrated into electrodes 1720) configured to sense a current across the cell membranes and an electronic signal processing device, e.g. a controller 1505, illustrated in FIG. 15. The electronic signal processing device (e.g. controller 1505) processes the voltage drop and the current across the cell membranes to determine the impedance of the cell membranes.

In some embodiments, methods for sensing impedance (EIS), described above, may include applying waveforms such as phase locked loops, square wave pulses, high frequency pulses, chirp pulses, etc. as is more fully described below. When exposed to an electric field, cell membranes act as capacitors. Capacitance may be measured based on charge redistribution in the cells in response to low frequency electric field excitations of the low voltage interrogation circuit, and from the capacitance, impedance measurements may be derived. Capacitance may be measured before, between and after electroporation electric fields are applied to determine cell conditions, including, but not limited to cell health, placement of electrodes relative to cells for optimum electroporation, and most importantly a time constant which can be used to determine pulse width of electric fields to be applied to the cells in the electric field zone. In general, charging a capacitor to its maximum, i.e. right before electroporation occurs, takes a period of five time constants, therefore the pulse width of the initial electroporation electric field pulse may be set to 5 times the time constant. This pulse width is insufficient to cause electroporation in the cells which are outside of the electroporation location, as described above, but sufficient to cause electroporation in the cells of the tissue in the electroporation location which is subjected to the additive effects of the electric fields from all sets of electroporation electrodes being applied as one continuous electric field. Capacitance measurements may be repeated after the first electroporation electric fields have been applied, and a percentage drop in capacitance may be calculated and compared to a predetermined value to determine whether cells in the electroporation location have been electroporated sufficiently. If not, pulse width may be adjusted—based on the calculated percentage drop in capacitance—for the next set of electroporation pulsed electric fields until it is determined sufficient electroporation has occurred in the electroporation location.

The electronic signal processing device (e.g. controller 1505) may fit the tissue impedance data to the equivalent circuit model, CPE-based Tissue Model described above in order to predict the next optimal pulsing parameters. As described above, electrical impedance is the sum of these resistive and capacitive elements over a range of frequencies, therefore to quantify each of these parameters, tissue impedance data can be fit to the CPE-based Tissue Model. Therefore, capacitance measurements taken between pulses by the electrodes 1720, 1752 and 1754 with the integrated sensors allows for electrical conditions, e.g., pulse width to be adjusted based on time constants associated with cell membrane capacitance, and the electroporation process can be stopped when an ideal drop in capacitance or membrane integrity is reached. It is hypothesized that real-time monitoring of electrical properties of tissues will enable feedback control over EP parameters and lead to optimum transfection in heterogeneous tumors. Using EIS feedback, will allow (1) delivery parameters to be adjusted in real-time, (2) delivery of only the pulses necessary to generate a therapeutic response, and (3) reduce the overall EP-mediated tissue damage.

b. Therapeutic Moiety Delivery Methods

Various embodiments of the present invention are directed to a method for delivering therapeutic moieties to cells in a treatment zone of a tissue using a delivery device with is integrated into the EP device with the electrodes, e.g. central probe 1702 with ejection port 1710, or central probe 1750 with ejection port 1751. In some embodiments, a method for delivery of therapeutic moieties to the treatment zone of the tissue, may include providing the EP device with the central probe as the delivery device. In some embodiments, the delivery device includes a central probe 1702, 1750 having an inner surface defining at least a first central lumen and extending from a proximal end to a distal end of the central probe 1702, 1750. In some embodiments, at least a portion of the delivery device 1702 has a spiral geometry configured to enhance anchoring of the delivery device 1702 in the tissue and to create a channel for delivery of the therapeutic moieties to the tissue. The portion of the central probe delivery device 1702 may have a plurality of ejection ports positioned along the spiral geometry, in which the proximal end of the central probe delivery device 1702 is open and fluidly connects the central lumen to which the therapeutic agent is delivered, to the cells or tissue. The distal end of the central probe delivery device 1702 is open to define an opening/ejection port 1710 for delivery of the therapeutic moieties into the tissue and has a shape configured to pierce the tissue.

In other embodiments, the central probe delivery device 1750, illustrated in FIGS. 20A-20C, has straight tube shape including blades 1753 having a spiral geometry configured to enhance anchoring of the delivery device 1750 in the tissue and to create a channel for delivery of the therapeutic moieties to the tissue. At least a portion of the central probe delivery device 1750 may have at least one ejection port 1751 positioned thereon to fluidly connect the central lumen to which the therapeutic agent is delivered, to the cells or tissue.

The method further includes contacting the central probe to a diseased cell in the treatment zone of the tissue, actuating and extending the central probe delivery device 1702, 1750 from the applicator in an axial direction, piercing the tissue with at least a portion of the central probe delivery device 1702, 1750 and creating an opening through which at least a portion of the central probe enters the tissue to create a fluid channel for delivery of the therapeutic moieties to the tissue, injecting the therapeutic moieties into the central lumen and delivering the therapeutic moieties to the tissue through the at least one ejection port 1751 and the open distal end of the central probe.

In some embodiments, the method further comprises providing the electroporation system or device comprising at least two oppositely charged electroporation electrodes, e.g. electrodes 1720 configured to be positioned surrounding the zone of tissue, in which the electroporation electrodes are adapted to extend from proximal to distal ends, tips of the distal ends having a needle shape, configured to pierce the tissue and the electroporation electrodes are adapted to be coupled to the power source. The method further comprises contacting the zone of the tissue with the electroporation electrodes, delivering an electric pulse to the electrodes from the power source, and applying a pulsed electric field to the zone which is sufficient for electroporation from the electroporation electrodes.

In some embodiments, a method for delivery of therapeutic moieties to a treatment zone of a tissue comprises providing a device for delivery of therapeutic moieties to the treatment zone of the tissue. The method further comprises contacting the central probe e.g., 1702 and the distal electrode 1752 to a diseased cell in the treatment zone of the tissue, actuating and extending the central probe 1702 and the distal electrode 1752 from the applicator in an axial direction, piercing the tissue with the distal electrode 1752 and with at least a portion of the central probe 1702 and creating an opening through which at least a portion of the central probe enters the tissue to create a fluid channel 1734 for delivery of the therapeutic moieties to the tissue, injecting the therapeutic moieties into the central lumen 1704 and delivering the therapeutic moieties to the tissue through at least one of the ejection port and the open distal end of the central probe, delivering an electric pulse to the distal electrode and the central probe from the power source, applying a pulsed electric field to the zone which is sufficient for electroporation from the distal electrode and the central probe and retracting the distal electrode 1752 and the central probe 1702 from the tissue.

In some embodiments, as described above, the method for delivering therapeutic moieties to the zone may further include coupling the EPEs to a power source, contacting the zone of tissue with the EPEs, delivering an electric pulse to the electrodes from the power source, and applying a pulsed electric field to the zone of tissue which is sufficient for electroporation from the EPEs. The present embodiment adds an advantage to the delivery methods of the present invention of opening the pores of the cells, thereby allowing the cells to absorb greater volumes of therapeutic moieties and yield better results for treatment.

In some embodiments, the pulsed electric fields are selected from a group consisting of a square wave pulse, an exponential wave pulse, a unipolar oscillating wave form of limited duration, and a bipolar oscillating wave form of limited duration.

In some embodiments, as described above, the method for delivering therapeutic moieties to the zone may further include providing a capacitance sensing system and method in conjunction with the electroporation system and method for optimization of electroporation parameters, as described in further detail below. When exposed to low frequency, low strength electric fields, cells generally behave as insulating structures surrounded by ionic clouds that compensate fixed charges present in the membranes. An electric field polarizes the ionic cloud and produces electric dipoles which cause the cells to act as capacitors. Healthy cells act as stronger capacitors than dead or diseased cells with compromised membrane structures, thereby resulting in stronger capacitive coupling between the cells and the capacitance sensing electrodes. Thus, these properties may be utilized as an indication of membrane integrity of cells, which in turn would yield a determination of degree of electroporation of cells.

The method for delivering therapeutic moieties to the zone of tissue may further include sensing cell membrane capacitance of tissues in order to optimize the electroporation process.

In some embodiments, the method of the present invention may include contacting the tissue in the zone of tissue with the pair of capacitance sensing electrodes, e.g., 1720. The low voltage power supply (e.g., generator A) electrically connected to the capacitance sensing electrodes is used to apply a low voltage interrogation signal to the capacitance sensing electrodes. Methods for sensing the capacitance may include but are not limited to waveforms such as phase locked loops, square wave pulses, high frequency pulses, and chirp pulses. A voltage sensor and a current sensor are used to sense a voltage drop and current flowing through the circuit, and these parameters may then be processed by an electronic signal processing device to determine an average capacitance for all cells in the measured area. As described above, capacitance measured is an indicator of how healthy the cells are, and used to determine how long an electric pulse to apply in order to disrupt the cell membrane and provide conditions sufficient for electroporation.

FIG. 23A, FIG. 23B, and FIG. 23C, FIG. 23D, FIG. 23E, and FIG. 23F illustrate a variety of EP devices having a central probe with a spiral geometry as described above, according to the present invention.

(ii) Trocar Based Device EP Device

Figure 24A:
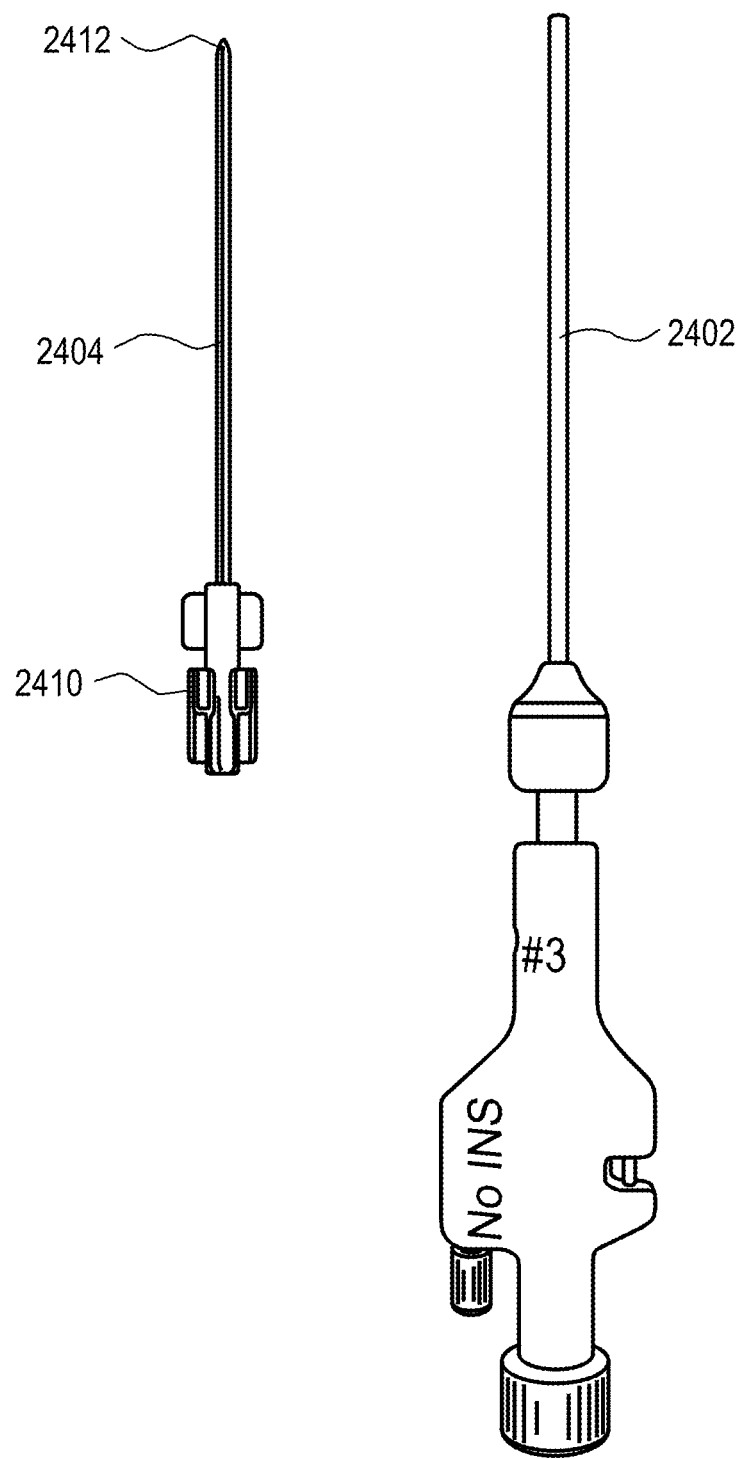
FIG. 24A, FIG. 24B, and FIG. 24C illustrate a trocar-based direct stick applicator EP system according to the present invention.
Figure 24B:
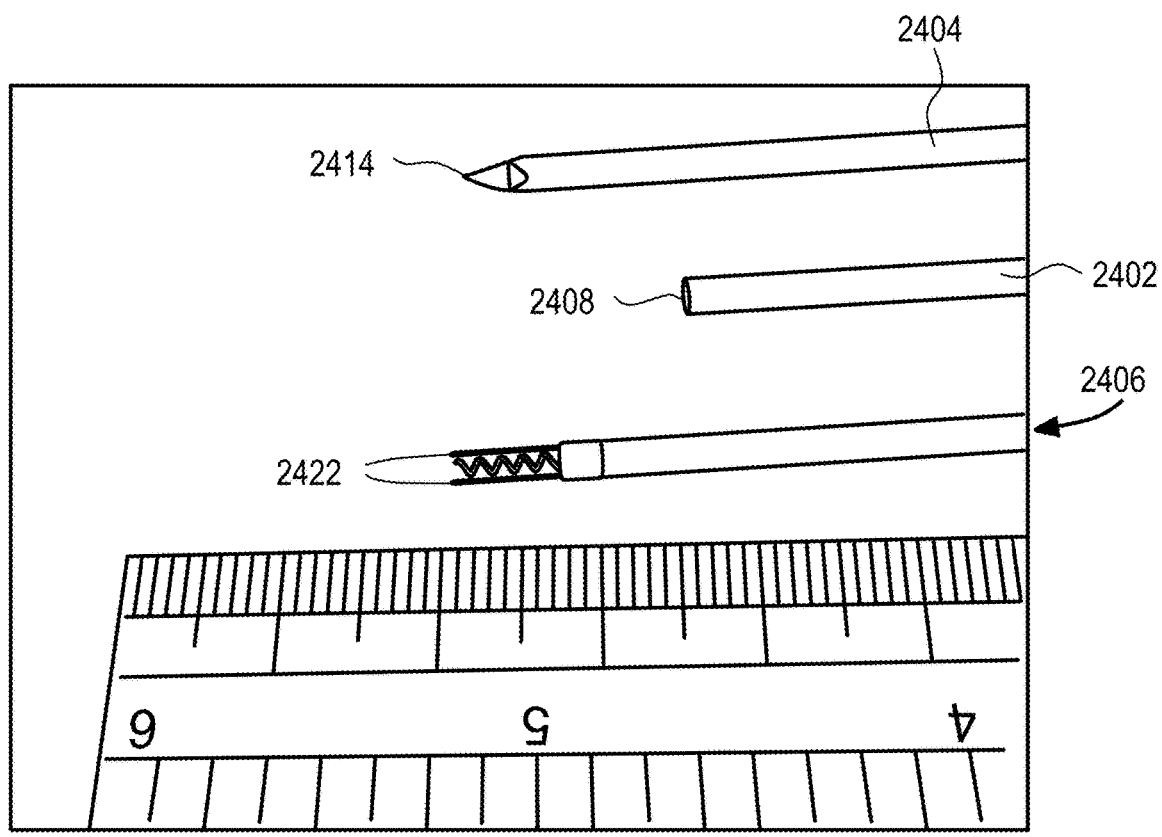
Figure 24C:
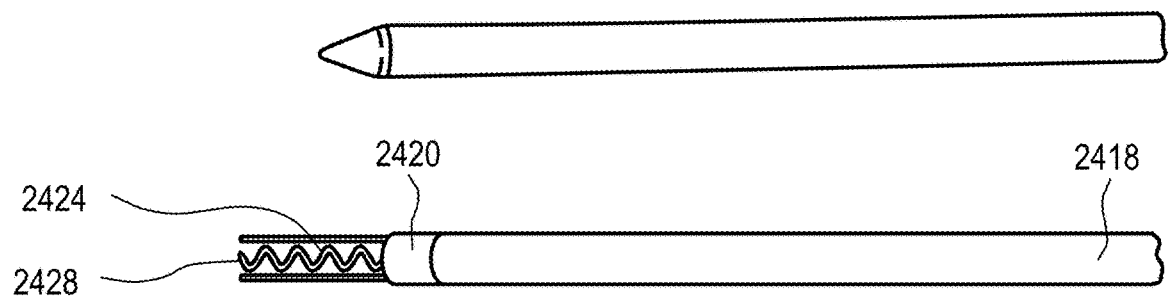

Accordingly, the present invention provides systems for improved EP to cavities within the body which are not easily accessible. FIG. 24A, FIG. 24B, and FIG. 24C illustrate a trocar-based direct stick applicator EP system according to the present invention. The trocar-based direct stick applicator EP system device design allows immunotherapeutic gene delivery to tumors inaccessible to cutaneous electroporation devices. Examples of such cases are where a lung, liver, breast, or any tumor is more than 10 cm below the skin. The EP system provides advantages of improved co-localization of DNA and electric fields for efficient gene delivery and reduction of user induced variability.

In some embodiments, the system for electroporation (EP) of cells in a tissue of a subject, may include a trocar including a cannula 2402 and an obturator 2404, and an EP device 2406 slidably mountable and retractable within the cannula 2402 to access cells or tissue. In some embodiments, the cannula 2402 extends from a proximal end to an open distal end 2408 and defines a first lumen configured to receive the obturator 2404, and the obturator extends from a proximal end 2410 to a distal end 2412. The proximal end of the obturator may include a handle mounted thereon, and the distal end of the obturator may include a blade or a sharp end 2414 configured to pierce through skin, penetrate into body cavities and form a path through which the cannula 2402 may be at least partially inserted into the body cavity. In some embodiments, the obturator 2404 is configured to be slidable within the first lumen, and the distal end 2412 of the obturator is configured to extend to an outside of the first lumen through the open distal end of the 2402 cannula.

In some embodiments, the EP device 2406 includes an anchor 2418 extending from a proximal to a distal end 2420, at least two oppositely charged electrodes 2422, a central probe 2424 (which may be configured in a same manner as the spiral probe 1702 with open distal end 1708) retractably disposed at the distal end 2420 of the anchor. In some embodiments, the at least two oppositely charged electrodes 2422 are retractably disposed at the distal end 2420 of the anchor 2418 and configured to be positioned surrounding a zone of target cells, e.g. zone 1722 of FIG. 17A. In some embodiments, the measurement device is coupled to the electrodes. The electrodes are adapted to be coupled to a generator, e.g. generator A of FIG. 16, receive at least one electrical waveform from the generator, and supply at least one of an excitation signal and an EP pulse to tissue in the zone. The central probe may have an inner surface defining at least a central lumen and extend from the distal end of the anchor. At least a portion of the central probe 2424 may have a spiral geometry configured to enhance anchoring of the central probe in the tissue and to create a channel for delivery of the therapeutic moieties to the tissue in a similar manner as described with respect to 17A-22C of the present invention. A distal end 2428 of the central probe 2424 may be open to define an opening for delivery of the therapeutic moieties to the tissue and may have a shape configured to pierce the tissue. When the central probe is deployed, the anchor 2418 may be coupled to the proximal end of the central probe 2424.

In some embodiments, each spiral of the central probe 2424 may range from 1 mm diameter to 6 mm in diameter, typically from about 1 mm to 3 mm, more typically from 1.2 mm to 2.3 mm, and in some cases approximately 1.5 mm. In some embodiments, the electrodes may be spaced apart from 2 mm to 10 mm, more typically from 2 mm to 5 mm, and in some cases, approximately 2 mm. In some embodiments, the length of the central probe and length of the electrodes may range from 5 mm to 15 mm, more typically 7 mm to 10 mm, and in some cases approximately 8 mm. Though recited in terms of certain ranges, it will be understood that all ranges from the lowest of the lower limits to the highest of the upper limits are included, including all intermediate ranges or specific measurements, within these full ranges or any specifically recited range.

In some embodiments, the anchor is configured to fit through a 12 ga biopsy needle in order to achieve a 10 cm depth of reach via the biopsy needle. In this way, the EP device may be anchor to soft tumors for an increases dispersion of DNA. The EP device of the present invention provides the advantage that in order to achieve a field strength of 350V/cm, only requires 87V be applied across the 2.5 mm spacing between electrodes. Electric field strengths of this magnitude have been associated with significant enhancement of TM delivery.

In some embodiments, the blade or sharp end 2414 of the obturator 2404 is configured to extend to an outside of the cannula 2402 through the opening at the distal end 2408 of the cannula 2402. The EP device electrodes 2422 may be adapted to extend from proximal to distal ends, tips of the distal ends may have a needle shape configured to pierce the tissue, and the electrodes 2422 may be adapted to be coupled to the generator, receive at least one electrical waveform from the generator, and supply at least one of an excitation signal and an EP pulse to the zone of target cells.

Various embodiments of the present invention are directed to providing a method for delivery of therapeutic moieties to cells in a tissue and EP of the cells using the EP device of the aforementioned embodiments. In some embodiments, the method comprises (i) inserting the central probe to the anchor device, (ii) deploying the electrodes, (iii) partially withdrawing the central probe, and (iv) injecting the therapeutic moieties into the lumen of the central probe for delivery of the therapeutic moieties to the tissue through the distal end thereof. In some embodiments, the method may further include (v) withdrawing the central probe; and (vi) applying electric pulses from the generator 1530 to the electrodes for electroporation; and (vii) removing the device.

(iii) Device for Improved Therapeutic Agent Delivery

Accordingly, the present invention provides apparatuses and methods for the improved delivery of therapeutic moieties to cells in a tissue of a patient. FIGS. 25-33 illustrate EP devices for improved therapeutic agent delivery according to the present invention.

Figure 27:
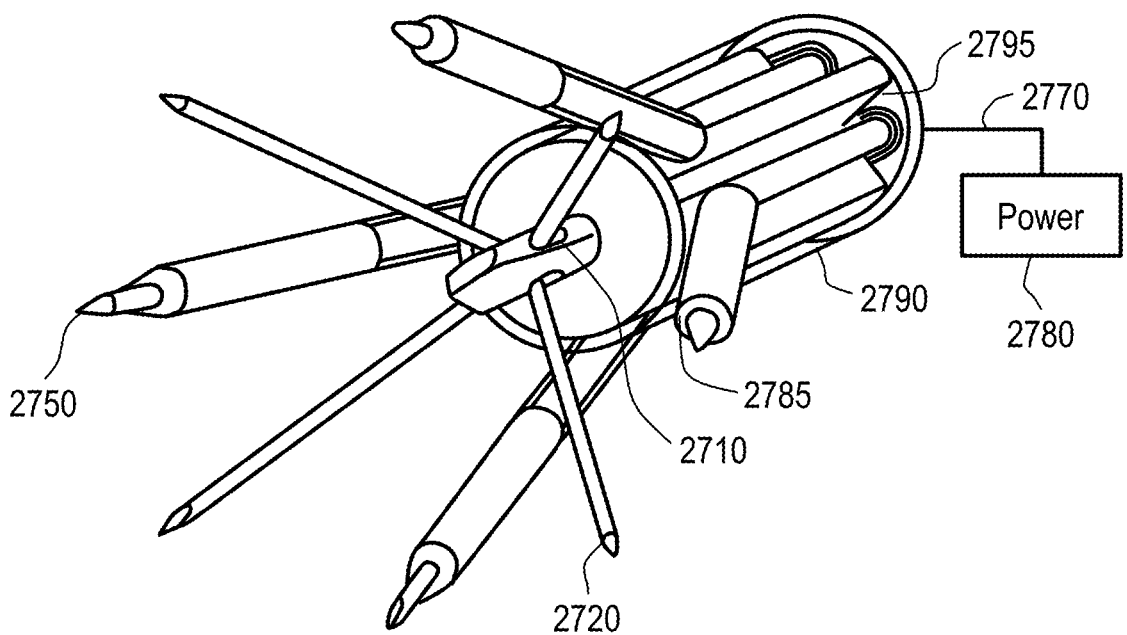
FIG. 27 is a schematic illustration of an EP device for delivery of therapeutic moieties to a zone of target cells of a tissue according to the present invention.
Figure 28:
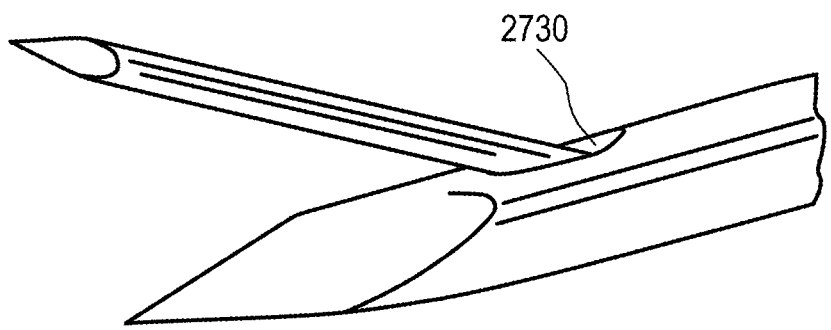
FIG. 28 is a schematic of an exit port and a channeling wire having a blade tip of the EP device of FIG. 27 according to the present invention.

As depicted in FIG. 27, the EP device comprises the central probe 2710 having an inner surface 2712 defining a first central lumen 2715 through which the at least one channeling wire 2720 is extendable to an outside of the central probe 2710 and retractable back into the first central lumen 2715. The central probe 2710 further includes an exit port 2730 which fluidly connects the first central lumen 2715 to the outside of the central probe 2710 and through which injected therapeutic moieties flow from the first central lumen 2715 into the channel in the cell. The EP device also includes a ramp 2760 integrally formed with or coupled to the inner surface of the central probe to guide the channeling wire 2720 outside of the central probe 2710 to reach the diseased tissue or cells.

In some embodiments, the central probe 2710 has a closed distal end and proximal lumen. The distal tip of the probe 2710 is fashioned with any shape that is designed for piercing tissue. Proximal of the distal tip, the exit port 2730 exposes the first central lumen 2715 to the outside of the central probe/needle 2710. The channeling wire 2720, which also has a piercing feature fashioned into the distal tip thereof, is sized such that it is slidable within the first central lumen 2715 and exits through the exit port 2730. The channeling wire 2720 is adapted to be advanced into the tissue of the tumor and create to channel through the tissue which acts as a fluid path for therapeutic moieties that are injected at a later point in the procedure. The channeling wire 2720 is directed outward by the ramp 2760 within the central probe 2710, as illustrated in FIGS. 25-33. The channeling wire 2720 is adapted to be retracted back in the central probe 2710 and the EP device may be rotated to a new orientation. The channeling wire 2720 may be repeatedly advanced into the cells to create additional channels in for therapeutic moiety delivery. The channels created by the channeling wire 2720 enhance the retention of injected therapeutic moieties into the tissue and allows the injection of a greater volume than is possible from a typical needle/syringe of similar size.

In some embodiments, the EP device may further include a handle that automates the extension, retraction, and rotation of the central probe/needle 2710 and channeling wire 2720 to facilitate sufficient depth penetration.

Figure 25:
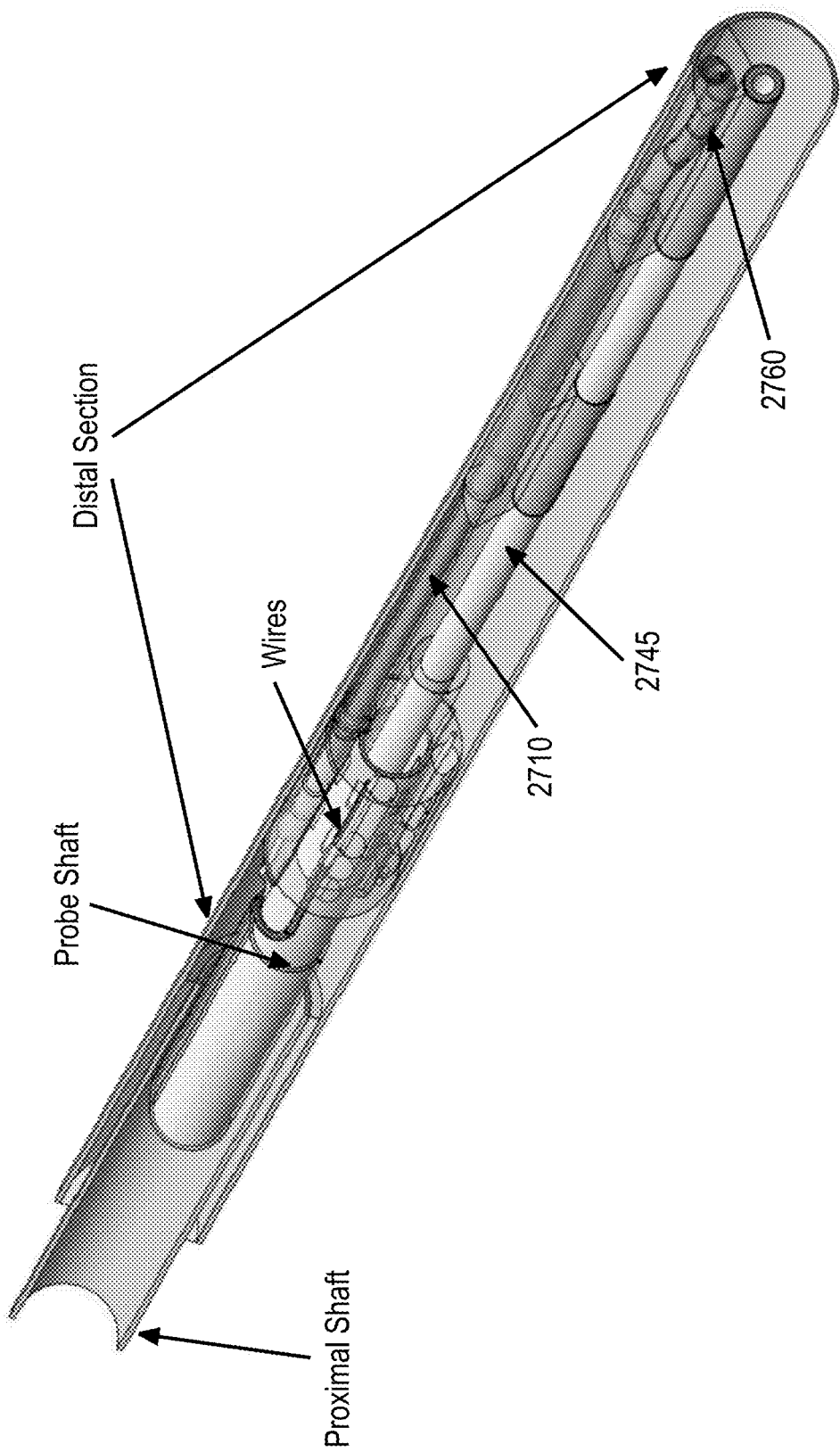
FIG. 25 and FIG. 26 illustrate catheter based/endoscopic EP devices according to the present invention.
Figure 26:
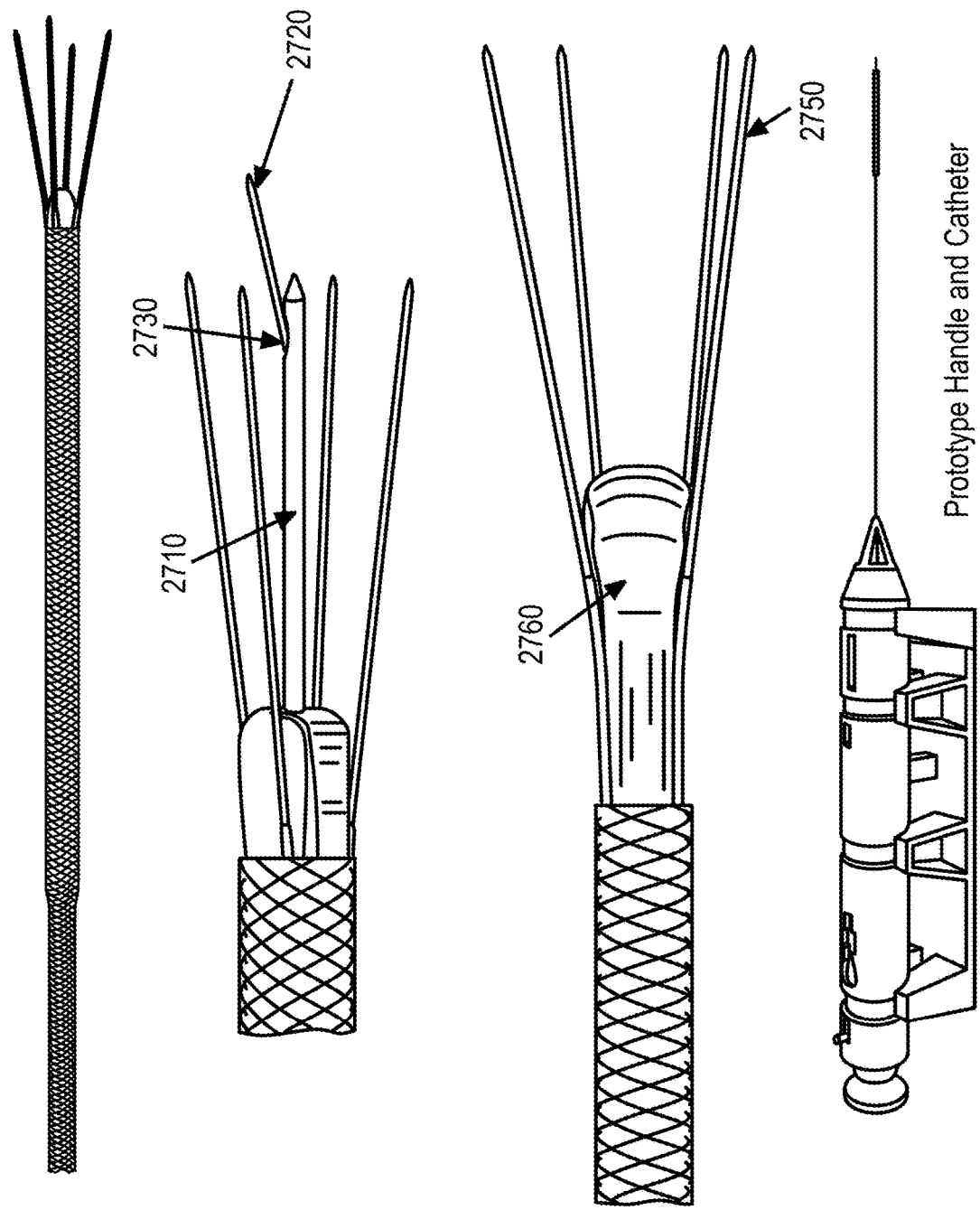

In other embodiments, e.g. the catheter-based or endoscopic EP device of FIGS. 25 and 26, the EP device would include a similar central probe/needle 2710 as described in the primary embodiment.

Figure 30:
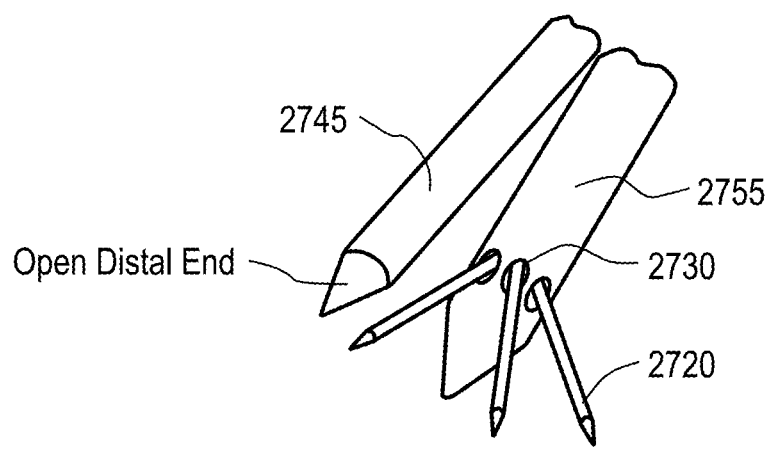
FIG. 30 is a schematic of an injection probe and a central probe coupled to each other according to the present invention.

In other embodiments, e.g. the EP device of FIG. 30, the EP device would include a similar central probe/needle 2710 as described in the primary embodiment. This embodiment would have multiple exit ports 2730 through which multiple channeling wires may exit the device simultaneously.

Figure 29:
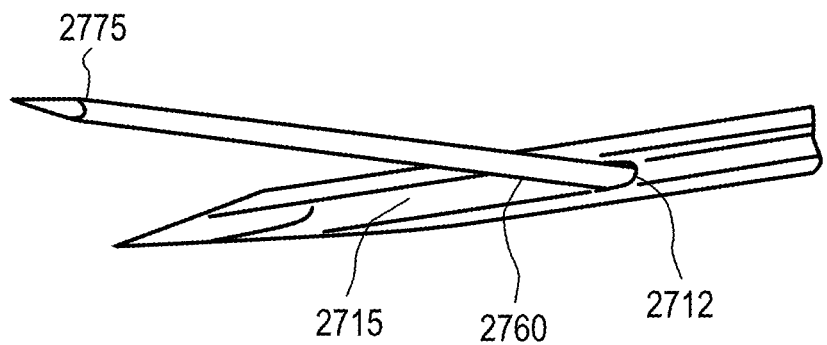
FIG. 29 is a schematic of a ramp and a channeling wire guided by the ramp of the EP device of FIG. 27 according to the present invention.

In some other, as illustrated in FIG. 29 embodiments the channeling wire 2720 comprises a wire that has a cutting blade 2773 fashioned into the distal end. The blade can be extended into the tumor, then the rotated in order to create a disc like cut in the tumor to forms a channel through which the therapeutic moieties are delivered to the cell.

Figure 31:
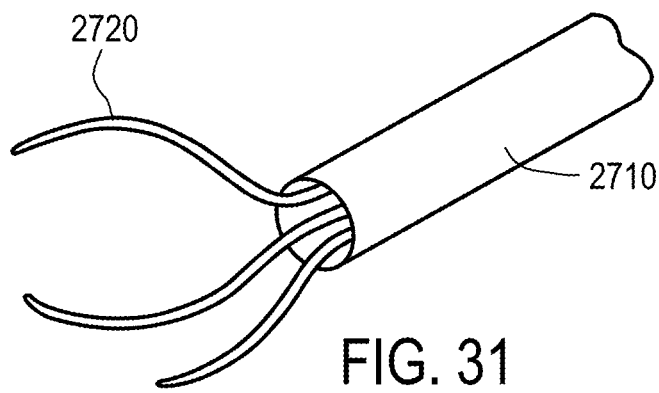
FIG. 31 is an illustration of a curved channeling wire of the EP device of FIG. 27 according to the present invention.
Figure 32:
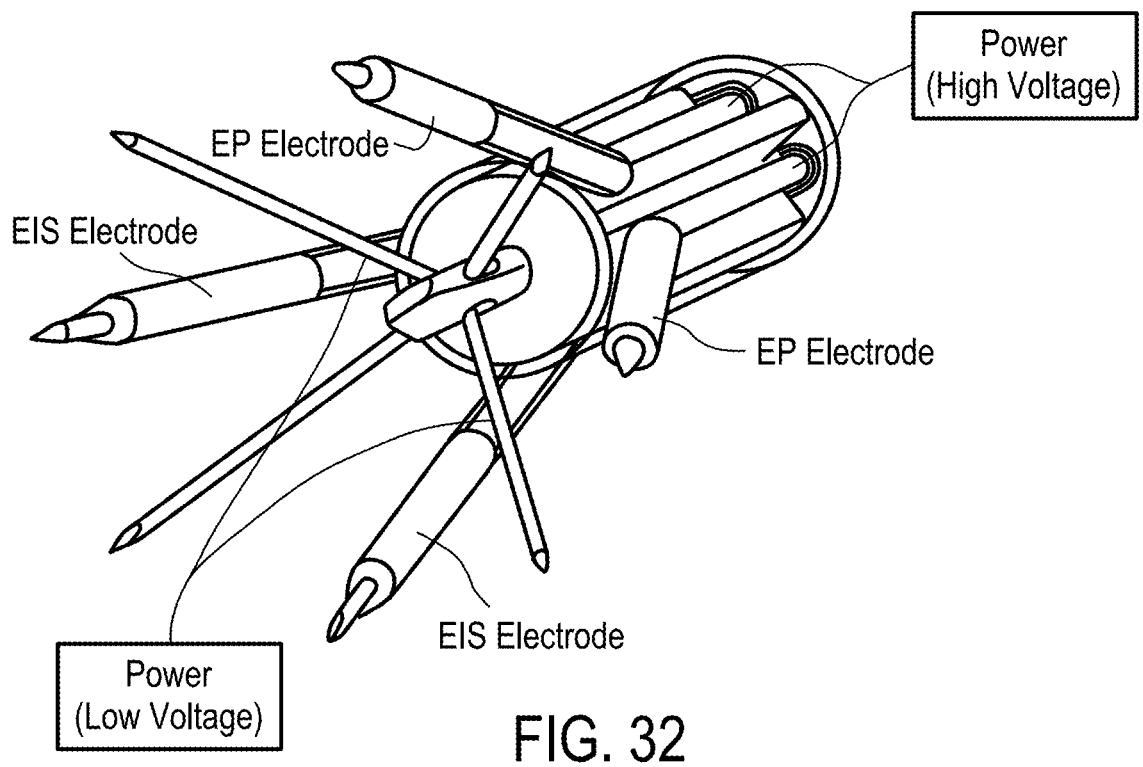
FIG. 32 is a schematic illustration of a capacitance sensing (CS)/EIS sensing system according to the present invention.

In yet another embodiment, as illustrated in FIG. 31, the central probe has an open distal end similar to a typical syringe/needle. The channeling wire 2720 may be formed of a shape memory alloy, such as a super-elastic material (e.g., nitinol) such that a curve is heat set into the wire (sometimes referred to as "shape memory"). When the channeling wire is in the central probe 2710, the wire is elastically straightened. Upon exit from the central probe/needle, the channeling wire 2720 is allowed to return to its curved shape, as illustrated in FIG. 31, thus creating a channel that extends outward from the device.

In yet another embodiment, as illustrated in FIG. 30, the EP device comprises an injection probe 2745 having an injection needle at a distal end thereof for injecting the therapeutic agent and a central probe 2755 having a separate lumen for guiding the channeling wire 2720. An inner surface 2712 of the central probe 2755 may contain a ramp 2760, e.g. as illustrated in FIGS. 25, 29 and 30, for guiding the channeling wire 2720 outward from the central probe 2755 to inside the tumor. The two members that create the two lumens are bonded side by side by a method that is appropriate for the material of their construction. For example, if the two lumens are made of a metal, they may be spot welded together, and if the two lumens are made of a material such as a hard plastic, the two lumens may be ultrasonically welded together. Alternately, a single member of integrally formed multi-lumens could be utilized to achieve the same thing. This configuration yields an advantage in treatments where the therapeutic moieties require a larger injection lumen for delivery.

Referring to FIG. 27, an apparatus for the improved delivery of therapeutic moieties to cells in a tissue according to some embodiments of the present invention further includes an electrical connector 2770 electrically connecting the central probe 2710 and the channeling wire 2720 to a power source 2780, a small bore connector, 2795 configured to connect the central probe 2710 to a syringe for delivery of the therapeutic moieties, and a handle 2790 housing the electrical connector 2770 and coupled to proximal ends of the central probe 2710 and the channeling wire 2720 to facilitate a depth of penetration of the distal ends of the central probe the said channeling wire 2710.

As illustrated in FIG. 26, FIG. 27, FIG. 28 and FIG. 29, the central probe 2710 extends outwards in a vertical direction from a proximal end to a closed distal end thereof and is configured with a needle shape at the distal end to provide the initial penetration into the tumor/tissue. The inner surface 2712 of the central probe 2710 defines the first central lumen 2715 and is configured with the ramp 2760 that guides the channeling wire 2720 outward from the EP device. The first central lumen 2715 provides the path for the injected therapeutic moieties to flow along before being delivered to the diseased cells or tissue.

In some embodiments, the exit port 2730 is positioned on a side surface of the central probe 2710 at a predetermined distance from the distal end thereof, through which the therapeutic moieties are delivered to the diseased cells or tissue. The exit port 2730 fluidly connects the central lumen to an outside of said central probe. The central probe 2710 may be formed of a low conductive material coated with an insulating (non-conductive) material at the distal end so as to avoid interference with electrical fields that may be optionally applied using EPEs in order to facilitate uptake of the therapeutic moieties by the cells. The central probe 2710 may measure from about 1 mm to about 10 mm, depending on the geometry and physiology of the tissue to be treated and how deep the channeling wire 2720 and EPEs 2750 need to be inserted into the tissue.

In some embodiments, the channeling wire is positioned in the central lumen and slidable within the central probe. The channeling wire may have a proximal end positioned in the central probe and a distal end having a needle-shaped piercing configured to extend to an outside of the central probe through the exit port 2730 to reach and penetrate the diseased cells and create a fluid channel through which the therapeutic moieties may be delivered to the tissue. The channeling wire may be formed of a low conductive material coated with a conductive material, or an insulating (non-conductive) material at the distal end so as to avoid interference with electrical fields that may be optionally applied using EPEs. The channeling wire 2720 may measure from about 1 mm to about 20 mm, depending on the geometry and physiology of the tissue to be treated and how deep the channeling wire 2720 and EPEs 2750 need to be inserted into the tissue.

As illustrated in FIG. 29, the ramp may be integrally formed with or coupled to the inner surface 2712 of the central probe, and may be adapted to contact and guide the channeling wire to exit the central probe to the outside of the central probe. The ramp 2760 may be formed or coupled to the inner surface of the central probe at a predetermined angle which may or may not be adjustable based on an angle of extension necessary for the channeling wire 2720 to reach the diseased cells.

Referring to FIG. 27, in order to supply power to the EP delivery device, the electrical connector 2770 electrically connects the central probe 2710 and channeling wire 2720 to the power source 2780. In some embodiments, the power source may be a generator such as the generator illustrated in FIG. 16 of the present invention. The power source may be a high voltage power source so as to facilitate the application of high voltage electric pulses to optional EPEs for creation of electric fields to open pores of the diseased cells.

The handle 2790 houses the electrical connector 2770 at least in part and is coupled to proximal ends of the central probe and the channeling wire to facilitate a depth of penetration of the distal ends of the central probe and the channeling wire. The handle 190 may provide the proximal termination point of the various components (e.g. the channeling wire, the first central lumen), the connection point of the central probe 2710 and the small bore connector fitting 2795. The handle also serves as the main user interface to the device and may include one or more user-input buttons electrically connected to the channeling wire and/or optional electrodes for actuation or deployment of the channeling wire and/or optional electrodes. The handle also houses the electrical connector 2770 that is connected to the power source 2780. The handle allows control over the orientation and direction of the device, deploys and retracts the channeling wire, deploys and retracts the central probe/needle, deploys and retracts the optional electrodes, remotely triggers the delivery of electroporation pulses (optional). Additionally, as described above, the handle is configured to facilitate the depth of penetration of the needle, channeling wire, and electrodes.

In some embodiments, the handle 2790 is formed for ease of physician use, for example having molded handle parts or grips, optional lighting elements at the distal end, cameras for observing and documenting treatment sites, biopsy forceps, tissue scissors, ligation devices, suturing systems, etc.

In addition, the electrodes 2750 and the handle 2790 are preferably made of materials that can be sterilized and configurations that similarly minimize microorganism trapping if the electrode array and wand housing is to be reused. In some embodiments, at least the electrode arrays are disposable, and in some embodiments the entire handle is also.

In some embodiments, as illustrated in FIGS. 25 and 26, the EP delivery device may further include a catheter shaft surrounding an outer surface of the central probe to support and protect the central probe during insertion into a body having the tissue, as illustrated in FIG. 8.

a. Electroporation Electrodes

As described above, the EPEs 2750 are electrically connected an EP power supply 2780. The electrical connector 2770 may include four or more conducting wires (depending on the number of EPEs) for transmitting electrical signals from the power supply to the each of the EPEs. These signals may include needle voltage setpoint, pulse width, pulse shape, the number of pulses, and switching sequence. As will be appreciated by those in the art and more fully described below, the EP electrodes may also serve as capacitance sensing (CS) or impedance sensing (EIS) electrodes, in which case a second low voltage power supply is used with appropriate switching mechanisms to allow the delivery of higher voltage EP signals and then lower voltage CS or EIS signals as illustrated in FIG. 1.

The EPE electrodes 2750 are formed of material which is conductive, although optional insulative coatings may be used as discussed herein. The electrodes may be made of any conductive material able to pass the large instantaneous current densities associated with high-voltage pulses applied, including, but not limited to certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include AgCl, cobalt-chromium, titanium, stainless steel, platinum, gold, or metal of high electrical conductivity which is plated in gold or platinum.

In addition, the electrodes, TM delivery device and wand housing are preferably made of materials that can be sterilized and configurations that similarly minimize microorganism trapping if the electrode array and wand housing is to be reused. In some embodiments, at least the and/or TM delivery and electrode arrays are disposable, and in some embodiments the entire wand housing is also.

In some embodiments, for example when distal ends of the EPEs are exposed for generation of the electric fields, but proximal ends thereof may be coated with a non-conductive substance so as to limit application of the electric field to only the distal ends of the EPEs adjacent to the tissue and not along the length of the electrodes, for example to allow EP "deeper" in the tissue but not at "shallow" regions. In some embodiments, the EPEs can have areas of alternating insulative material and bare electrodes, as generally depicted in FIGS. 4A and 4B. In this embodiment, the electrodes can be coated in the same pattern, resulting in more uniform electric fields, or different patterns, resulting in asymmetrical electric fields. Similarly, for all the electrode configurations herein, the electrodes can have the same lengths or different lengths.

The pulsed electric fields generated by such partially insulated EPEs are primarily concentrated in regions between and near exposed tip portions at the distal ends of the electrodes during a treatment, and are small in regions between and near the insulated portions.

In some embodiments, the EPEs are generally of a length so as to fully surround the tissue to be treated. In preferred embodiments, all the sets of electrodes (the "array" of electrodes) are the same length within the array, although in some instances, the use of different lengths of electrodes can result in altered and asymmetrical electric fields.

In many embodiments, the electrodes range from 1 mm to 20 mm in length. It should be noted that this measurement is the depth of insertion and not the total length of the electrodes 2750; in general there will be a portion of the electrode that extends up from the point of contact with the tissue and extends into the handle 2790 for attachment to the appropriate circuitry, to hold the electrodes in the correct spatial configuration, etc.

In many embodiments, the width and cross sectional shaping of the electrodes for insertion are configured to minimize pain. Accordingly, the width of the electrodes may be from about 0.5 mm to 1 mm to 20 mm, with from 1 mm to 15 mm being preferred.

b. Therapeutic Moiety Delivery Methods

Various embodiments of the present invention are directed to a method for delivering therapeutic moieties to cells in a zone of target cells in a tissue using the delivery device 100 of the present invention.

Figure 33:
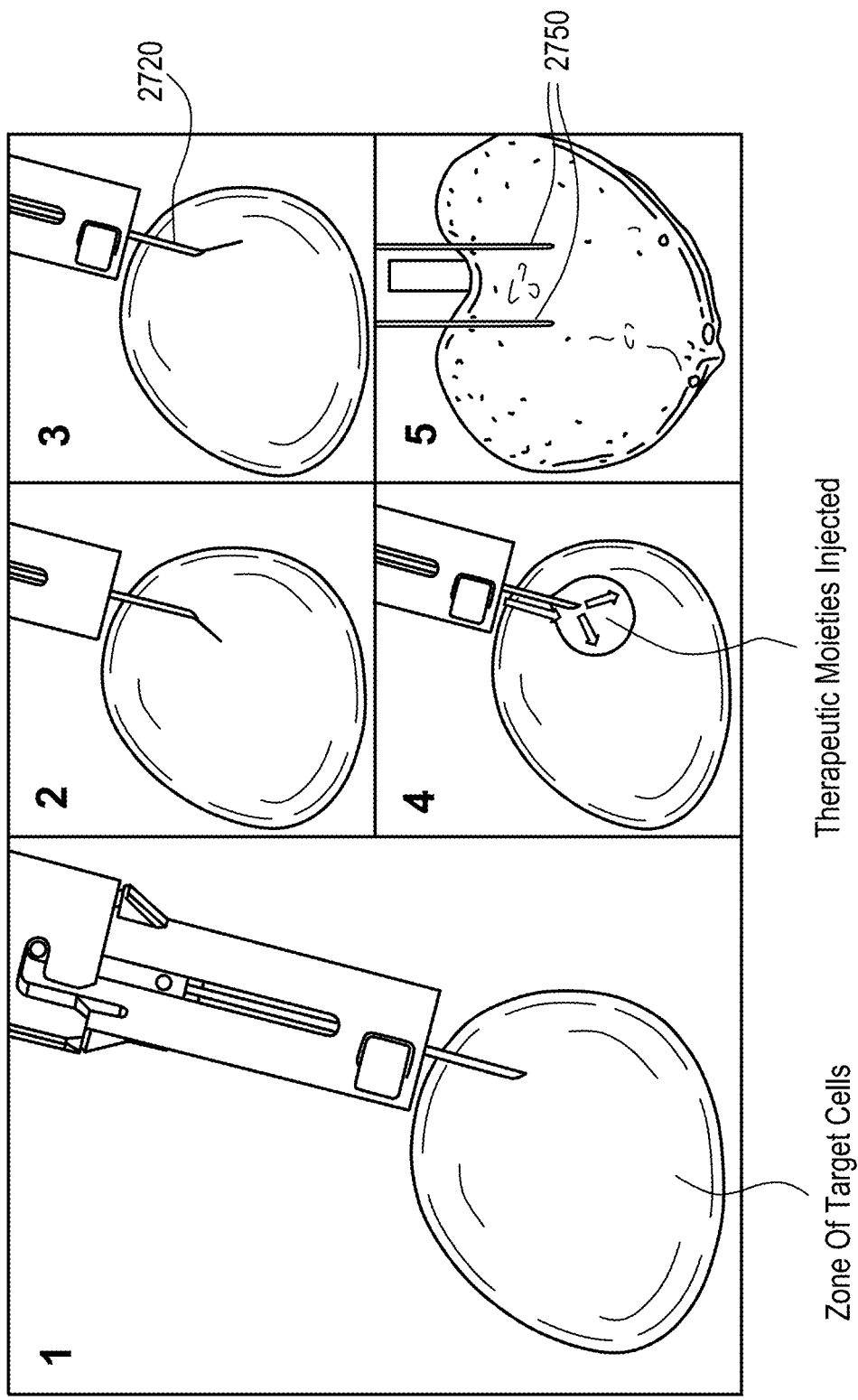
FIG. 33 is an illustration of a method for delivery of therapeutic moieties to a zone of target cells of a tissue using an EP device according to the present invention.
Figures 34A, 34B, 34C:
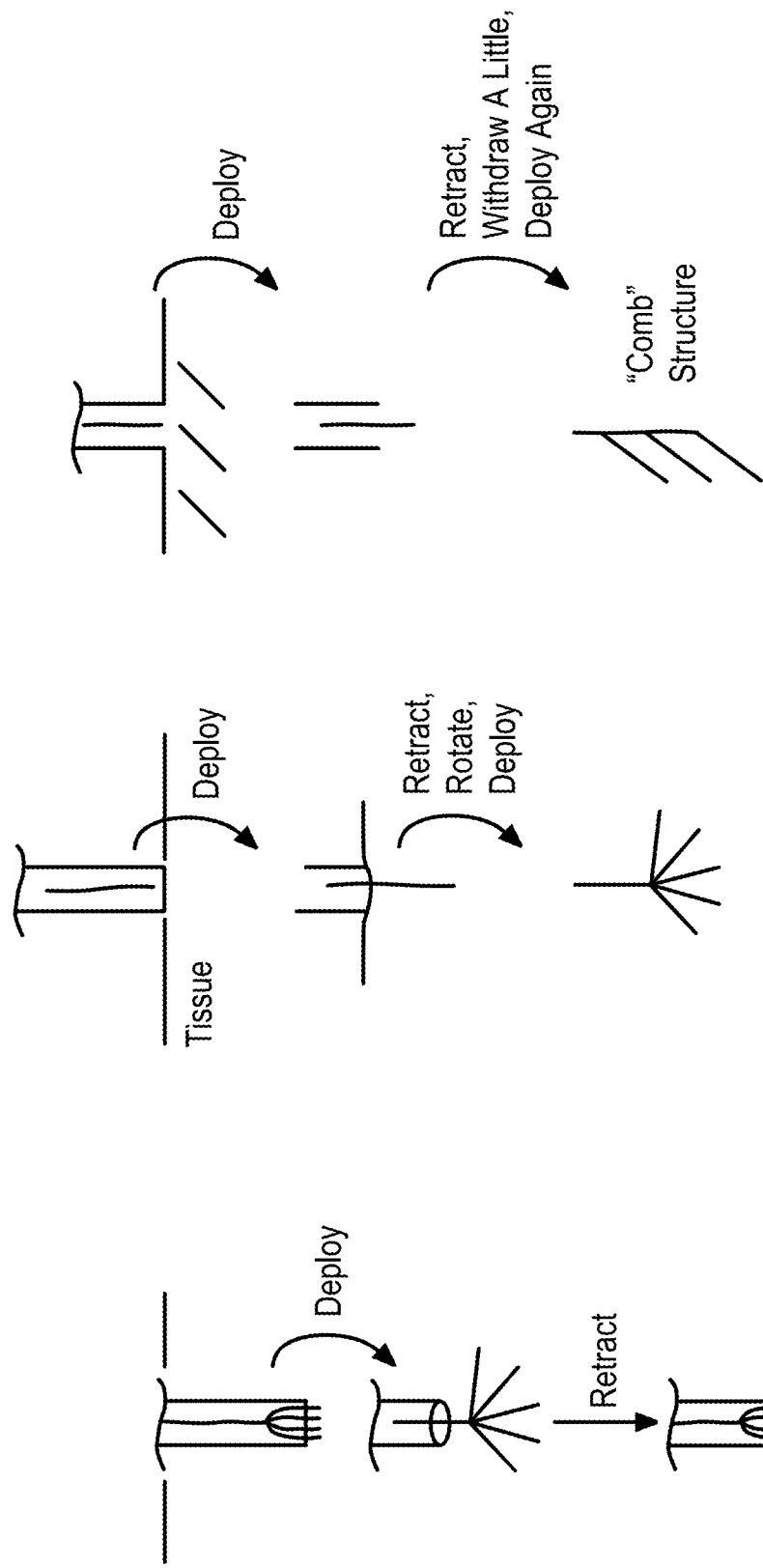
FIGS. 34A, 34B and 34C illustrate a variety of configurations of an EP device (of FIG. 27) according to the present invention.
Figure 35:
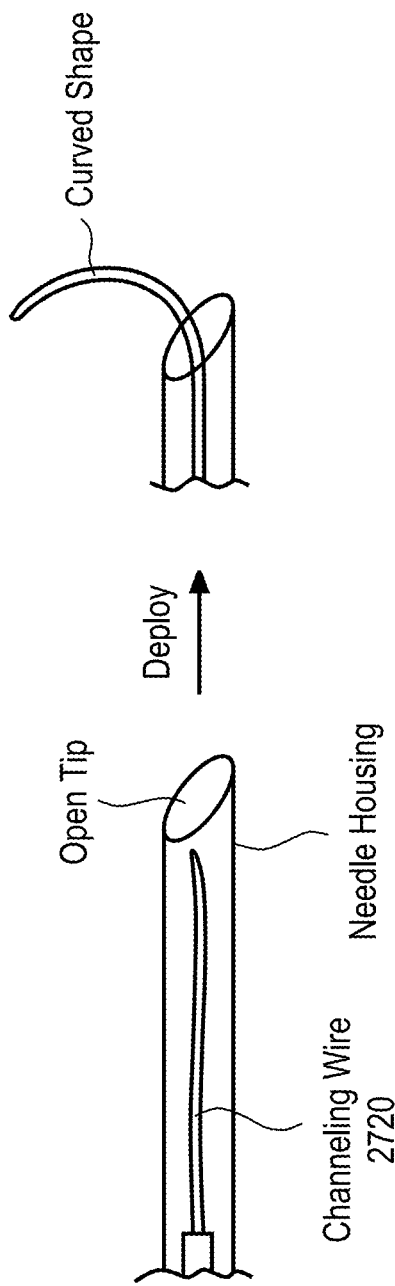
FIG. 35 shows a housing containing a curved channel wire, held rigid when in place, but upon deploying the wire, it returns to its curved shape and forms a curved channel of a fluid reservoir.

In some embodiments, the method for delivering therapeutic moieties to the zone of target cells comprises providing the device for delivery of therapeutic moieties of any of the embodiments of the present invention described herein, to a zone of target cells of a tissue. FIG. 33 is an illustration of a method for delivery of therapeutic moieties to a zone of target cells of a tissue using an EP device according to the present invention.

In some embodiments, the method for delivery of therapeutic moieties to a cell may include inserting a central probe/needle, e.g. 2710 into the cell. In some embodiments, e.g. as illustrated in FIGS. 25 and 25, the EP device may be for endoscopic use to reach cavities of a body which are not easily accessible. The channeling wire 2720 is deployed from inside the central probe 2710 to outside the central probe 2710 via the exit port 2730 on a sidewall of the central probe 2710, thereby creating a fluid channel in the cells or tissue. The channeling wire 120 is then withdrawn, the central probe 2710 rotated and the channeling wire once again extended. Multiple probe deployments create fluid channels within the tumor. With the channeling wire withdrawn, the therapeutic agent is injected, flowing into the fluid channels.

The method for delivering therapeutic moieties to the zone of target cells according to the present embodiment further comprises inserting the central probe 2710 into a diseased cell in the zone of target cells, actuating and extending the channeling wire 2720 from the central lumen in an axial direction of the central probe 2710 and piercing the cells or tissue with the distal end of the channeling wire having the needle shape. The method may further include, as a result of the piercing, making an opening through which at least a portion of the channeling wire 2720 enters the tissue and creating a fluid channel through which the therapeutic moieties are delivered. The method may further include actuating the ramp 2760 which is integrally formed with or coupled to the inner surface of the central probe 2710 and contacting the channeling wire with the ramp so as to guide a trajectory of the channeling wire through the exit port towards the distal end of the central probe 2710. Upon exiting the central probe, the channeling wire 2710 is extended to piercing the tissue and create an opening through which at least a portion of the channeling wire enters the tissue to create a fluid channel for delivery of the therapeutic moieties to the tissue. The channeling wire may be retracted back into the central lumen and the therapeutic moieties are then injected into the central probe through a syringe. Once injected into the central probe, the therapeutic moieties travel out though the exit port and into the channels in the cells created by insertion of the channeling wire.

In other embodiments, the channeling wire may have a blade shape and the method of creating the channels may further include rotating the channeling wire while in the cell to create a hollow cylindrical channel with a larger area for receiving larger quantities of therapeutic moieties.

VI. Adaptive Control Methods of the Invention

Figure 36:
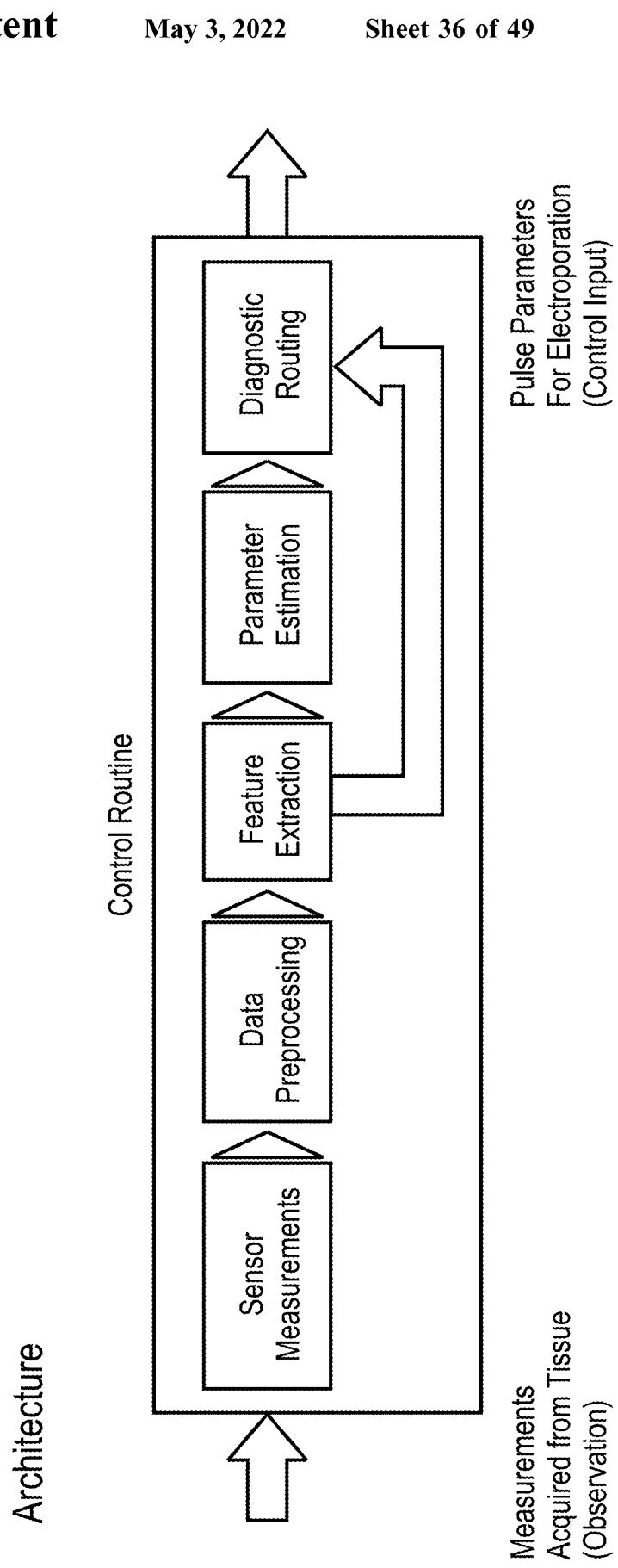
FIG. 36 is a flowchart illustrating a control routine for an adaptive control method for controlling EP pulse parameters during using an EP system according to the present invention.
Figure 37:
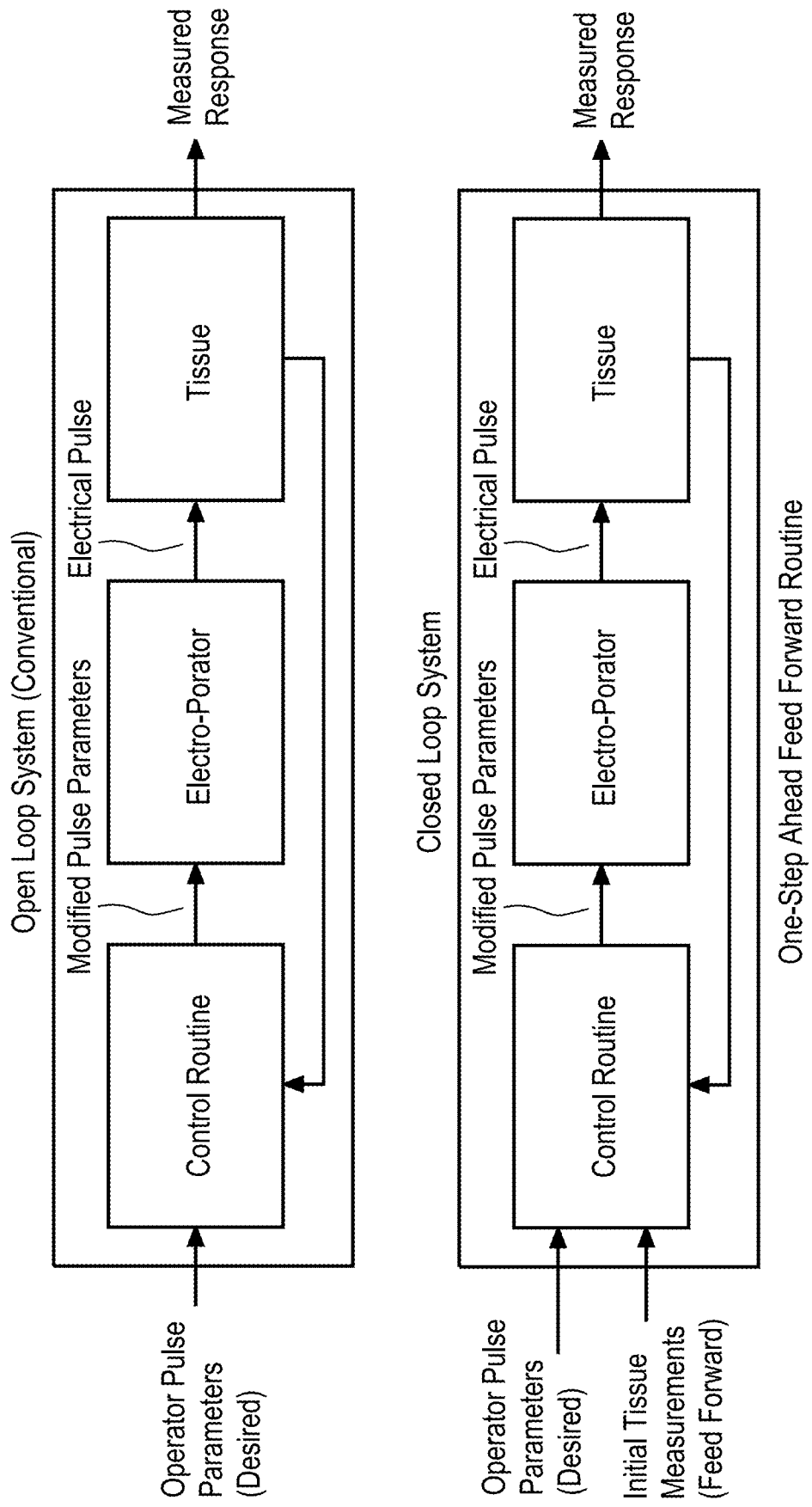
FIG. 37 is a flowchart illustrating a one-step ahead feedforward control routine for optimizing EP pulse parameters employing the control routine of FIG. 36 according to the present invention.

Various embodiments of the present invention are directed to an adaptive control method for controlling EP pulse parameters during EP of cells in a tissue, using an EP device. FIG. 36 is a flowchart illustrating a control routine for an adaptive control method for controlling EP pulse parameters during using an EP system according to the present invention, and FIG. 37 is a flowchart illustrating a one-step ahead feedforward control routine for optimizing EP pulse parameters employing the control routine of FIG. 36 according to the present invention. In some embodiments, the adaptive control method may be implemented using any of the EP devices described herein. The method of the present invention is however, not limited to such, but may also be practiced on any of the EP systems and devices/applicators and any methods such as those outlined in U.S. Provisional Patent Application Nos. 62/214,807, 62/214,872, 62/141,142, 62/141,182, 62/141,256, and 62/141,164, all of which are expressly incorporated by reference in their entirety, specifically including the Figures, Legends and descriptions of the Figures and components therein.

The devices, systems and methods of the present invention will improve the process of EP-based gene therapy. Current EP systems apply an open-loop control system using static parameters that rely on a priori knowledge determined by preclinical studies in homogeneous syngeneic tumor models. However, preliminary data has shown that even in homogeneous tumors, the time required to apply an electrostatic field across a cell membrane follows a log-normal distribution. Applying static parameters to different tumors, even in a homogenous model, results in a wide range of applied electrostatic fields across cell membranes and leads to treatment variability. One potential remedy is to define static parameters that apply sufficiently long EP pulses that encompass 95% of known membrane charging times. However, due to variance in the charging times, the average tumor would be over treated by a factor of 4, increasing the likelihood of adverse effects such as necrosis and apoptosis. The present invention provides a solution to the aforementioned problem by implementing a closed-loop control system using tissue-sensing based feedback control to optimize the EP process with tumor-specific measurements acquired before and between each EP pulse. In some embodiments, tissue sensing will be used to measure the membrane charge time for a specific tumor to tailor each EP pulse for optimal treatment. Constraint boundaries are imposed on the EP pulse parameters to ensure feedback convergence. The necessary conditions required to implement a closed-loop control system for enhancing EP are (1) the ability to exert an electrical force on a tissue to drive it towards a desired state and (2) the ability to measure the state of the tissue. This can be achieved by measuring bioelectrical changes as a result of applied electrical excitation signals.

The feedback adaptive control method of the present invention employs a closed-loop feedback control mechanism to regulate EP by monitoring the physiological properties of tumors before and between EP pulses. Physiological properties will be determined by fitting EIS tissue data to equivalent circuit models, described herein, in real-time with a non-linear least-squares curve fitting routine. Fitting data to tissue models allows the integrity of cell membranes, represented by CPEs, to be quantified for the tissue being treated. The duration of EP pulses is modulated based on CPE model fit parameters, allowing EP to be stopped when a relative change in CPE parameters reaches a level associated with therapeutically beneficial pDNA expression. The control devices, systems and methods of the present invention will allow a user to inject a therapeutic molecule, characterize the baseline state of the tissue, deliver optimized EP pulses for that tissue, and stop pulsing when a relative drop in membrane integrity is achieved. This removes any ambiguity associated with EP, and ensures successful delivery of immunotherapeutic genes regardless of variations in tumor properties. Thus, EIS represents a significant advancement in the hardware currently used for clinical intratumoral immunotherapy.

Various aspects of the present invention address the need to advance the practice of EP by implementing the dynamic feedback control system, as described above. In vivo EP for gene therapy has been used clinically in vaccination and oncology indications for many different tissue types and tumor As described above, EIS is a low power technique capable of real-time monitoring of tissues. This technique is performed by applying a series of low voltage excitation signals across a pair of electrodes and measuring a response current over a range of frequencies. The magnitude and phase of each applied excitation is then computed and fit to an equivalent circuit model of the tissue. A common equivalent circuit used for tissue is illustrated above. In this model, resistive elements ($R_I$ and $R_E$) are due to the intracellular and extracellular matrix, respectively, and lipid structures are represented by the constant phase element ($CPE_M$). $CPE_M$ is a function that represents the charge or capacitance of the lipid bilayers (denoted by $Q_M$) and a scalar ranging from 0 to 1 representing the non-ideal nature of the capacitor (denoted by $\alpha$). The time-constant for charging the lipid bilayer, computed as $\tau = (R_I Q_m)^{1/\alpha}$, can be used to identify the optimal EP pulse durations before each treatment.

Figure 38:
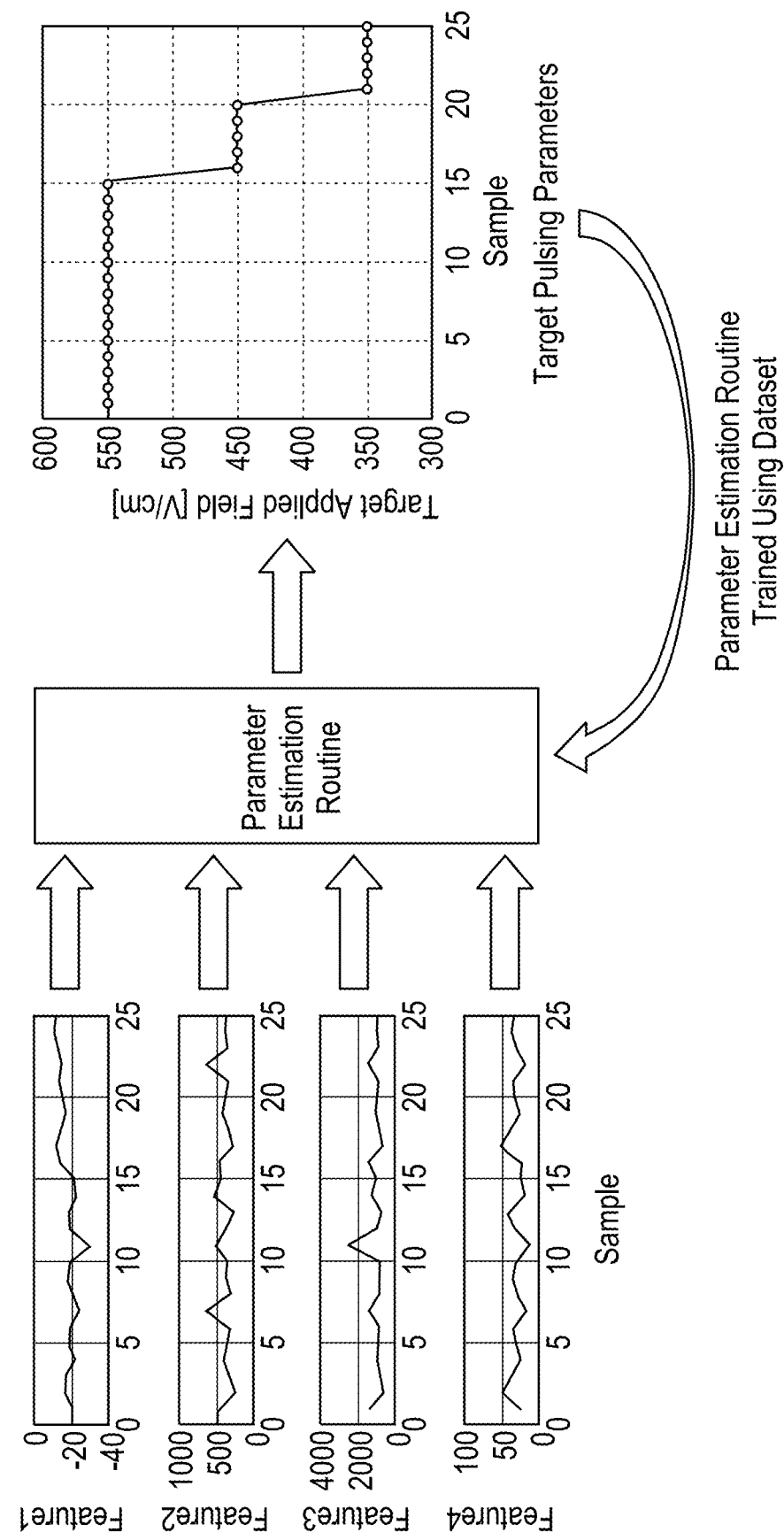
FIG. 38 is an illustration of an initial training stage for a model used to estimate pulsing parameters according to the present invention.
Figure 39:
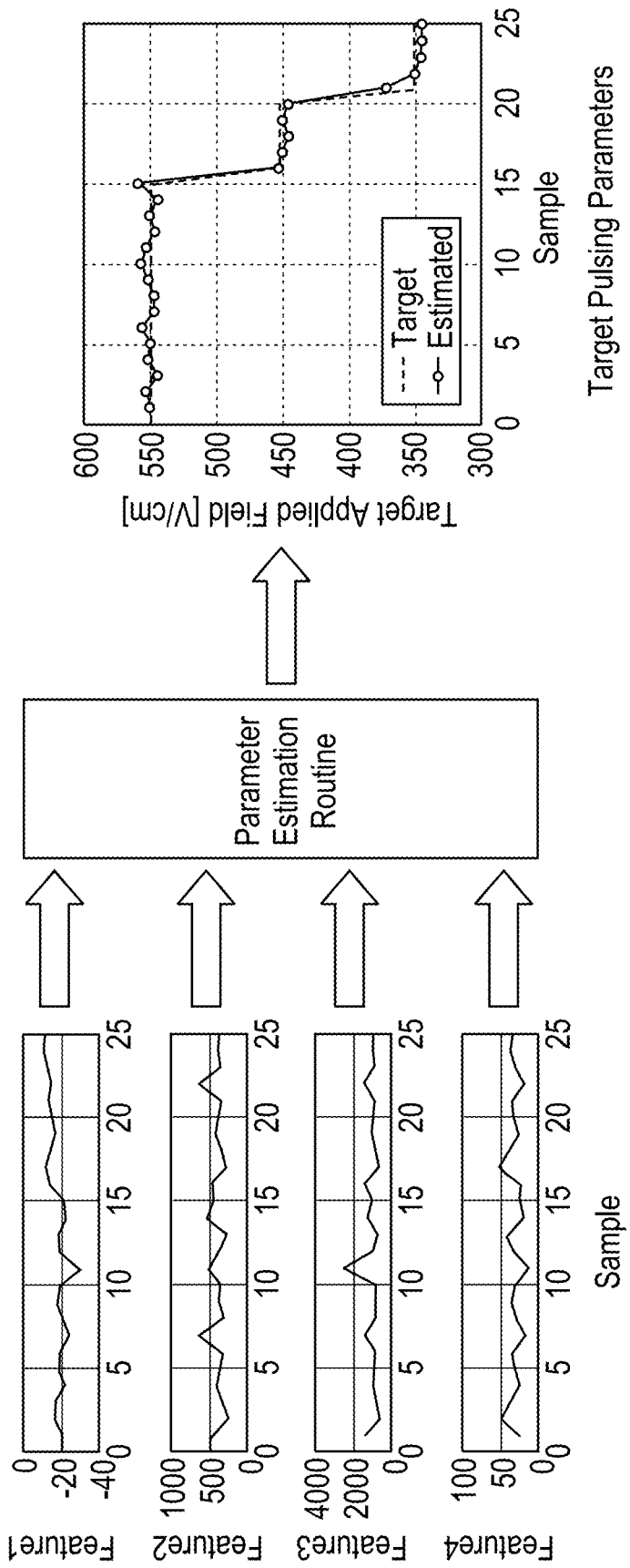
FIG. 39 is an illustration of the trained model used to estimate first pulsing parameters (initialize) according to the present invention.

In some embodiments, the adaptive control method for controlling EP pulse parameters during electroporation (EP) comprises providing any one of the EP systems described herein. Various embodiments of the EP systems and devices of the present invention utilize the same electrodes to perform low power EIS measurements and to high power EP pulses. The aforementioned configuration is ideal, as this reduces the number of required electrodes and directly measures tissue responses. The adaptive control method further comprises initializing EP pulse parameters for performing EP in the tissue and the initialized EP pulse parameters are based at least in part on at least one trained model as illustrated in FIG. 38. FIG. 38 is an illustration of the initial training stage for a model used to estimate pulsing parameters according to the present invention. As described previously, the model may be a physics-based model, empirical model, or data-driven model. In some embodiments, the trained model is trained using empirical data observed during initial operation of an EP device using fixed EP pulse parameters. The models may be trained using supervised learning routines using machine learning methods. In some embodiments, the particular implementation used for the model prediction stage may be a decision support tree which generates a logical rule-set for parameter estimation and diagnostics according to the adaptive control method of the present invention.

In some embodiments, the present invention is directed to a "one-step feedforward control". By "one step ahead feedforward control" it is meant that before a first EP pulse is applied, the parameter estimation routine initializes the initial control parameters for the first pulse based on the model trained in the initial training phase using the empirical data from previously conducted experiments. These previously conducted experiments may be based for example on tissue samples with tumors having similar characteristics to those of the current tissue to be subjected to the control method of the present invention. The initialization may be an initial training phase which is conducted offline. Parameter estimation routines (to be described more fully below) are first created during an initial model training phase, using, for example, empirical data collected from a number of experiments/trials. This may be done offline by operating the system without any feed-forward or feedback control (fixed pulse parameters). The empirical data may include a variety of fixed pulse settings, resulting features and corresponding biological outcomes resulting from these experiments/trials. Based on the previously trained models and measured features, derived from tissue sensing measurements in the initial training phase and from a tissue or tumor type identified in a diagnostic phase, the controller uses the parameter estimation routine to select optimal parameters/conditions for the first EP pulse. These first pulse parameters are thus "fed forward" to be applied as the first pulse for the control routine as opposed to the conventional EP systems and methods in which parameters/conditions of the first pulse are based on fixed conditions. In this sense, the methods of the present invention utilize feedforward control to provide optimal EP parameters based on a sensed tissue type, in conjunction with feedback control to sense cell conditions, e.g., degree of permeabilization and adjust the pulse parameters accordingly.

Figure 41A:
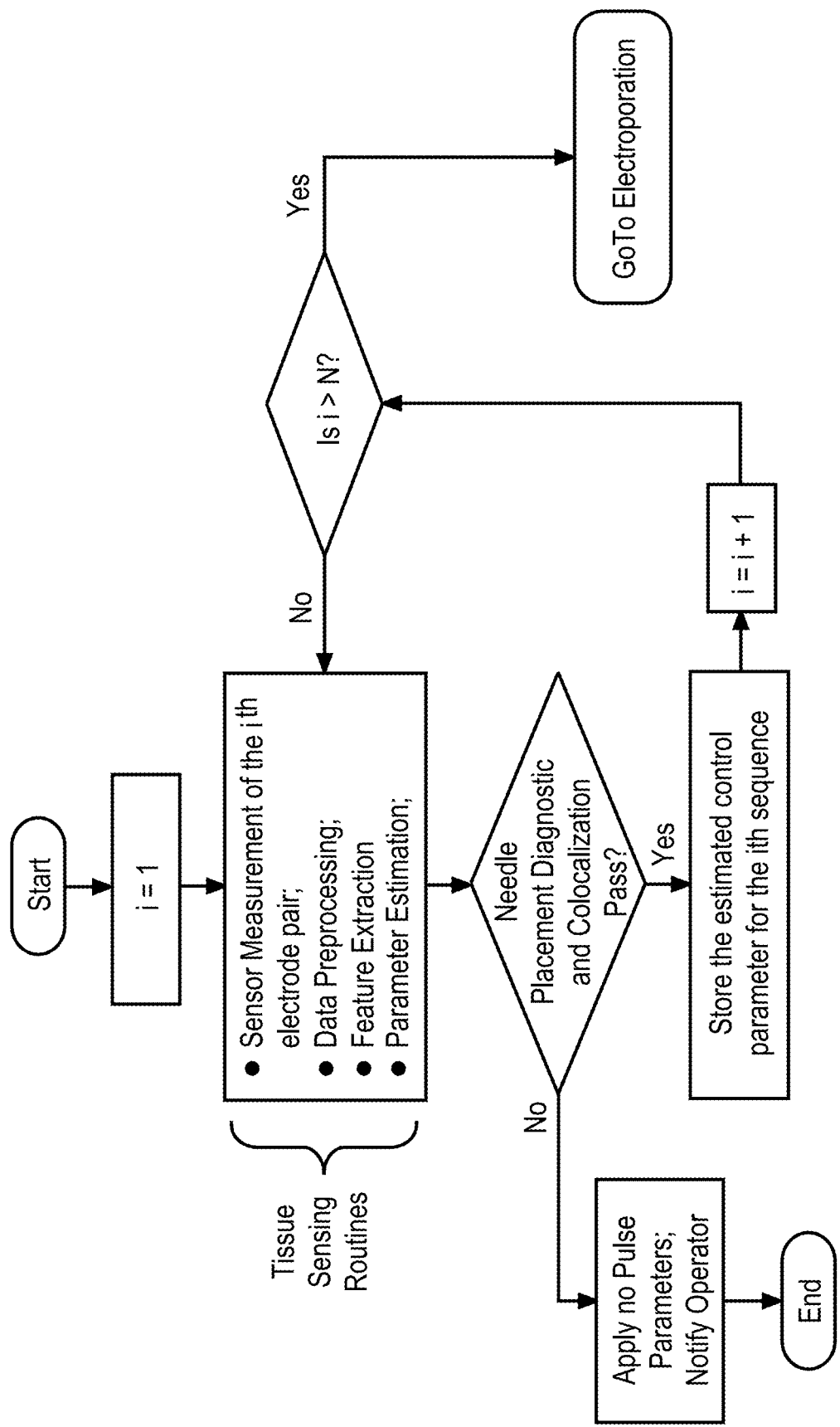
FIG. 41A and FIG. 41B are a flow-chart illustrating the method for adaptive control of EP pulse parameters according to the present invention.
Figure 41B:
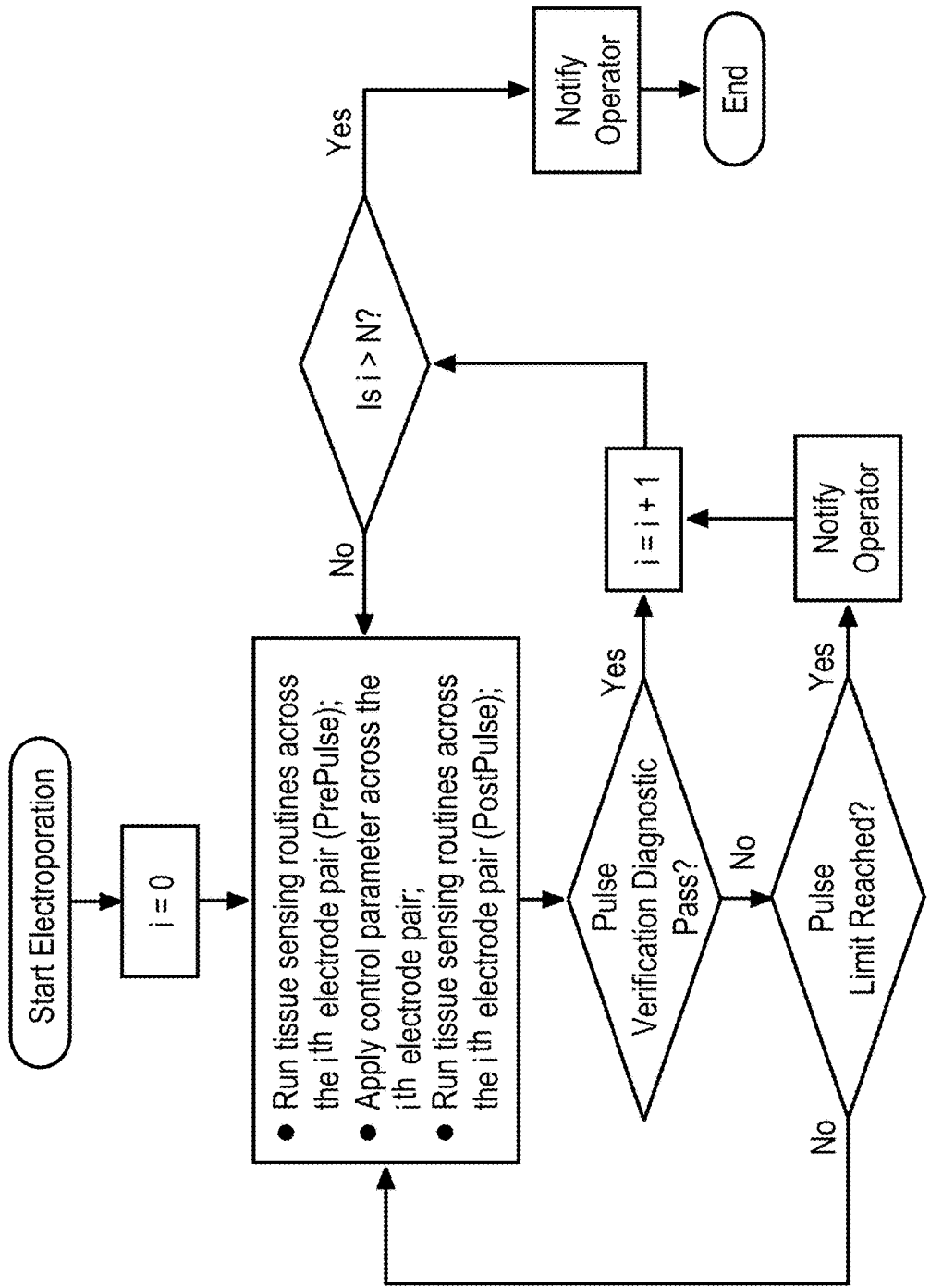

FIG. 41A and FIG. 41B are a flow-chart illustrating the method for adaptive control of EP pulse parameters according to the present invention. As illustrated in FIG. 41A, the adaptive control method further comprises applying voltage and current excitation signals from the signal generator 1530 to the cells using the $i^{th}$ electrode pair of the EP device 1540, and measuring the voltage and the current across the cells and tissues corresponding to the applied excitation signals to obtain dielectric and conductive properties of cells and tissues, including but not limited to capacitance, resistance and impedance. Here, the i=1 for measurements taken across a first set of electrodes. In some embodiments, the current and voltage measurements may be made by a voltage sensor and a current sensor, for example, as illustrated in the measurement device 1510 of control system of FIG. 15. The current and voltage sensors (which may be integrated into the electrodes of the EP device or contained separately elsewhere in the control system of the present invention) act as transducers which sense current and voltage across the cell membranes and detect any changes in quantities and provide an output signal to the controller 1505, for the controller to carry out a function corresponding to the signals received from the sensors, i.e., predict the first pulse parameters. The excitation voltage signal is applied initially, and then between each set of EP pulses, e.g., between first and second EP pulses, and measured across the tissue. This signal may be a band-limited signal. The corresponding current signal is measured. This sensor data is time-correlated and saved internally for use during data pre-processing as described below.

The adaptive control method further comprises obtaining the sensor data from the measurement device 1510, corresponding to results of the measured cells or tissue properties and processing the data into diagnostics and updated control parameters. In these embodiments, the pre-processing module 1550 of the controller 1505, pre-processes the data to separate desirable data from undesirable data. In some embodiments, the voltage and current sensors 1510 transmit a signal to the controller 1505 of the voltage and current measurements, and the controller derives impedance data from these measurements.

As illustrated in FIG. 41A, the pre-processing module 1550 of the controller 1505 pre-processes and separates the measured data into desirable and undesirable data. The controller 1505 may run an algorithm to process the data obtained from various measurements and stored internally which may allow plotting of curves and various other statistical analyses to be done in order to find a set of EP parameters which yield the best EP results. In some embodiments, the undesirable data is stored in the memory module so as to flag subsequently collected data with similar properties as "undesirable" data as an additional safeguard.

In some embodiments, the data pre-processing may comprise data mining. Data-gathering methods are often loosely controlled, resulting in out-of-range values, impossible data combinations, missing values, etc. therefore analyzing data that has not been carefully screened for such undesirable data can produce misleading results. Thus, the data pre-processing carried out by the controller of the present invention provides necessary safeguards for quality in representation of the data. To this effect, sensor data is cleansed by removing outliers, out of range values, missing values, removing biases, scaling, cross-correlation, and applying de-noising routines. In some embodiments, a sensor validation routine is used to determine or assess the quality of data before features are extracted by the controller to estimate improved, and more ideally, optimized EP pulsing parameters.

In some embodiments. the pre-processing module of the controller may pre-process the data using any of the following:

De-noising filter—a digital filter that removes noise from the sensor signals. The filter may be implemented as an infinite impulse response (IIR) or finite impulse response (FIR) filter. This can also be implemented as an analog filter or part of the EP circuitry. Unbiasing—The AC signals measured by the sensors may be preprocessed by removing the DC bias from each of the signals. Scaling—the data may be based on standardized values such as standard deviation. Median filtering—the data may be filtered using a non-linear digital filtering technique. Outliers—the data may be processed to remove extreme values by identifying out of range values or values that exceed a specified number of standard deviations from the rest of the dataset. Sensor validation—the controller may carry out a routine by running an algorithm that analyzes the quality of the measured data using statistical measures such as standard deviation, number of outliers, skewness, and kurtosis, or any other known statistical measure for analyzing data quality. For example, if the standard deviation of the data exceeds a threshold, the data is flagged as the "undesirable data" or an un-usable dataset.

The adaptive control method of the present invention further comprises extracting relevant features from the desirable data by the feature extraction module 1570. By "features" it is meant values derived from the pre-processed data which are intended to be informative and non-redundant based on various characteristics of the pre-processed data. Features of the system may be estimated and controlled thus demonstrating that the system can be stabilized by the controller 1505.

In some embodiments, the feature extraction module is configured to execute certain software instructions for deriving relevant features from the pre-processed desirable data using computational routines. Characteristics of the pre-processed desirable data may be obtained using the computational routines including, but not limited to data descriptive statistics, data descriptive models, time-independent transforms, time-series transforms, domain dependent feature extraction.

In some embodiments, data descriptive statistics for sensor data may include but not be limited to mean, standard deviation, peak2peak, Root Mean Squared (RMS), variance, kurtosis, crest factor, correlation coefficient, auto correlation, and cross correlation. For events, data descriptive statistics may include count, occurrence rate, duration, and time delays. Data descriptive models may include distribution models, e.g. parametric distributions, histograms, regression models (use model parameters or modeling errors): curve fitting, Auto Regressive (AR) models, Classification/clustering models (using class label as a feature), sequence matching likelihood, Pattern recognition classifiers (Fisher discriminant, Bayes Theorem) Time-independent transforms may include explicit mathematical operations such as difference, summation, ratio, logarithm, power n, Principal component analysis, and Independent component analysis. Time series transforms may include frequency domain, time-frequency domain, and wavelet domain. Domain dependent feature extraction may include physics based features such as expected input-output or output-output relations, derived hidden states, and special procedures for data processing such as operational regime segmentations, and envelope analysis.

In some embodiments, the features are derived from a parametric model fit of magnitude ratio or phase difference of the excitation voltage and current signals. Such data includes, but is not limited to, intracellular resistance, extracellular resistance, solution resistance, membrane capacitance, admittance, constant phase element exponent, and charging time constant. Feature extraction by the feature extraction module may include determining capacitance or impedance of cell membranes of cells resulting from the applied excitation signals. In these embodiments, the impedance may be determined from the measurement of dielectric and conductive properties of cells and tissues resulting from the applied excitation signals by applying band-limited signals repeated over a fixed frequency range. Dielectric and conductive properties of the cells or tissue are determined by the magnitude ratio and phase difference of the excitation voltage and current applied to the cells or tissue. The controller 1505 may compute the magnitude and phase of each applied excitation and fit these to the equivalent circuit model of the tissue described above. In the model, resistive elements ($R_I$ and $R_E$) are due to the intracellular and extracellular matrix, respectively, and lipid structures are represented by the constant phase element ($CPE_M$). $CPE_M$ is a function that represents the charge or capacitance of lipid bilayers (denoted by $Q_M$) and a scalar ranging from 0 to 1 representing the non-ideal nature of the capacitor (denoted by $\alpha$). The time-constant for charging the lipid bilayer, computed as $\tau=(R_I Q_m)^{1/\alpha}$, may be used by the pulse parameter estimation module to estimate the optimal EP pulse durations before each treatment.

The magnitude ratio and phase difference between the excitation voltage and the current signals applied to the cells and tissue is determined by cross-correlating the said excitation voltage and current signals with known reference signals stored in said memory module. Examples of features include, but are not limited to the following a) values of magnitude ratio and phase difference of said excitation voltage and current signals at fixed frequencies, b) at least one of a mean, median, maximum, and minimum of i) magnitude ratio or phase difference of said excitation voltage and current signals magnitude over a narrow frequency band, ii) magnitude ratio or phase difference of said excitation voltage and current signals magnitude phase over a wide frequency band, c) curvature, slope and noise of said magnitude ratio or phase difference of said excitation voltage and current signals with respect to frequency; d) constant phase elemental parameter, e) high frequency resistance (e.g. at 100 Hz); low frequency resistance (e.g. at 1 kHz), and f) capacitance.

Figure 40:
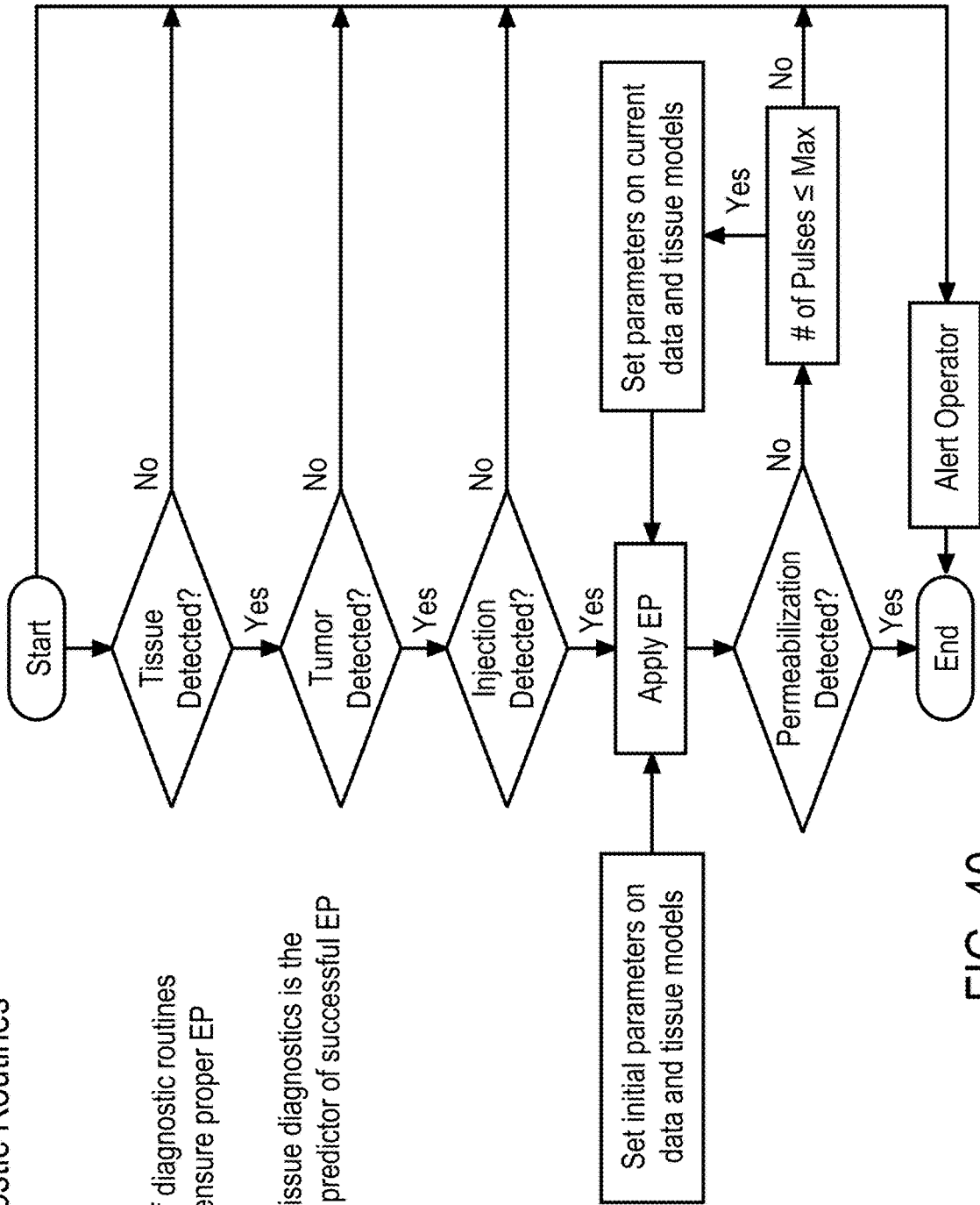
FIG. 40 is a flow-chart illustrating an EP diagnostics routine in the method for adaptive control of EP pulse parameters according to the present invention.

In some embodiments, the control method of the present invention includes applying at least a portion of the relevant features of the desirable data by the diagnostic module to the at least one trained diagnostic model, as illustrated in FIG. 40. A priori tissue diagnostics is important in prediction of successful EP. As illustrated in FIG. 40, the features are used as inputs to a series of diagnostic models for (i) tissue detection, (ii) tumor type detection, (iii) injection detection, and (iv) permeabilization detection. Based on the outcome of these models, the system will (i) terminate the treatment as a result of permeabilization, (ii) proceed to estimating the next pulse parameter, or (iii) stop and alert the operator of a diagnostic event (e.g. no tissue detected, no tumor detected, no injection detected). One or more statistical inferencing routines (e.g., a Bayesian Reasoner) will be used to combine or fuse multiple features for each diagnostic module. The system will include several diagnostic modules used to make decisions for the control input (applied pulse). In some embodiments, the control method comprises fitting or applying the derived features to the trained diagnostics model, by the controller, and observing fit of the data, where poor fit or correlation is an indicator of a diagnostics issue, e.g., improper electrode placement, for example in necrotic or fibrotic tissue, corrosion of electrodes. In some embodiments, a criteria for the tissue fit to the model, e.g. the CPE-based tissue model is $R^2 > 0.98$. The diagnostics module 1580 of the controller 1505 generates a diagnostic response, as described above, based at least in part on the outcome of the fitting or application, in which the diagnostic response includes tissue detection, tumor type detection, needle placement detection, cell permeabilization detection, colocalization diagnostic, pulse verification, and repulse diagnostic.

The diagnostics routines detailed above play an important role in the control methods of the present invention. One area where this is especially important is in colocalization detection. Overlapping electric field with injection is paramount to success of the EP process. Electrical measurements ensure abnormalities do not interfere with treatment. Examples of issues causing poor colocalization include but are not limited to injecting deeper than effective E-field, deflection of the injecting element, and biological anomalies in the tissues or cells. Experiments and studies conducted demonstrated that good colocalization is characterized by a drop in solution resistance of at least 10%. The present invention aims to achieve good or ideal colocalization at least in part by integrating therapeutic moiety delivery devices with EP electrodes in a single EP device or applicator. The diagnostic routines of the present invention performed by the diagnostics module ensure that EP is performed only after good colocalization is observed, tissue is detected, tumor is detected, and injection is detected. When the aforementioned conditions are met, the controller then applies the relevant features to the CPE-based tissue model to estimate initial pulsing parameters.

In some embodiments, as described above, the adaptive control method further includes estimating first pulsing parameters, by the pulse parameter estimation module, based on the outcome of the application of relevant features to the CPE-based tissue models after performance of the diagnostic routines and the feature extraction described above. That is, if tissue is detected, if a tumor is detected, and if injection is detected, the initialized EP pulsing parameters are based on the at least one trained model and said measured features to estimate improved or ideally, optimized first EP pulsing parameters. In some embodiments, as illustrated in FIGS. 36 and 37, features combined with past features will be used to determine future pulsing parameters. Estimators may include state-space estimation, artificial neural-networks, auto-regressive (AR), and auto-regressive moving average (ARMA) estimators.

In some embodiments, the control method further comprises applying a first EP pulse based on the estimated improved/optimized first pulsing parameters. Various embodiments of the pulsing sequence are illustrated in FIGS. 41A and 41B, where i=pulse sequence (for the excitation signals i=0, for the first applied EP pulse, i=1), and N=the number of pairs of electrodes. The adaptive control method may further comprise predicting subsequent EP pulsing parameters after the first EP pulse has been applied, using the trained CPE-based model based on a previous EP pulse parameter and voltage and current measurements of the cell's response to the first EP pulse, and a change in at least one of the features between applied EP pulses. As illustrated in FIG. 41B, the tissue sensing routines described above are repeated between applied EP pulses until optimized EP pulsing parameters are achieved or until a pulse limit is reached.

In some embodiments, the control method may further comprise a) applying a subsequent EP pulse based on the predicted subsequent EP pulsing parameters, and b) repeating the applying of the voltage and current excitation signals to the cells and tissue, repeating the measuring the cells or tissue, repeating the obtaining data and separating desirable data from undesirable data; repeating the extracting relevant features, and repeating the applying, until either i) a predetermined limit of number of EP pulse sequences or cycles of EP pulses is reached, or ii) the diagnostic response prompts a diagnostic decision to terminate the adaptive control method, as illustrated in FIGS. 41A and 41B. In some embodiments, the control method may be terminated and no further EP pulses applied when the time constant drops by 50%. At this point, the expression in all groups is statistically determined to be significantly different from the controls. As described above, the duration of EP pulses are modulated based on CPE-based model fit parameters, therefore EP is stopped when a relative change in CPE parameters reaches a level associated with therapeutically beneficial pDNA expression. This technology will allow a clinician to inject a therapeutic molecule, characterize the baseline state of the tissue, deliver optimized EP pulses for that tissue, and stop pulsing when a relative drop in membrane integrity is achieved. This removes any ambiguity associated with EP, and ensures successful delivery of immunotherapeutic genes regardless of variations in tumor properties.

VII. Therapeutic Moieties for Delivery

The present invention provides apparatus and methods for the improved delivery of therapeutic moieties to cells in a tissue of a patient. In general, the systems of the invention are used to treat diseased or abnormal tissue, such as cancerous tissues. The term "cancer" includes a myriad of diseases generally characterized by inappropriate cellular proliferation, abnormal or excessive cellular proliferation. The devices are contemplated for use in patients afflicted with cancer or other non-cancerous (benign) growths. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. Tumors treated with the devices and methods of the present embodiment may be any of noninvasive, invasive, superficial, papillary, flat, metastatic, localized, unicentric, multicentric, low grade, and high grade. Examples of cancer include but are not limited to, breast cancer, colon cancer, prostate cancer, pancreatic cancer, skin cancers (including melanoma, basal cell carcinoma and squamous cell carcinoma), lung cancer, ovarian cancer, kidney cancer, brain cancer, or sarcomas, adrenal cortical cancer, anal cancer, bile duct cancer (e.g. periphilar cancer, distal bile duct cancer, intrahepatic bile duct cancer) bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adenocarcinoma, clear cell) esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer, both melanoma and non-melanoma skin caner), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma). Accordingly, cancerous tissues including skin tissue, connective tissues, adipose tissues, etc. can be treated using the systems of the invention. Such cancers may be caused by chromosomal abnormalities, degenerative growth and developmental disorders, mitogenic agents, ultraviolet radiation (UV), viral infections, inappropriate tissue expression of a gene, alterations in expression of a gene, or carcinogenic agents.

The term "treatment" includes, but is not limited to, inhibition or reduction of proliferation of cancer cells, destruction of cancer cells, prevention of proliferation of cancer cells or prevention of initiation of malignant cells or arrest or reversal of the progression of transformed premalignant cells to malignant disease or amelioration of the disease. The term "subject" or "patient" refers to any animal, preferably a mammal such as a human. Veterinary uses are also intended to be encompassed by this invention.

The systems and methods of the invention deliver therapeutic moieties to cells in a tissue in the electroporation zone. By "therapeutic moiety" or TM herein is meant a moiety suitable for electroporation that can treat diseased tissues, including cytotoxic agents, chemotherapeutic agents, toxins, radioisotopes, cytokines, or other therapeutically active agent. The therapeutic moieties can be small molecule drugs, nucleic acids (including those that encode therapeutic proteins of interest), or proteins (including polypeptides and peptides) that have biological activity as is more fully outlined herein.

In some embodiments, the TM is a drug; drugs contemplated for use in the method of the invention are typically chemotherapeutic agents having an antitumor or cytotoxic effect. Such drugs or agents include bleomycin, neocarcinostatin, suramin, doxorubicin, carboplatin, taxol, mitomycin C, and cisplatin. Other chemotherapeutic agents will be known to those of ordinary skill in the art (see, for example, The Merck Index). Electroporation facilitates entry of bleomycin or other similar drugs into the tumor cell by creating pores in the cell membrane. This local delivery provides significant benefits as the normal systemic toxicity normally associated with such drugs is minimized via the local administration of the EP methods herein.

In some embodiments, the TM is a biologic molecule, including nucleic acids and proteins.

In some embodiments, the TM is a nucleic acid. In general, TMs that are nucleic acids are of two different functional types. In one embodiment, the nucleic acids encode proteins that are used to treat the disease; in others, the nucleic acid is the TM, for example when the nucleic acid is siRNA or snRNA. By "nucleic acid" or "oligonucleotide" or grammatical equivalents herein means at least two nucleosides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to increase the stability and half-life of such molecules in physiological environments, for example when the nucleic acids are siRNA, etc.

In many embodiments, the nucleic acids of the invention are contained within one or more expression vectors, that contain additional nucleic acid sequences that confer functionality on the expression vector, including but not limited to, promoters, regulatory sequences, etc.

In some embodiments, the nucleic acid is DNA or RNA encoding a therapeutic proteinaceous moiety, such as antibodies and cytokines.

In some embodiments, the nucleic acid encodes an immunostimulatory cytokine as outlined herein. The phrase "immunostimulatory cytokine" includes cytokines that mediate or enhance the immune response to a foreign antigen, including viral, bacterial, or tumor antigens. Innate immunostimulatory cytokines can include, e.g., TNF-α, IL-1, IL-10, IL-12, IL-15, type I interferons (IFN-α and IFN-β), IFN-γ, and chemokines. Adaptive immunostimulatory cytokines include, e.g., IL-2, IL-4, IL-5, TGF-β, IL-10 and IFN-γ. Examples of immunostimulatory cytokines are provided in Table 1 below.

TABLE 1

Immunostimulatory Cytokines Accession Numbers

| Cytokine | GenBank Accession Number - Mouse Nucleic Acid | GenBank Accession Number - Mouse Amino Acid | GenBank Accession Number - Human Nucleic Acid | GenBank Accession Number - Human Amino Acid |
|---|---|---|---|---|
| TNFα | M20155 | CAA68530 | X02910 | ADV31546 |
| IL-1 | RNU48592 | CAA28637 | X03833 | CAA27448 |
| IL-10 | MUSIL10Z | AAA39275 | HSU16720 | AAA80104 |
| IL-12 | | | | AAD16432 |
| p35 | NM_001159424.2 | NP_001152896.1 | NM_000882.3 | NP_000873.2 |
| p40 | NM_001303244.1 | NP_001290173.1 | NM_002187.2 | NP_002178.2 |
| IL-15 | NM_001254747.1 | NP_001241676 | NM_000585.4 | NP_000576 |
| IL-15Rα | NM_008358.2 | NP_032384 | NM_002189.3 | NP_002180 |
| IFNα | NM_010502.2 | NP_034632.2. | NM_006900.3. | NP_008831.3 |
| | | | NM_024013.2. | NP_076918.1 |
| IFNβ | NM_010510.1 | NP_034640.1 | NM_002176.3. | NP_002167.1. |
| IFNγ | NM_008337.4. | NP_032363.1. | NM_000619.2. | NP_000610.2 |
| IL-2 | NM_008366.3. | NP_032392.1. | NM_000586.3. | NP_000577.2. |
| TGFβ | NM_011577.2. | NP_035707.1 | NM_000660.5. | NP_000651.3. |

An immunostimulatory cytokine that finds particular use in the present invention is IL-12.

In some embodiments, the nucleic acid encodes a therapeutic antibody. Generally, in this embodiment, there are two nucleic acids that are electroporated into the tissue, one encoding a heavy chain and one encoding a light chain. In some cases, these can be in a single expression vector or two expression vectors can be used as is more fully described below.

The term "antibody" is used generally. Antibodies that find use in the present invention can take on a number of formats as described herein, including traditional antibodies as well as antibody derivatives, fragments and mimetics, described below. Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4, with the former finding particular utility in a number of applications, particularly oncology. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

In some embodiments, the antibodies are full length. By "full length antibody" herein is meant the structure that constitutes the natural biological form of an antibody, including variable and constant regions, optionally including one or more amino acid modifications as is known in the art. Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

As will be appreciated by those in the art, there are a wide variety of suitable therapeutic antibodies that can be used in the present invention, depending on the type and location of the cancer. Suitable therapeutic antibodies include, but are not limited to, human, humanized or chimeric antibodies of therapeutic use in humans, including currently approved antibodies identical or similar to muromonab, abciximab, rituximab, daclizumab, basiliximab, palivizumab, infliximab, trastuzumab, gemtuzumab, alemtuzumab, ibritumomab, adalimumab, omalizumab, tositumomab, efalizumab, ceruximab, bevacizumab, natalizumab, nivolumab, pembrolizumab and pidilizumab MPDL328OA (ROCHE), as well as antibodies under clinical development, particularly those in oncology applications.

In addition, the present invention provides EP methods and devices that deliver therapeutic antibodies to immune checkpoint inhibitors. As used herein, "immune checkpoint" molecules refers to a group of immune cell surface receptor/ligands which induce T cell dysfunction or apoptosis. These immune inhibitory targets attenuate excessive immune reactions and ensure self-tolerance. Tumor cells harness the suppressive effects of these checkpoint molecules. Immune checkpoint target molecules include, but are not limited to, the checkpoint targets described in Table 2.

TABLE 2

Checkpoint Targets Accession Numbers

| Target | Unabbreviated Name | GenBank Accession Number - Mouse Nucleic Acid | GenBank Accession Number - Mouse Amino Acid | GenBank Accession Number - Human Nucleic Acid | GenBank Accession Number - Human Amino Acid |
|---|---|---|---|---|---|
| CTLA-4 | Cytotoxic T Lymphocyte Antigen-4 | U90271 | AAD00697 | L15006 | AAL07473 |
| PD-1 | Programmed Death 1 | NM_008798.2 | MP_032824 | NM_005018 | NP_005009.2 |
| PD-L1 | Programmed Death Ligand 1 | GQ904197 | ADK70950 | AY254342 | AAP13470 |
| LAG-3 | Lymphocyte Activation Gene-3 | AY230414 | AAP57397 | X51985 | CAA36243 |
| TIM3 | T cell Immunoglobulin Mucin-3 | AF450241 | AAL35776 | JX049979 | AFO66593 |
| KIR | Killer Cell Imunoglobulin-like Receptor | AY130461 | AY130461.1 | AY601812 | AAT11793 |

TABLE 2-continued

Checkpoint Targets Accession Numbers

| Target | Unabbreviated Name | GenBank Accession Number - Mouse Nucleic Acid | GenBank Accession Number - Mouse Amino Acid | GenBank Accession Number - Human Nucleic Acid | GenBank Accession Number - Human Amino Acid |
| --- | --- | --- | --- | --- | --- |
| BTLA | B- and T-Lymphocyte Attenuator | AY293285 | AAP44002 | AY293286 | AAP44003 |
| A2aR | Adenosine A2a Receptor | NM_009630 | NP_033760 | NP_001265428 | NM_001278499 |
| HVEM | Herpes Virus Entry Mediator | AF515707 | AAQ08183 | AY358879 | AAQ89238 |

The phrase "immune checkpoint inhibitor" includes molecules that prevent immune suppression by blocking the effects of immune checkpoint molecules. Checkpoint inhibitors can include antibodies and antibody fragments, nanobodies, diabodies, scFvs, soluble binding partners of checkpoint molecules, small molecule therapeutics, peptide antagonists, etc. Inhibitors include, but are not limited to, to the checkpoint inhibitors described in Table 2.

In some embodiments, the EP methods and devices are used in combination therapies, e.g. the delivery of two different TMs for higher efficacy. As will be appreciated by those in the art, the combinations can be of any of the TMs outlined herein, including, but not limited to, a) a nucleic acid encoding a therapeutic biologic molecule (including expression vectors as more fully described below) and a small molecule drug, for example a plasmid encoding IL-12 and a drug as outlined above; b) a first nucleic acid encoding a first therapeutic biologic molecule and second nucleic acid(s) encoding a second therapeutic biologic molecule (e.g. an expression vector encoding IL-12 and two nucleic acids encoding an anti-immune checkpoint inhibitor antibody as described herein), and c) a first nucleic acid encoding a first biologic molecule and a second proteinaceous molecule such as an anti-immune checkpoint inhibitor antibody; and d) two small molecule oncology drugs.

In some embodiments, the EP methods and devices of the invention are used in immuno-oncology combination therapies. In this embodiment, a combination therapy of an immunostimulatory cytokine therapy (as above) and a checkpoint inhibitor is administered to the patient.

In one embodiment, the immunostimulatory cytokine is administered in the form of a plasmid containing nucleic acid encoding the immunostimulatory cytokine, and the checkpoint inhibitor is administered as a protein (e.g. an antibody to a checkpoint inhibitor) into the cells and tissues.

In another embodiment, the immunostimulatory cytokine is administered in the form of a expression vector plasmid containing nucleic acid encoding the immunostimulatory cytokine, and the checkpoint inhibitor is administered similarly as one or more expression vectors comprising a first nucleic acid encoding a heavy chain of the anti-checkpoint inhibitor antibody and a second nucleic acid encoding a light chain of the anti-checkpoint inhibitor antibody.

In this embodiment, one, two or three vectors can be used: if one is used, it contains the coding sequences (as well as the appropriate regulatory sequences) to express the immunostimulatory cytokine and the heavy and light chains of the anti-checkpoint inhibitor antibody. Alternatively, three expression vectors can be used, each coding one of the above. Two expression vectors can also be used, with one containing one component (the immunostimulatory cytokine, for example) and the other containing two components (the heavy and light chains of an anti-immune checkpoint inhibitor antibody, for example).

In addition, a small molecule drug can also be delivered in any combination with the above.

Furthermore, the administration of the anti-checkpoint inhibitor (and/or a small molecule drug, as outlined above), can be done systemically rather than as an EP treatment to achieve efficacy as well.

Administration of the combination therapies can be achieved by electroporation alone or a combination of electroporation and systemic delivery.

Other contemplated combination therapies are checkpoint inhibitors combined with: TLR agonists (e.g., Flagellin, CpG); IL-10 antagonists (e.g., anti-IL-10 or anti-IL-10R antibodies); TGF-β antagonists, CD3 agonists; telomerase antagonists, etc.

VIII. Examples

Example 1

OncoSec built an EP generator A, illustrated in FIG. 16, capable of performing real-time feedback control based on EIS data before and between each EP pulse. This system can output a minimum of 10V and maximum of 300 V with pulse durations ranging from 100 s to 10 ms. EIS data captured before and between pulses is obtained over a range of 100 Hz to 10 kHz with 10 data points acquired per decade. Acquisition of EIS data over this spectra is accomplished in 250 ms, which is rapid enough to: (1) execute routines to determine a time constant for the next pulse; (2) store EIS data for post analysis; and (3) not interrupt clinically used EP conditions. Data gathered from the EIS system is fit to the tissue impedance model, described above, in real-time using an embedded Advanced RISC Machine (ARM) microprocessor (STM32F407, ST Microelectronics). When operating in feedback mode, features of this data can be used to control parameters associated with the EP process. The custom generator interfaces with a variety of standard EP applicators, and will support up to 6 electrodes. Solid state relays are used to switch between high voltage EP pulse circuitry and low voltage EIS interrogation circuitry. To allow hands-free operation of the generator a foot pedal was added to trigger, pause, or abort the EP process. An image of this generator and its accessories is shown in FIG. 16.

Unpublished studies performed in vivo investigated the effect of varying pulse widths based on time constant data acquired from EIS spectra. These studies were performed with MC38 tumors implanted in the flank skin of 8-week-old albino B6 mice. At the time of treatment tumor volumes averaged 75 mm³. Tumors were injected with 50 µg of pDNA encoding the luciferase protein under control of a CMV promoter. A prototype applicator C including an EP device, shown in FIG. 16, was used to perform both injections and EP. This applicator contains two EP electrodes around a central injection lumen; during EP the injection lumen is retracted. Electroporation was performed at an e-field strength of 350 V/cm and pulse widths were modulated in real-time from 0.1 to 20.0 multiples of the time constant computed from EIS data gathered before pulsing each MC38 tumor. A total of 8 pulses was applied to each tumor, as this previously has correlated with a high degree of transfection. Luminescence data was acquired at 48 hours by injecting 200 µl of a 15 mg/ml D-luciferin solution prepared in DPBS and performing in vivo optical imaging. Summary data from this experiment is shown in FIGS. 42A-42D.

Figure 42B:
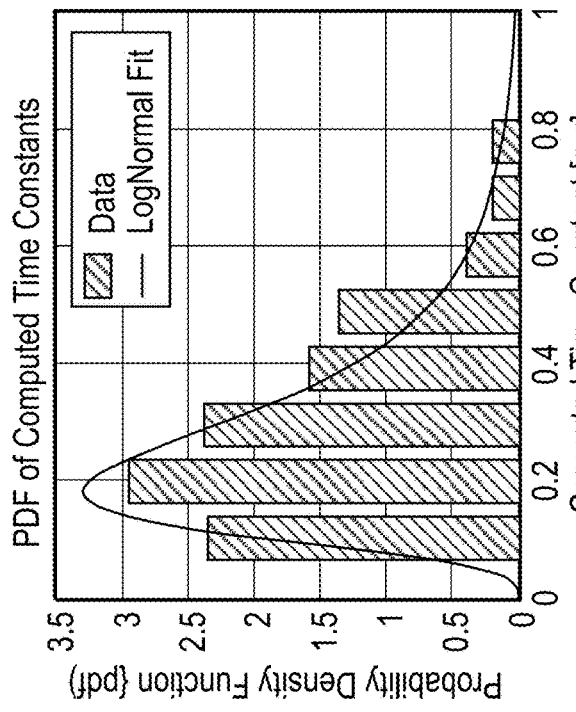
FIG. 42B illustrates distribution of time constants measured before EP.
Figure 42D:
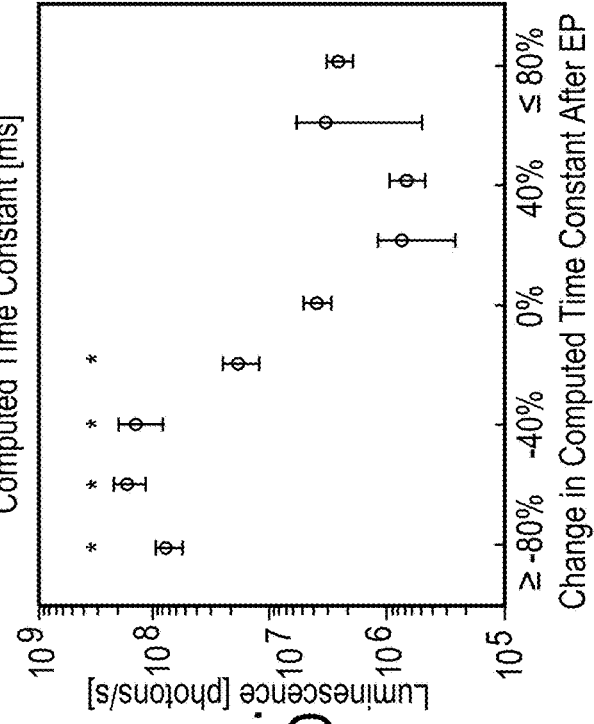
FIG. 42D illustrates data showing the relative change in computed time constant after EP with respect to resulting luminescence, according to the present invention.
Figure 42A:
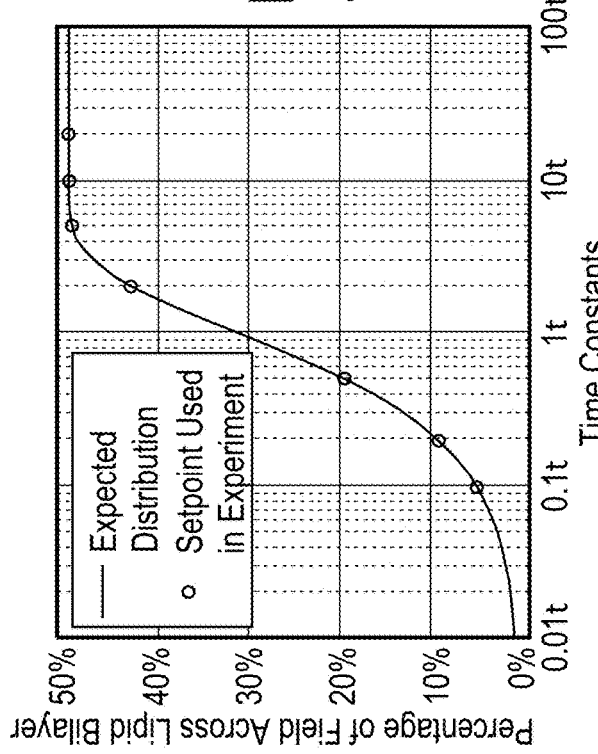
FIG. 42A illustrates distribution of percent applied electric field across the lipid bilayer vs. time constant.
Figure 42C:
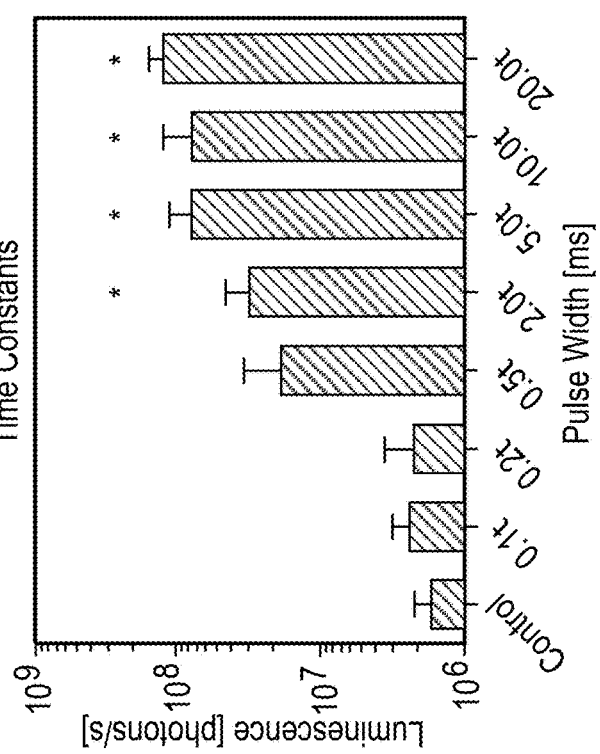
FIG. 42C illustrates effect of modulating pulse width based on pre-pulse EIS data, where pulse durations are set at a multiple of the time constant for each tumor.
Figure 43A:
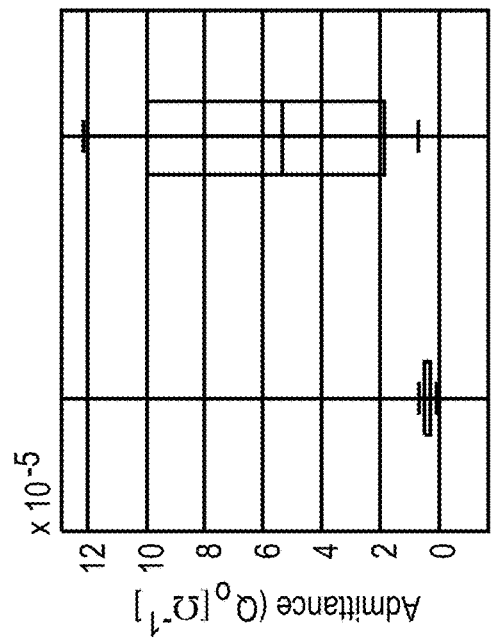
FIG. 43 illustrates model fit parameters for normal C57Bl/6J mice and transgenic PDGF-C mice where parameters represented are (A) solution resistance, (B) admittance, (C) constant phase element (CPE), and (D) computed time constant.
Figure 43B:
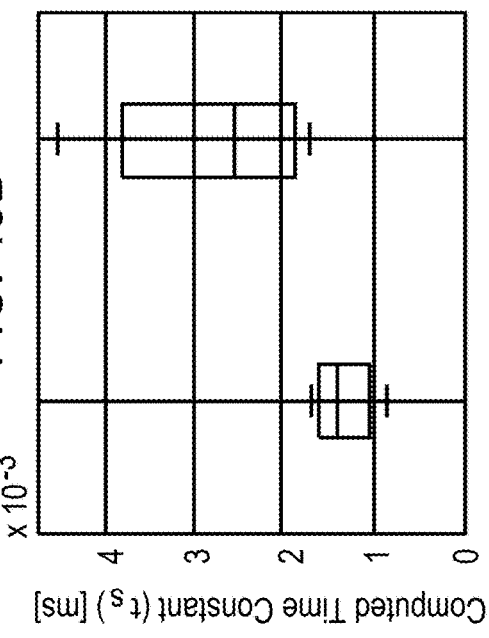
Figure 43C:
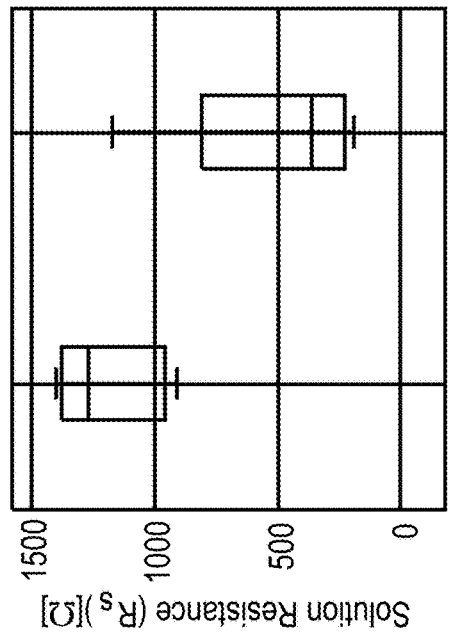
Figure 43D:
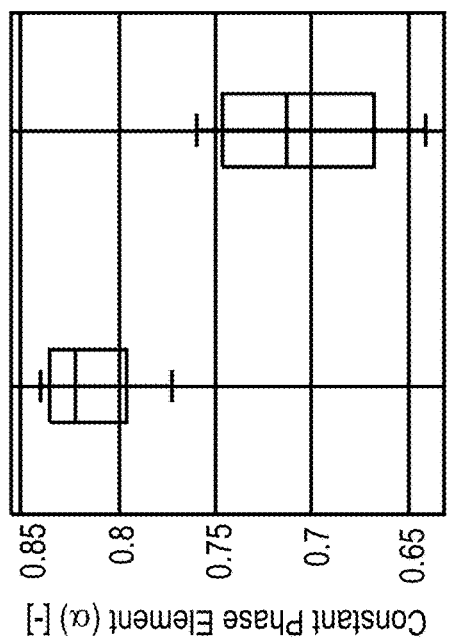

FIG. 42A illustrates distribution of percent applied electric field across the lipid bilayer vs. time constant. FIG. 42B illustrates distribution of time constants measured before EP. FIG. 42C illustrates effect of modulating pulse width based on pre-pulse EIS data, where pulse durations are set at a multiple of the time constant for each tumor. FIG. 42D illustrates data showing the relative change in computed time constant after EP with respect to resulting luminescence. Data found statistically significant at c=0.05 is denoted by an asterisk.

These data show expression of pDNA is dependent upon the applied pulse width. It was originally hypothesized that as the applied pulse width increases with respect to the measured time constant, the percentage of the e-field applied across the lipid bilayer would increase according to FIG. 42A. This is particularly important as the computed time constants from the EIS data before each EP treatment follows a log-normal distribution, shown in FIG. 42B. The results of the experiment in FIG. 42C shows as the applied pulse widths increases, with respect to the measured time-constants, the resulting luminescence also increases. This phenomenon supported the hypothesis as capacitors approach charge saturation at 5 time constants, the measured expression reaches an upper limit. Data sets acquired above two time constants had significantly ($p<0.05$) higher luminescence when compared to injection alone. As pulse widths become longer and more energy is dissipated through the tissue, expression will begin to diminish as irreversible tissue damage occurs.

Additionally, this experiment demonstrated a potential criteria to cease the EP process prior to reaching a previously determined terminal number of pulses. As cell membranes begin to permeabilize their ability to hold a charge decreases, which in turn causes a decrease in the time constant associated with charging CPEs. Supporting this theory, a high degree of correlation was observed between changes in the time constant and measured luminescence. Tumors with time constant drops of greater than 20% correlated with significantly ($p<0.05$) higher expression of pDNA. This measurement can be used to stop the pulsing process when conditions for successful gene therapy are present. Interestingly, groups with short pulse durations caused an increase in time constant, due to compression of lipid bilayers that causes an increase in capacitance. For this study, we propose to utilize the prototype generator to explore the variables for controlling EP and validate this technique in homogeneous and heterogeneous tumors. We hypothesize EP-based gene delivery can be optimized for each tumor by measuring tissue properties and adjusting each applied pulse width. Interrogation of real-time changes in membrane capacitance will lead to (1) reproducible transfection efficiency; (2) increased duration of gene expression; (3) enhanced therapeutic efficacy; and (4) reduced tissue damage.

Example 2

An experiment was performed to determine if electrochemical impedance spectroscopy (EIS) could differentiate between data acquired in fibrotic or necrotic tissues from data acquired in healthy tissues. In these experiments, livers of 9-month-old transgenic mice expressing human platelet derived growth factor C (PDGF-C) were used to represent fibrotic tissues. By this age PDGF-C transgenic mice are known to have enlarged livers with significant fibrosis, fat infiltrate, and cell dysplasia. Data acquired from livers of transgenic animals was compared to healthy, or wild type, 3-month-old C57Bl/6J livers. To acquire this data mice were anesthetized to allow surgical access to the liver. Parallel electrodes, spaced 3 mm apart, were inserted 5 mm into the left lateral lobe of the liver. Data collected from this experiment was fit to a constant phase element model used to electrically represent biological tissues. Parameters derived from the model fit revealed liver fibrosis resulted in an increase in admittance, increase in computed time constant, and reduction in constant phase element. These data are displayed in FIG. 43.

Example 3

Figure 44:
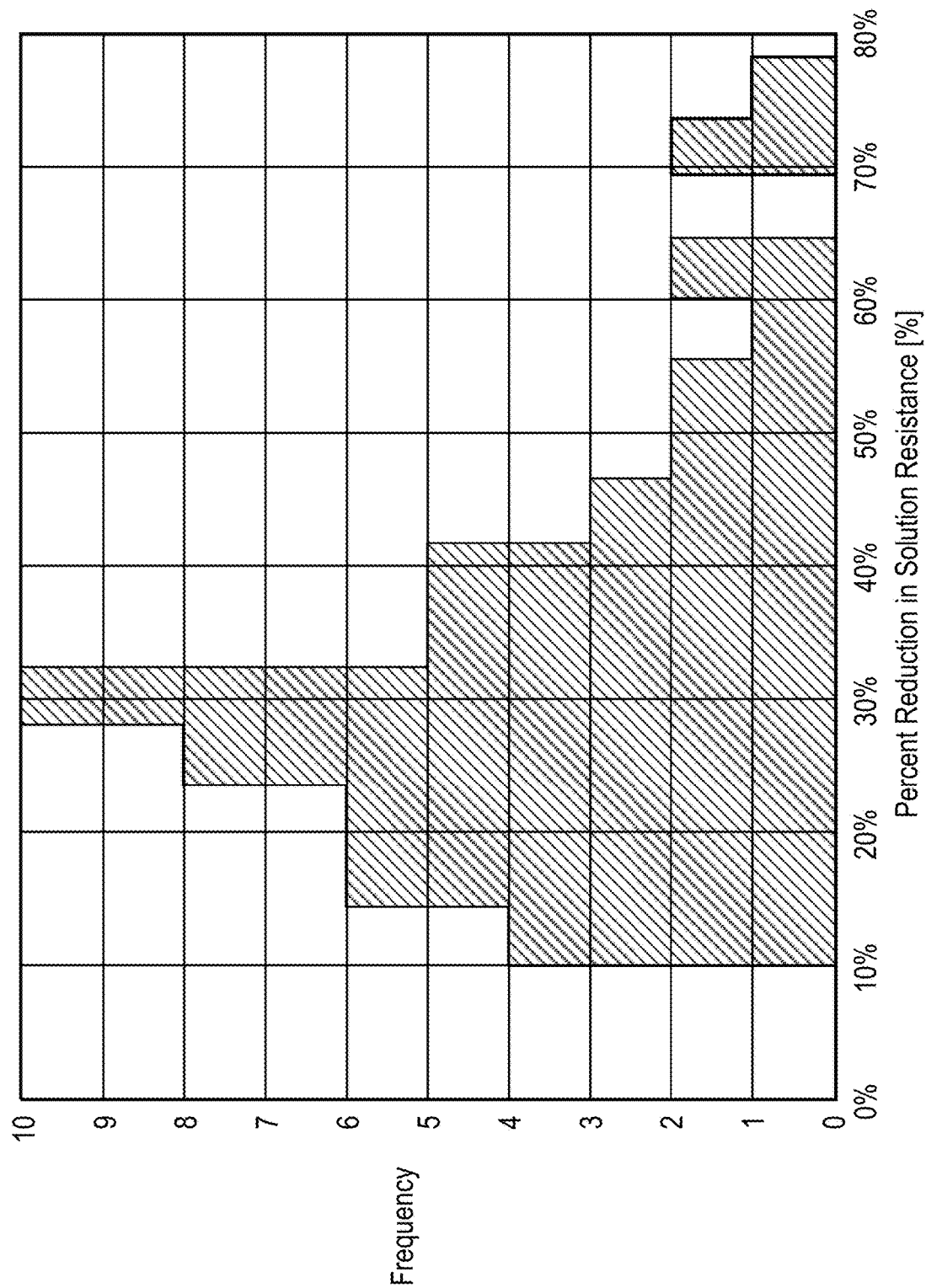
FIG. 44 illustrates a histogram of percent reduction in solution resistance following injection of plasmid DNA.

A second experiment was performed to determine if EIS could detect the presence of an injectate in tumor tissue. In this experiment, tumors were implanted in the subcutaneous tissue on the flank skin of 8-week-old albino B6 mice by injecting 106 MC38 cells in 50 µl of phosphate buffered saline. After approximately 10 days, tumors reached an average volume of 100 mm3. At this time a two-electrode applicator with a central injection lumen was inserted 7 mm into the tumor. A baseline EIS measurement of the initial condition of the tumor was then taken. After this measurement, a volume of 50 µl of a 1 mg/ml solution of plasmid DNA prepared in physiological saline was injected into the tumor. Following injection a second EIS measurement was performed. Again these data were fit to a constant phase element model used to represent biological tissues. A drop in solution resistance of at least 10% was observed after injecting the tumor with the plasmid DNA solution. FIG. 44 provides a histogram summary of the percent reduction in solution resistance observed from the model fit parameters after injection of plasmid DNA.

Example 4

Figure 45:
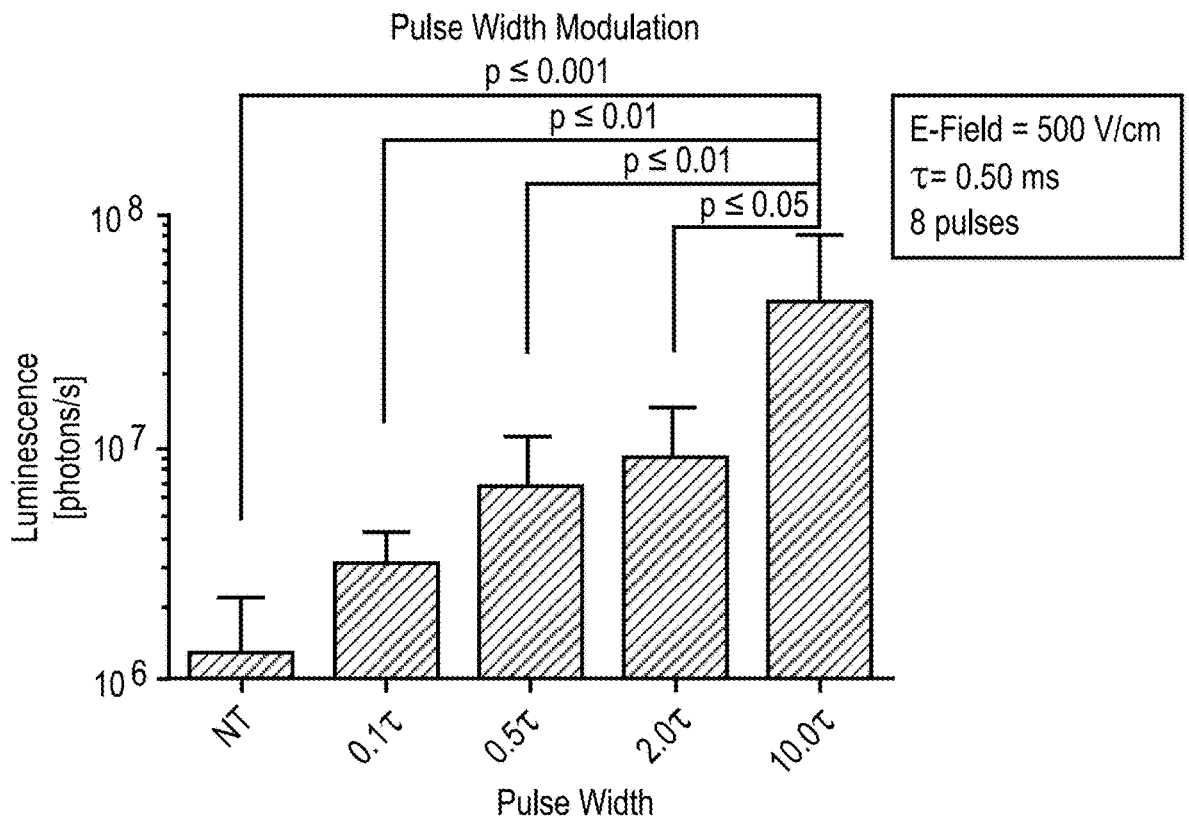
FIG. 45 illustrates luminescence data observed 48 hours after intratumoral EP with 50 µg of plasmid DNA expressing luciferase. EP conditions were set at 500 V/cm, 8 pulses were applied, and the duration was set at a multiple of the computed average time constant.

In addition to detecting the viability of the tissue and presence of injection, EIS can also inform the user of the optimum pulse width to perform electroporation. To demonstrate this, a study was performed that varied pulse widths based on time constant data acquired from model fits of EIS spectra. This study was performed with MC38 tumors implanted in the flank skin of 8-week-old albino B6 mice. At the time of treatment tumor volumes averaged 75 mm³. Tumors were injected with 50 µg of pDNA encoding the luciferase protein under control of a CMV promoter. A two-electrode applicator with a central injection lumen was used to perform injections and EP. During EP the injection lumen is retracted from the tumor. Electroporation was performed with a field strength of 500 V/cm and pulse widths were modulated around an average time constant obtained a priori from 10 tumors. This average computed time constant was 0.50 ms and pulse widths selected for this experiment were 0.1, 0.5, 2.0, and 10.0 multiples of the average time constant. A total of 8 pulses were applied to each tumor. Luminescence data was acquired at 48 hours following injecting 200 µl of a 15 mg/ml D-luciferin solution prepared in D-PBS. This data was gathered with in vivo optical imaging. Data from this experiment showed a maximum rise in luminescence for tumors treated with 10 multiples of the average time constant, or a total pulse width of 5 ms. Additionally, these data showed groups treated with two or more time constants had a significant rise in luminescence compared to injection alone. Summary data from this experiment is shown in FIG. 45.

Example 5

Figure 46:
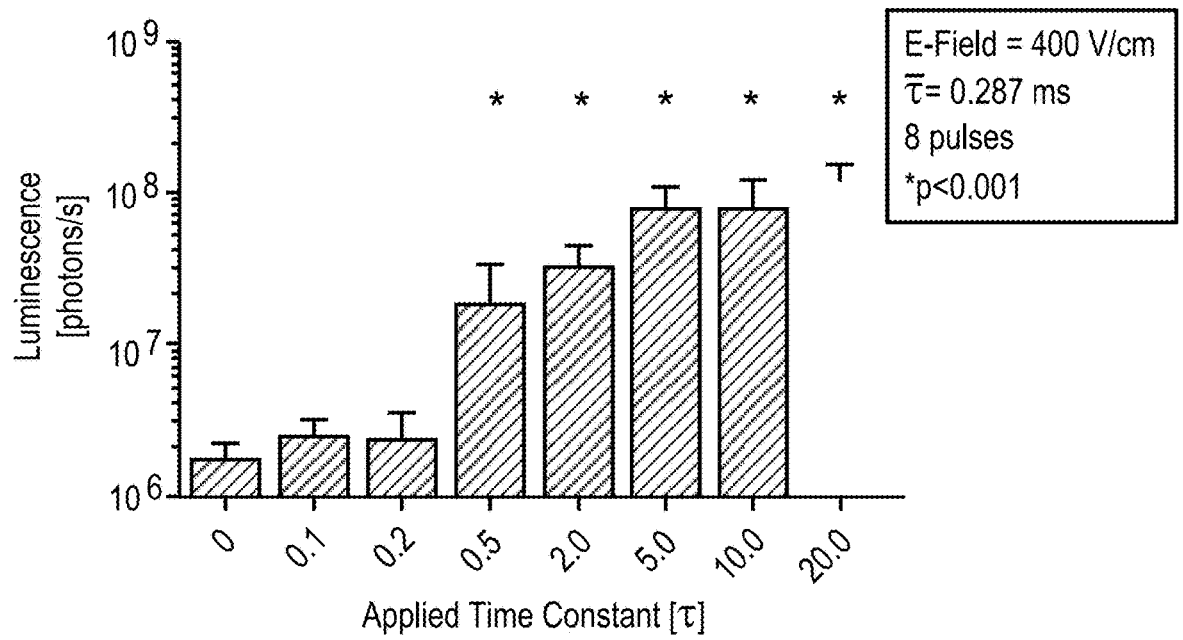
FIG. 46: Luminescence data observed 48 hours after intratumoral EP with 50 µg of plasmid DNA expressing luciferase. EP conditions were set at 350 V/cm, 8 pulses were applied, and the duration was set at a multiple of the computed time constant for each individual tumor.

Following the experiment conducted in Example 4, a study was performed to determine if EIS could be used in real-time to augment optimum pulse widths for each individual tumor. This would allow each electroporation sequence to be tailored to the initial conditions of each individual tumor. Again MC38 tumors were implanted in the flank skin of 8-week-old albino B6 mice. When tumors reached 75 mm3 they were injected with 50 µg of pDNA encoding the luciferase protein. The same two-electrode applicator with a central injection lumen was used to perform injections and EP. For this experiment the field strength was reduced to 350 V/cm and pulse widths were modulated in real-time using the computed time constant for each tumor being treated. Pulse widths were modulated from 0.1 to 20.0 multiples of the computed time constant. A total of 8 pulses were applied to each tumor. Luminescence data was acquired by in vivo optical imaging at 48 hours by injecting 200 µl of a 15 mg/ml D-luciferin solution. Data from this experiment showed a significant rise in luminescence for all tumors treated with and above 2.0 time constants. No statistical differences were observed between groups at 5.0, 10.0, and 20.0 multiples of the computed time constant. Data from this experiment is shown in FIG. 46.

Figure 47:
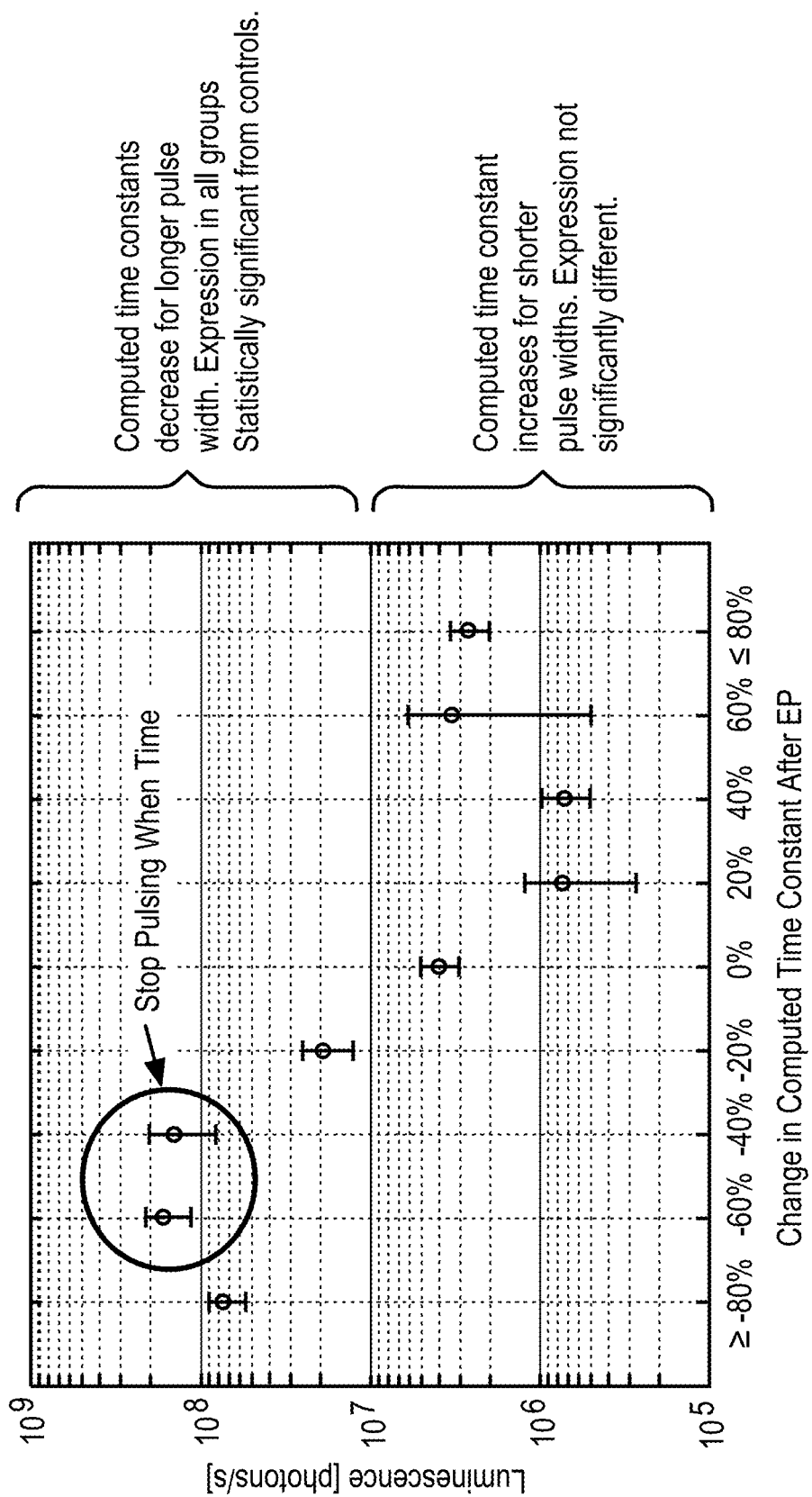
FIG. 47: Luminescence data plotted as a function of the change in computed time constant after electroporation. Longer pulsed resulted in a drop in the computed time constant, where groups greater than 20% were significantly different than controls. Short pulses resulted in an increase in the computed time constant.

Post processing of data acquired during the course of this experiment demonstrated potential criteria to cease the EP process prior to reaching a previously determined terminal number of pulses. As cell membranes begin to permeabilize their ability to hold a charge decreases, which in turn causes a decrease in the time constant associated with charging CPEs. Supporting this theory, a high degree of correlation was observed between changes in the time constant and measured luminescence. Tumors with time constant drops of greater than 20% correlated with significantly higher expression of pDNA. This measurement can be used to stop the pulsing process when conditions for successful gene therapy are present. Interestingly, groups with short pulse durations caused an increase in time constant, due to compression of lipid bilayers that causes an increase in capacitance. These data are shown in FIG. 47.

Example 6: (Anticipated Experiments)

The aim (Aim 1) is to evaluate feedback parameters that result in a desired outcome for intratumoral immunotherapy. Based on preliminary research, EP integrated with EIS feedback control has the potential to reduce treatment-to-treatment variability. To assess pDNA expression and histological effects of controlling EP based on changes in computed time constants in vivo tumor studies will be performed in a homogenous contralateral murine melanoma model. Briefly, B16/OVA cells (1×106/site) will be sub-dermally implanted in the flanks of B6 albino mice (n=10/group). When tumors reach a volume of 75 mm3, they will be injected with a dual reporter plasmid (1 mg/ml, 50 µl per tumor), which expresses both luciferase and mCherry. This will allow non-invasive, longitudinal bioluminescent imaging and spatial cell-specific gene expression. Tumors will be pulsed with FCEP using the dual electrode applicator C in FIG. 16. Electrodes will be operated at 350 V/cm with pulse widths set for each individual pulse at five computed time constants. Cells will continue to receive EP pulses until a relative drop in time constant of 20, 40, 60, or 80% is reached. Operational limits of the generator will be set to ensure safety, where the maximum pulse width allowed will be fixed at 10 ms and the maximum pulses will be set at 10. Control animals for this experiment will consist of no treatment, pDNA injection only, and pDNA injection followed by uncontrolled EP with 10 pulses 10 ms in duration with an e-field strength of 350 V/cm using the same electrode.

Bioluminescence will be quantified beginning at 24 hours by injecting D-luciferin (i.p. 200 µl of 15 mg/ml). Luminescence from these tumors will be captured with an in vivo imaging system (Lago, Spectral Instruments) at 24, 48, and 72 hours. Tumor tissue will be harvested, bisected lengthwise with half frozen in optimal cutting temperature compound (OTC) and half fixed in formalin for routine histologic analysis. Three independent experiments will be performed, where each experimental group consists of twelve biological replicates. Data will be analyzed using a one-way analysis of variance (i.e. Kruskal-Wallis, GraphPad Prizm).

Routine histology and immunohistochemistry (IHC) will be performed on tumor sections to evaluate necrosis, and specific forms of cell death, such as apoptosis in spatial relation to mCherry expression. TdT-mediated dUTP nick end labeling (TUNEL) and active caspase 3 IHC will be performed and sections will be assessed to score the extent of apoptosis. A semi-quantitative analysis will be performed as described using an Image J script. H&E stained slides will be used to evaluate inflammatory infiltrates and degree of necrosis.

Anticipated Results—FCEP should lead to a reduction in the variability of expression between treated tumors. A greater amount of pDNA transfection is expected to correlate with higher relative drops in computed time constants. Additionally, it is expected that more apoptosis and inflammation will be observed as relative drop in time constant increases.

Example 7: (Anticipated Experiments)

The aim (Aim 2) is to verify feedback control system in vivo by performing intratumoral immunotherapy experiment aimed at tumor regression.

Following in vivo characterization a set of experiments will be performed to verify tumor regression and durability of expression with the FCEP system. To compare with published studies and control variability a homogeneous melanoma model with contralateral tumors will be used. B16/OVA melanoma cells (1×106/injection site) will be sub-dermally implanted in the flanks of albino B6 mice (n=10/group). When tumors are 75 mm3, one tumor on each mouse will be injected with a polycistronic plasmid encoding interleukin-12 (IL-12), luciferase, and mCherry (50 µl at 1 mg/ml). Expression of this plasmid allows for immunotherapy and long-term bioluminescent quantification. Tumors will be pulsed with the FCEP system using 350 V/cm with pulse widths set for each individual pulse at five time constants. The EP stopping criteria for the first group will be selected based from the feedback control group in Aim 1 with the maximum expression of pDNA irrespective of observed histological features. A second feedback group will be chosen from Aim 1 by selecting the group showing a significant amount of expression with the least tissue damage. Control animals for this experiment will consist of no treatment, pDNA injection only, and pDNA injection followed by conditions optimized for this tumor model. To apply these conditions a MedPulser with a 6-electrode applicator will be used to apply 6 rotating pulses each 100 s in duration and having an e-field strength of 1,500 V/cm.

Data from these experiments will be collected in two different ways. Tumor growth rates for the treated and contralateral tumors will be collected with two dimensional caliper measurements every 48 hours following treatment. Luminescence data from the treated tumors will be quantified by injection of D-luciferin (i.p. 200 µl at 15 mg/ml) beginning at 48 hours after treatment and every 4 days thereafter. Tumor volume and luminescent data will continue to be observed for up to 30 days or until tumor burden exceeds 1,000 mm3 at which time animals will be euthanized in accordance with an established IACUC protocol. Three independent experiments will be performed consisting of 12 animals per experimental group. Data will be analyzed using a one-way analysis of variance (Kruskal-Wallis).

In addition to monitoring tumor growth rates, tumor specific neoantigen CD8 responses will be ascertained by harvesting spleens at the end of the study. Spleens will be mechanically dissociated and red blood cells will be lysed by suspension in ACK buffer. Isolate splenocytes will be purified with cell separation media (Lympholyte-M, Cedarline) prior to staining. Purified cells will then be mixed with a tetramer solution (e.g SIINFEKL, TS-5001-2C, MBL). CD8 positive T cells then will be determined by flow cytometry analysis (LSR II, BD).

Anticipated Results—It is anticipated the FCEP device will generate greater IL-12 and IFN-γ relative to the published EP methods. A greater duration of plasmid expression and long-term survival rate for tumor-bearing animals treated with FCEP, due to assurances that treatment was successful. The enhanced survival rate will serve as an additional metric to evaluate this system, which should be higher than the traditional EP treatment group with an anticipated long-term survival rate of approximately 47%, based on a similar study, and control groups will likely not respond to the treatment.

Potential Problems and Alternatives—A possible issue is CD8 positive T cells may be difficult to assess in 30 days after treatment. In the event this occurs, a separate group of tumor-bearing animals will be treated with the conditions described in this aim. Tumors will be excised from euthanized animals 14 days after treatment.

Example 8: (Anticipated Experiments)

The aim (Aim 3) is to validate feedback control system by performing intratumoral EP in heterogeneous spontaneous breast cancer model.

Following optimization and verification in homogenous tumor models a set of experiments will be performed to validate FCEP with a heterogeneous model. These experiments will use a transgenic mouse model expressing the Polyoma Virus middle T antigen under the direction of the mouse mammary tumor virus promoter (MMTV-PyVT), which develop spontaneous palpable mammary tumors by 8-10 weeks of age. A plasmid expressing IL-12, luciferase, and mCherry (50 µl at 1 mg/ml) will be delivered into mammary tumors of MMTV-PyVT mice at 10 weeks of age. Tumors will be treated with 350 V/cm pulses using the stopping criteria from Aim 2 resulting in the longest mean survival. Control groups will consist of no treatment, pDNA injection only, and pDNA injection followed by applying the current clinical parameters of 6 pulses at 1,500 V/cm for 100 as. A total of 10 tumors will be treated with each treatment condition where two of these tumors will be treated in each mouse. The experiment will be run a total of three times.

Utilizing each of the proteins encoded by the plasmid will allow multiple data streams to be generated. Luminescence will be quantified by in vivo imaging every 72 hours for up to 21 days following injection of D-luciferin (i.p. 200 µl of 15 mg/ml). Cohorts of 5 animals will be euthanized and have tumors harvested at 7, 14, and 21 days. Collected tumors will be bisected to directly assess IL-12 expression and determine the percent of cells transfected. A portion of these excised tumors will be massed and homogenized. IL-12 expression will be quantified directly from these sampled by ELISA assay (R&D Systems). The other half of the tumor will be dissociated (Tumor Dissociation Kit, Miltenyl Biotec) and run through a flow cytometer (LSR II, BD) using optics specific for the mCherry protein. This will enable the percentage of transfected cells to be ascertained. Data will be analyzed using a one-way analysis of variance.

Anticipated Results—It is anticipated FCEP will generate more reproducible transfection of these heterogeneous tumors than the current clinical EP protocol. This will be directly measured by luminescence data and IL-12 expression. Additionally, it would be anticipated that this novel method correlate with the highest transfection percentage.

Potential Problems and Alternatives—A possible issue that could arise during the course of this study is the expression of IL-12 may be difficult to assess in tumors. In the event this occurs, an ELISA will be performed to directly measure luciferase levels. Additionally, the downstream cytokine interferon-gamma will be directly assessed as a surrogate of IL-12 expression.

Timeline. Completion of this phase I effort will be performed through within a 12 month period. It is anticipated that Aim 1 will last a total of 3 months. Aim 2 will be completed in 5 months. Finally, Aim 3 will be completed in 4 months. This timeline is outlined in FIG. 49.

What is claimed is:
1. A system for providing adaptive control to optimize electroporation (EP) pulse parameters during EP of cells and tissue using an EP device, said system comprising:
   a) a measurement device configured to measure dielectric and conductive properties of said cells and tissue, said measurement device including:
      i) a voltage sensor configured to measure voltages across said tissue resulting from each of an excitation signal and an EP pulse applied to said tissue; and
      ii) a current sensor configured to measure current across said tissue resulting from each of said excitation signal and said applied EP pulse;
   b) an initializing module configured to initialize EP pulsing parameters prior to performing an initial electroporation in said cells or tissue, said initialized EP pulsing parameters comprising at least an initial pulse width for the initial electroporation and being based at least in part on at least one trained model that is trained based at least in part on applying at least one machine learning algorithm, wherein the initial electroporation in said cells or tissue is performed prior to a subsequent electroporation in said cells or tissue;

c) a generator configured to apply at least one of said excitation signal and said EP pulse to said tissue, wherein said voltage sensor and said current sensor of said measurement device measure said voltages and said current across said cells of said tissue, respectively, in response to said application of said excitation signal;

d) a controller configured to receive a signal relating to measured sensor data from said measurement device, corresponding to at least one of said excitation signal and said EP pulse, to fit said measured sensor data to the at least one trained model and to process said measured sensor data into diagnostics and updated control parameters, wherein said controller comprises:
  i) a pre-processing module to receive said signal relating to said measured sensor data from said current and voltage measurements, and process said measured sensor data to separate desirable data from undesirable data;
  ii) a feature extraction module to extract relevant features from said desirable data;
  iii) a diagnostic module to apply at least a portion of said relevant features of said desirable data to at least one trained diagnostic model; and
  iv) a pulse parameter estimation module to estimate at least one of said initialized EP pulsing parameters and subsequent pulsing parameters based on an outcome of at least one of said measured sensor data, said diagnostic module and said feature extraction module; and e) a memory module to store said desirable data, said undesirable data, said measured sensor data and said at least one trained model for feature extraction by said controller.

2. The system of claim 1, wherein said EP device comprises:
  a) a central probe defining at least a central lumen and extending from a proximal end to a distal end, at least a portion of said central probe creating a channel for delivery of therapeutic moieties to said tissue, said portion of said central probe having at least one ejection port,
  wherein said proximal end of said central probe is configured to receive said therapeutic moieties delivered to said central probe, and
  wherein said distal end of said central probe is open to define an opening for delivery of said therapeutic moieties to said tissue and has a shape configured to pierce said tissue;
  b) an applicator housing said central probe at least partially, said applicator having a distal end through which said portion of said central probe is configured to extend to an outside of said applicator to contact said tissue and to retract back into said applicator; and
  c) at least two oppositely charged electroporation electrodes (EPEs) configured to be positioned at or adjacent said tissue, said EPEs being adapted to extend from proximal to distal ends, said distal ends having a needle shape configured to pierce said tissue,
  wherein said measurement device is coupled to said EPEs, and said electrodes are adapted to be coupled to said generator to receive at least one of said excitation signal and said electrical waveform for said EP pulse.

3. The system of claim 2, wherein the EPEs of the EP device are coupled to the measurement device, and the EPEs are adapted to be coupled to the generator to receive at least one of the excitation signal and the electrical waveform for the EP pulse.

4. The system of claim 1, wherein said EP device comprises:
  a) a central probe defining at least a central lumen and having a proximal end and a closed distal end, a tip of said distal end having a needle shape configured to pierce tissue and having at least one exit port positioned at a predetermined position from said distal end, said exit port fluidly connecting said central lumen to an outside of said central probe;
  b) at least one channeling wire positioned in said central lumen and slidable within said central probe, said channeling wire having a proximal end positioned in said central probe and a distal end configured to extend to said outside of said central probe and retract back into said central lumen through said exit port, a tip of said distal end of said channeling wire having a shape configured to pierce through said tissue and define an opening through which at least a portion of said channeling wire enters said tissue to create a fluid channel through which said therapeutic moieties are delivered to said tissue,
  wherein said therapeutic moieties are delivered from said central lumen into said channel through said exit port;
  c) a ramp integrally formed with or coupled to said inner surface of said central probe, said inner surface defining said central lumen, and said ramp configured to contact and guide said channeling wire to exit said central probe to said outside of said central probe;
  d) an electrical connector electrically connecting said central probe and channeling wire to said generator;
  e) a small bore connector connected to said central probe for delivery of said therapeutic moieties;
  f) a handle housing said electrical connector at least in part and coupled to said proximal end of said central probe and said channeling wire to facilitate a depth of penetration of said distal end of said central probe and said channeling wire; and
  g) at least two oppositely charged electrodes configured to be positioned in or adjacent said tissue, said electrodes extending from proximal to distal ends, tips of said distal ends having a needle shape, configured to pierce said tissue wherein said electrodes are adapted to be coupled to said generator, receive at least one electrical waveform from said generator, and supply said at least one excitation signal and at least one EP pulse to said tissue, wherein said measurement device is coupled to said electrodes.

5. The system of claim 1, wherein said EP device comprises:
  a) a trocar comprising:
    i) a cannula extending from a proximal end to an open distal end and defining a first lumen configured to receive an obturator; and
    ii) said obturator extending from a proximal end to a distal end, said distal end having a sharp pointed shape configured to pierce through skin, penetrate into body cavities and form a path through which said cannula may be at least partially inserted into said cavity, wherein said obturator is configured to be slidable within said first lumen, said distal end of said obturator configured to extend to an outside of said first lumen through said open distal end of said cannula;

b) at least two oppositely charged electrodes retractably disposed at a distal end of an anchor and configured to be positioned at or adjacent said tissue, wherein said measurement device is coupled to said electrodes and said electrodes are adapted to be coupled to a generator, receive at least one electrical waveform from said generator, and supply said at least one excitation signal and EP pulse to said zone; and c) a central probe retractably disposed at said distal end of said anchor and having an inner surface defining a central lumen and extending from said distal end of said anchor, at least a portion of said central probe configured to create a channel for delivery of said therapeutic moieties to said tissue, wherein a distal end of said central probe has a shape configured to pierce said tissue and is open to define an opening for said delivery of said therapeutic moieties to said tissue.

6. An adaptive control method for controlling EP pulsing parameters during electroporation (EP) of said cells or said tissue using an EP system, said adaptive control method comprising: a) providing the system of claim 1; b) initializing, by said initializing module, EP pulsing parameters for performing said EP in said cells or said tissue, said initialized EP pulsing parameters based at least in part on said at least one trained model; c) applying, by said generator, said voltage and current excitation signals to said cells and said tissue and measuring, by said measurement device, said voltage and current across said cells and tissue corresponding to said applied excitation signals; d) obtaining, by said controller, data from said current and voltage measurements, and processing said data to separate said desirable data from said undesirable data; e) extracting, by said controller, said relevant features from said desirable data; f) applying, by said controller, said at least a portion of said relevant features of said desirable data to said at least one trained diagnostic model; g) estimating, by said controller, said initialized EP pulsing parameters, based on an outcome of said applied relevant features to said at least one trained diagnostic model, wherein said initialized EP pulsing parameters are based on said at least one trained model and said relevant features, to optimize said EP pulsing parameters; and h) applying, by said generator, a first EP pulse based on said initialized EP pulsing parameters.

7. The method of claim 6, further comprising predicting subsequent EP pulsing parameters after said first EP pulse has been applied, by said controller, using said trained model based on a previous EP pulse, and a change in at least one of said relevant features between applied EP pulses.

8. The method of claim 7, further comprising: f) applying a subsequent EP pulse, by said generator, based on said subsequent EP pulsing parameters; and g) repeating said applying said voltage and current excitation signals, repeating said measuring said cells or said tissue, repeating said obtaining said data and separating desirable data from undesirable data; repeating said extracting relevant features; and repeating said applying, until either i) a pre-determined limit of number of EP pulse sequences or cycles of EP pulses is reached, or ii) said diagnostic response prompts a diagnostic decision to terminate said adaptive control method.

9. The method of claim 6, wherein said relevant features are derived from a parametric model fit of magnitude and phase measurements of said voltage and current signals selected from the group comprising intracellular resistance, extracellular resistance, solution resistance, membrane capacitance, admittance, constant phase element exponent, and charging time constant.

10. The method of claim 6, wherein said relevant features are derived from a magnitude ratio or a phase difference of said voltage and current excitation signals and said features comprise: a) values of the magnitude ratio and the phase difference of said voltage and current excitation signals at fixed frequencies; b) at least one of a mean, median, maximum, and minimum of: i) the magnitude ratio or the phase difference of said voltage and current excitation signals magnitude over a narrow frequency band; ii) the magnitude ratio or the phase difference of said voltage and current excitation signals magnitude phase over a wide frequency band; and c) curvature, slope and noise of said magnitude ratio or said phase difference of said voltage and current excitation signals with respect to frequency.

11. The system of claim 1, further configured to include an Electrochemical Impedance Spectroscopy (EIS) mode of operation, in which an impedance of said tissue is measured for optimizing the electroporation (EP) pulse parameters.

12. The system of claim 1, wherein the diagnostic module is further configured to determine if the applied EP pulse was effectively applied for transfection.

13. The system of claim 1, wherein the diagnostic module is further configured to determine if the needle placement of the EP device is correct.

14. The system of claim 1, wherein the at least one trained model is trained using empirical data observed during initial operation of an EP device using fixed pulse parameters and applying at least one machine learning algorithm to the empirical data observed during the initial operation.

15. The system of claim 1, wherein the controller is configured to perform one-step ahead feedforward control, such that before a first EP pulse is applied, the pulse parameter estimation module is configured to initialize the control parameters for the first EP pulse based on the at least one trained model.

16. The system of claim 15, wherein the controller is configured to use the at least one trained model to compare the extracted relevant features to features derived from the empirical data obtained in previous experiments.

17. The system of claim 1, wherein the pre-processing module is configured to separate the desirable data from the undesirable data by at least one of a) de-noising the sensor signals, b) removing a direct current (DC) bias from the sensor signals, c) scaling the data based on standardized values, wherein the standardized values include standard deviation, d) mean filtering, and e) removing outliers from the data.

18. The system of claim 1, wherein the at least one trained model comprises one or more of a physics-based model, an empirical model, or a data-driven model.

19. The system of claim 1, wherein the at least one trained model is trained based at least in part on at least one supervised learning routine.

20. A device for delivery of therapeutic moieties to cells in a treatment zone of a tissue, said device comprising:

a) a central probe defining at least a central lumen and extending from a proximal end to a distal end, at least a portion of said central probe creating a channel for delivery of said therapeutic moieties to said tissue, said portion of said central probe having at least one ejection port, wherein said central probe comprises an open proximal end that fluidly connects said central lumen with a lumen of an injector through which said therapeutic moieties are delivered to said central probe, and wherein said central probe comprises an open distal end having a shape configured to pierce said tissue, wherein both the open distal end of the central probe and the at least one ejection port on a sidewall of the central probe are configured to deliver said therapeutic moieties into said tissue;

b) an applicator housing said central probe at least in part, said applicator having a distal end through which said portion of said central probe is configured to extend to an outside of said applicator to contact said tissue and to retract back into said applicator.

21. A device for delivery of therapeutic moieties to cells in a treatment zone of a tissue, said device comprising:

a) a central probe defining at least a first lumen and extending from a proximal end to a distal end, at least a portion of said central probe creating a channel for delivery of said therapeutic moieties to said tissue, wherein said portion of said central probe is formed of or coated with a conductive material, wherein said proximal end of said central probe is open and fluidly connects said first lumen with a lumen of an injector through which said therapeutic moieties are delivered to said central probe, and wherein said distal end of said central probe is open to define an opening for delivery of said therapeutic moieties into said tissue and has a shape configured to pierce said tissue;

b) an applicator housing said central probe, said applicator having a distal end; and c) a plurality of distal electrodes positioned at said distal end of said applicator surrounding the central probe and configured to generate an electric field with said portion of said central probe, wherein a diameter of the central probe is adjustable, wherein said portion of said central probe and at least a portion of said plurality of distal electrodes are extendable to an outside of said applicator to cause electroporation of said tissue and retractable back into said applicator from said tissue.

22. The device of claim 21, further comprising an electroporation system comprising at least two oppositely charged electroporation electrodes configured to be positioned at or adjacent said zone, said electrodes being adapted to extend from proximal to distal ends, tips of said distal ends having a needle shape configured to pierce said tissue, wherein said electrodes are adapted to be coupled to an electrode power supply, receive at least one electrical waveform from said power supply, and supply a pulsed electric field sufficient for electroporation to said zone.

23. A device for delivery of therapeutic moieties to a zone of target cells of a tissue, said device comprising:

a) a central probe defining at least a first lumen and having a proximal end and a distal end, a tip of said distal end having a plurality of exit ports positioned at a predetermined position from said distal end, said plurality of exit ports fluidly connecting said first lumen to an outside of said central probe;

b) a plurality of channeling wires positioned in said first lumen and slidable through said plurality of exit ports on a sidewall of said central probe, each of said plurality of channeling wires having a proximal end positioned in said central probe and a distal end configured to extend to an outside of said central probe through said plurality of exit ports and retract back into said first lumen through said plurality of exit ports, wherein each of said tip of said distal end of said central probe and a tip of said distal end of each of said plurality of channeling wires has a shape configured to pierce through said tissue, wherein at least a portion of said plurality of channeling wires enters said tissue to create a fluid channel through which said therapeutic moieties are delivered from said first lumen to said tissue;

c) a ramp integrally formed with or coupled to said first lumen, said ramp configured to contact and guide said plurality of channeling wires to exit said central probe to said outside of said central probe;

d) an electrical connector electrically connecting said central probe and said plurality of channeling wires to a power source;

e) a small bore connector connecting said central probe to a syringe for delivery of said therapeutic moieties; and f) a handle housing said electrical connector at least in part and coupled to proximal ends of said central probe and said plurality of channeling wires to facilitate a depth of penetration of said distal end of said central probe and said distal end of said plurality of channeling wires.

* * * * *